US012084657B2

(12) United States Patent
Wang et al.

(10) Patent No.: US 12,084,657 B2
(45) Date of Patent: Sep. 10, 2024

(54) OLIGONUCLEOTIDES TARGETING RNA BINDING PROTEIN SITES

(71) Applicant: Hoffmann-La Roche Inc., Little Falls, NJ (US)

(72) Inventors: Congwei Wang, Basel (CH); Christian Weile, Farum (DK); Martin Ebeling, Grenzach-Wyhlen (DE); Lars Joenson, Viby Sjaelland (DK); Jonas Vikesaa, Fredensborg (DK); Ravi Jagasia, Basel (CH); Meiling Li, Aargau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 130 days.

(21) Appl. No.: 17/383,709

(22) Filed: Jul. 23, 2021

(65) Prior Publication Data

US 2022/0033818 A1 Feb. 3, 2022

(30) Foreign Application Priority Data

Jul. 23, 2020 (EP) .................................... 20187354

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/3231* (2013.01)

(58) Field of Classification Search
None
See application file for complete search history.

(56) References Cited

U.S. PATENT DOCUMENTS

2020/0147124 A1 * 5/2020 Beigelman ............ A61K 45/06

FOREIGN PATENT DOCUMENTS

| | | | |
|---|---|---|---|
| WO | WO-98/39352 | A1 | 9/1998 |
| WO | WO-99/14226 | A2 | 3/1999 |
| WO | WO-00/47599 | A1 | 8/2000 |
| WO | WO-00/66604 | A2 | 11/2000 |
| WO | WO-01/23613 | A1 | 4/2001 |
| WO | WO-2004/046160 | A2 | 6/2004 |
| WO | WO-2007/090071 | A2 | 8/2007 |
| WO | WO-2007/134181 | A2 | 11/2007 |
| WO | WO-2008/150729 | A2 | 12/2008 |
| WO | WO-2008/154401 | A2 | 12/2008 |
| WO | WO-2009/006478 | A2 | 1/2009 |
| WO | WO-2009/067647 | A1 | 5/2009 |
| WO | WO-2010/036698 | A1 | 4/2010 |
| WO | WO-2010/077578 | A1 | 7/2010 |
| WO | WO-2011/017521 | A2 | 2/2011 |
| WO | WO-2011/156202 | A1 | 12/2011 |
| WO | WO-2013/154798 | A1 | 10/2013 |
| WO | WO-2014/076195 | A1 | 5/2014 |
| WO | WO-2015/113922 | A1 | 8/2015 |
| WO | WO-2017/106283 | A1 | 6/2017 |
| WO | WO-2019/241648 | A1 | 12/2019 |
| WO | WO-2020/097342 | A1 | 5/2020 |
| WO | WO-2020/247419 | A2 | 12/2020 |
| WO | WO-2021/195446 | A2 | 9/2021 |

OTHER PUBLICATIONS

Chan et al. (Chan et al. "Antisense oligonucleotides: from design to therapeutic application." Clinical and experimental pharmacology and physiology 33.5-6 (2006): 533-540).*

Arnold et al., "ALS-linked TDP-43 mutations produce aberrant RNA splicing and adult-onset motor neuron disease without aggregation or loss of nuclear TDP-43," Proc Natl Acad Sci USA. 110(8):E736-45 (2013).

ATtRACT database (https://attract.cnic.es/results/e9f29380-8921-406e-84a8-27ce9b9398b4#).

Ayala et al., "Human, *Drosophila*, and C. elegans TDP43: Nucleic Acid Binding Properties and Splicing Regulatory Function," J Mol Biol. 348(3):575-88 (2005).

Ayala et al., "Structural determinants of the cellular localization and shuttling of TDP-43", J Cell Sci. 121(Pt 22):3778-85 (2008).

Conti et al., "TDP-43 affects splicing profiles and isoform production of genes involved in the apoptotic and mitotic cellular pathways," Nucleic Acids Res. 43(18):8990-9005 (2015).

Humphrey et al., "Quantitative analysis of cryptic splicing associated with TDP-43 depletion," BMC Med Genomics. 10(1):38 (2017). (17 pages).

Jana et al., "Ceramide and neurodegeneration: Susceptibility of neurons and oligodendrocytes to cell damage and death," Published in final edited form as: J Neurol Sci. 278(1-2): 5-15 (2009). (24 pages).

Klim et al., "ALS-implicated protein TDP-43 sustains levels of STMN2, a mediator of motor neuron growth and repair," Published in final edited form as Nat Neurosci. 22(2):167-79 (2019). (36 pages).

Melamed et al., "Premature polyadenylation-mediated loss of stathmin-2 is a hallmark of TDP-43-dependent neurodegeneration," Published in final edited form as Nat Neurosci. 22(2):180-90 (2019). (28 pages).

Nasu-Nishimura et al., "Role of the Rho GTPase-activating Protein RICS in Neurite Outgrowth," Genes Cells. 11(6):607-14 (2006).

Neumann et al., "Ubiquitinated TDP-43 in frontotemporal lobar degeneration and amyotrophic lateral sclerosis," Science. 314(5796):130-3 (2006).

(Continued)

*Primary Examiner* — Kimberly Chong

(74) *Attorney, Agent, or Firm* — Clark & Elbing LLP; Thomas J. Takara

(57) ABSTRACT

The present invention relates to antisense oligonucleotides which are complementary to conserved TDP-43 binding sites on pre-mRNA transcripts, which are capable of restoring RNA binding protein function in the processing of multiple independent mRNAs in TDP-43 depleted cells.

31 Claims, 29 Drawing Sheets

Specification includes a Sequence Listing.

(56) References Cited

OTHER PUBLICATIONS

Prasad et al., “Molecular Mechanisms of TDP-43 Misfolding and Pathology in Amyotrophic Lateral Sclerosis,” Front Mol Neurosci. 12:25 (2019). (36 pages).
Salter et al. “Truncating SLC5A7 mutations underlie a spectrum of dominant hereditary motor neuropathies,” Neurol Genet. 4(2):e222 (2018) (8 pages).
Tollervey et al., “Characterizing the RNA targets and position-dependent splicing regulation by TDP-43,” Nat Neurosci. 14(4):452-8 (2011) (8 pages).
Winton et al., “Disturbance of nuclear and cytoplasmic TAR DNA-binding protein (TDP-43) induces disease-like redistribution, sequestration, and aggregate formation,” J Biol Chem. 283(19):13302-9 (2008).
Yang et al., “Partial loss of TDP-43 function causes phenotypes of amyotrophic lateral sclerosis,” Proc Natl Acad Sci USA. 111(12):E1121-9 (2014).
Bergstrom D E, Unnatural Nucleosides with Unusual Base Pairing Properties, Current Protocols in Nucleic Acid Chemistry, 2009, vol. 1, No. 4 (32 pgs).
Brown A-L et al., “Common ALS/FTD risk variants in UNC13A exacerbate its cryptic splicing and loss upon TDP-43 mislocalization”, bioRxiv 2021.04.02.438170, URL: https://doi.org/10.1101/2021.04.02.438170 (38 pgs).
Caruthers M H et al., Chemical Synthesis of Deoxyoligonucleotides by the Phosphoramidite Method, Methods in Enzymology, 1987, vol. 154, pp. 287-313 (27 pgs).
Deleavey G F and Damha M J, Designing Chemically Modified Oligonucleotides for Targeted Gene Silencing, Chemistry and Biology, 2012, vol. 19, p. 937-954 (18 pgs).
Freier S M and Altmann K-H, The ups and downs of nucleic acid duplex stability: structure-stability studies on chemically-modified DNA:RNA duplexes, Nucleic Acid Research, 1997, vol. 25(22), pp. 4429-4443 (15 pgs).
Hansen L D et al., Entropy Titration. A Calorimetirc Method for the Determination of deltaG° (K), deltaH° and deltaS°, Chem. Comm., 1965, pp. 36-38 (3 pgs).
Hirao I et al., Natural versus Artificial Creation of Base Pairs in DNA: Origin of Nucleobases from the Perspectives of Unnatural Base Pair Studies, Accounts of Chemical Research, 2012, vol. 45(12), p. 2055-2065 (11 pgs).
Holdgate G A et al., Mesaurements of binding thermodynamics in drug discovery, Drug Discovery Today, 2005, vol. 10(22), pp. 1543-1550 (8 pgs).
Ma R et al., “TDP-43 represses cryptic exon inclusion in FTD/ALS gene UNC13A”, bioRxiv 2021.04.02.438213, URL: https://doi.org/10.1101/2021.04.02.438213 (43 pgs).
Manoharan in Antisense Drug Technology, Principles, Strategies, and Applications, S.T. Crooke, ed., Ch. 16, Marcel Dekker, Inc., 2001 (85 pgs).
Manoharan M, Oligonucleotide Conjugates as Potential Antisense Drugs with Improved Uptake, Biodistribution, Targeted Delivery, and Mechanism of Action, Antisense and Nucleic Acid Drug Development, 2002, vol. 12, p. 103-128 (26 pgs).
McTigue P M et al., Sequence-Dependent Thermodynamic Parameters for Locked Nucleic Acid (LNA)-DNA Duplex Formation, Biochemistry, 2004, vol. 43, pp. 5388-5405 (18 pgs).
Mergny J-L and Lacroix L, Analysis of Thermal Melting Curves, Oligonucleotides, 2003, vol. 13, pp. 515-537 (23 pgs).
Mitsuoka Y et al., A bridged nucleic acid, 2',4'-BNA$^{COC}$: synthesis of fully modified oligonucleotides bearing thymine, 5-methylcytosine, adenine and guanine 2',4'-BNA$^{COC}$ monomers and RNA-selective nucleic-acid recognition, Nucleic Acids Research, 2009, vol. 37, No. 4, pp. 1225-1238 (14 pgs).
Morita K et al., 2'-O,4'-C-Ethylene-Bridged Nucleic Acids (ENA): Highly Nuclease-Resistant and Thermodynamically Stable Oligonucleotides for Antisense drug, Bioorganic & Med.Chem. Lett., 2001, vol. 12, pp. 73-76 (4 pgs).
Santalucia J, A unified view of polymer, dumbbell, and oligonucleotide DNA nearest-neighbor thermodynamics, Proc Natl Acad Sci USA, 1998,, vol. 95, pp. 1460-1465 (6 pgs).
Seth P P et al., Synthesis and Biophysical Evaluation of 2',4'-Constrained 2'O-Methoxyethyl and 2',4'-Constrained 2'O-Ethyl Nucleic Acid Analogues, J. Org. Chem., 2010, vol. 75, No. 5, pp. 1569-1581 (7 pgs).
Sugimoto N et al., Thermodynamic Parameters to Predict Stability of RNA/DNA Hybrid Duplexes, Biochemistry, (1995), vol. 34, pp. 11211-11216 (6 pgs).
Uhlmann E, Recent advances in the medicinal chemistry of antisense oligonucleotides, Current Opinion in Drug Development, 2000, vol. 3, No. 2, pp. 203-213 (11 pgs).
Wan W B & Seth P P, The Medicinal Chemistry of Therapeutic Oligonucleotides, J. Medical Chemistry, 2016, vol. 59, pp. 9645-9667 (23 pgs).

* cited by examiner

Fig. 6

AGTCTTCTCTCTCGCTCTCTCCGCTGCTGTAGCCGGACCCCTTTGCCTTCGCCACTGCTCA<br>
GCGTCTGCACATCCCTACAATGGCTAAAACAGCAATGGˇGACTCGGCAGAAGACCTTCGAG<br>
M A K T A M G L G R R P S R<br>
AGAAAGGTAGAAAATAAGAATTTGGCTCTCTGTGTGAGCATGTGTGCGTGTGTGCGAGAG<br>
E R - (SEQ ID NO: 124)<br>
AGAGAGACAGACAGCCTGCCTAAGAAGAAATGAATGTGAATGCGGCTTGTGGCACAGTTG<br>
ACAAGGATGATAAATCAATAATGCAAGCTTACTATCATTTATGAATAGCAATACTGAAGA<br>
AATTAAAACAAAAGATTGCTGTCTCAATATATC (SEQ ID NO: 120)

Fig. 8

GAAATTAATCCTTTTGGTAGTCATATTAGGTAGAATCATGATGCACATTCTAATAAGTCACACTGTACTCATG
TCCCTTTAG^CCTGGAAACCATCTCCCTGAAACTGGAACTCAGCTTTTTCGTCTGTATCTGTAATGCTTTCAT
GATGCCTGGAAAATAGAAGAGACTTAATAAATACATGATTGATGAGTGAGTGAGCGAGTGAATGAATGAAGAG
AAAAGAGCAGAAACGAAACCAAAACTGTCAAGAAAAAAAAATCAAAGATCAATTCTTGTCATACTTACTTCCT
ACTTCTTTTAGCCATATTCTAATCTAAAGGATCATCGATTTTAATTTAAATATGTACTTCTTATTCTGTTGTC
GTATGATGATATTTTAAAAACTAAGAATGTAAAATCAAAGTAAATCAGAAGTGTATTATGTGGAGAATGTGGG
AATGATTCTGAAAGTCATACCGTCTTTTGGAGGAAGCATTTTGGAGGTTTCTAATGTTATATTTTGACTGGGT
CATTATTCGCTGTGCATTTGGCTGGTTTGTTAGATGGTTTGGGGGTAGCTAGTAAATAGCCTTTTTTTAAAAC
TAGGATTTTTTTTACAAAATATATTGGATTTCTTATATTGCTTTCCTACTCTTTCGTGAAAAAATAAAACAGA
TCTTTTCTTCTTTTTTCTTCTGACATTGTTTTTCAGTTTTTGCTCCTTTTCTTCAAGATTCAAGTTTATGCTT
TTCTTTCATTTTGCCACCTATTTGTATTAAATGACTCATTTGTTTCCCTTAAACTTATAAGTAATAGTTATGT
AATTTTATTTATTAAGCTCATTATGTGATTTTTGTGTAGACATTCAGTCCTTCTACTCAGGGAACACAAAATA
TAAGAAAACGATTCAGATGCTTGCCATGAAGTATTACGTGTGTAGAGACTTGGACATATTATCAGGAAAAGAC
CTCTAATTCTCCATATTTTCAATGTTTTCCTACTTATTTGGAAGAATAAACAGATATGAATCTAATAACACAC
AGATATACACATCCAATGAAAATTACCGATACTTTTTTTTATAAATGGTAGCTTATTTTTATGAAAAATTTAT
GTGTGCTCGGAGAGCCTGATAATATGGAAATAAAATACTGTGCTCTGAAGGGTTTTTCTTGAAGACAAACCTT
TTGTGTACCTGGGTGAATCAGCATGCTCATTTGGAGCATATATAATGAGAAGCATCTTCTCAGTGCTTTACAG
GAAAGAATTTTAACTATTTTCCTAAGTAATGATGTTAATTATCCCAGTAATCTCTAAATACATTCCCTTTGAA
GCAGAAGACTGAAATTTTGTAGCCCCAAATTTTATTATTCCACTTCCAGTTTTTAGAATTGAAACCTAAGACA
CCAAGTTTATCATTGGTGGGACAATGTGAGAAATAGAACCCAAGCTTTTATAAAGATGCTATGTATTTTGCAT
ATCATTTCGACACAGAGGTTGCTTCTAATATCAATTAAATCCACAAGAAGTACCCAGCAATTCTACCTGCCCT
TCATCTTTACTACATAACCATAACCTTTTCTTGTTACTGAAAGTCTTGAATATTTTTAGAGGTAGAAAGCATG
TAGTTGAAAATGTATTCATATGAAAACTAAGGTTCCTTCCCTGCTAACTTGACCAGATAATGACCATTTCAGG
CTCTCAGGGCACTGGTAAATTAATTCACTTGCTAATTTTATACATTGTGTCAGGACGGTGTTCCTGAGTTTTA
AATATACAAAGATGGACGATGCATGGTTTTGCTCTTGAAGAGCCCACAGTCAGAAAAGGGTAATAGTTGTATG
AACAAATAAATGATAATTTTGAAATATTTTTCTATGAGCACATAGAACACAGTGCTCAGCCACCTCTACTTGT
GGGTATTCAATGAAGGCTCGCTAAAGAGTGATAGTTTACCTGGATTTTGAACAATAGCCAAGAATTTTTTCTA
TACGAAGAGCGTTATGGGAGAGAGTCCAGCTAGAGGAAATTGTTTTGTGAAGAAGTCATAGCATGGTTGGTTT
GTATGGCAAAAGGTAACACTTCACTTGGCCTAGGGTTGTGGAATATGGAAATACAATAATAATTAAATGTAAA
TTATGAAAGGCCTTCTCTGCCAGGCAGTATATTGCAGTAGTCAAAAGCATTGGCTCTGACTGGATAAAGAAAA
ATGTGGCACATATATACCATGGAATACTATGCAGCCATAAAAAAGGATGAGTTCATGTCCTTTGCAGGGACAT
GGATGAAGTTGGAAGCCATCATTCTCAGCAAACTATCACAAGAACAGAAAACCAAACACCACATGTTCTCACT
CATAAGTGGGAGTTGAACAATGAGAACACATGGAATAGGGAGGGGAACATCACACACCAGGGCCTCTCGGGGG
GTTGGGGGGCTAGGGGAGGGATAACATTAGGAGAAATACTCAATGTAGATGATGGGTTGATGGGTGCAGCAAA
CCACCATGGCATGTGTATACTTACGTAACAAAACTGCACATTCTGCACATGTACCCCAGAACTTAAAGTATAA
TAAAAAAAGATATATGTA*TGTGTGTGTGTGTGTGTGTGTGTGTGTGTGTGTGTGTGTGTG*AAATAAAAAACAAAA
CAAAAGCATTGGCTCTGTACTTGGACTGCCTGAGTTGGAATCTCTCACTTCTGCCAGTGTTTCCTGCCTGCCC
TTGGGTAAAACTTACTCTCTCTAAGATACAATTTCTTCTCTGTAAAAATTGGGAA (SEQ ID NO: 121)

Fig. 10

CTTTTGTCCTGTGGTATTCTGTAAAGGTGATCCAGGGTGATGTTCCTACAGCAACTTTGACTTTCGATTAGTAGAGTCTTTTATTGGATTGTTTAACTTTTAG^GAGAGCAGTCCTGGTTCATAGTGTACACTCTCCATTCCAGTTGTTCATCCAGGAGACAGACACTTCAAAAATGTAAAGATGACTGACGAAGGTG^**GTATGTAGTGTTTGTCTCTGAAAAAAAAAAAGATAGTATTTCTCTCACAAGCAGAAAACATATATGGAC*GTGTGTGTGTCTGTGTGTGTGTGTGTGTGTGTCTGTGTGTGTGTG*TTTATTGTAGGAACACAGGCTAACAGAAACAGCATTAAG** (SEQ ID NO: 122)

Fig. 12

ACACTCTCCACCAAAGAACAGCCAGAAAAGATGGCAGGCAGTATTGGTTAAAATCTGGACACTACTGTGTTTTATA GTCTTCTTACAGATCTATCTGATGTCAAATTTTATTAACCTTTTCCACTGTAATTTTTTCTCAAG^GTTGAAATAACTGG ATCCCAGTTACATTTTACATGGAAT^**GTAAGTGTGTGTGTATTTGCACATGTGTGTACACACAGTATGTGTGTGTTCAT ATATATATACATAATATATGCAGGGTATGTGTGTATTTATTGGTAAGCAACTCTATTCAAGAACTTTCTAATCTTTTG TATGTAGA*GTGTGTGTGTGTGTGTGTGT*ATATATACACACTAAAGACTAGAAAGTTCTTAAATAGAGAAAGTTG TTTATCAACAAATACGT** (SEQ ID NO: 123)

Fig. 14B

GAGTCTTCTGACAGTGCCAATACCACCATAGAGGATGAAGACGCTAAAG^GTACCTGCACT*TGAG*TCCTTGCCCCCC
CAGCGGCCTTGGCATTGCTGGGTTGCTCTTTGAGGTGGGTGGGACTTGGGCAGGGTCAACTCTCCTGCGACGCCTAG
TTTATGCATGTGTTGAGGGGCTCAGGGACCCTGTAGCTGTAATCCTGCTCCAAGCCTGGGTGTCAGGCCTGCCCAGAG
CGGAGAAGCATGGCAGAGATGACCGACAGCTGGGCAGTCTCGGTCACCGCATCCAAGTGAGGAAGCCACGGCTTTG
CATGGAGGCAGGTTCTCCACACCAGGACCCTCACGGGGAAACAGGCCCATGGGTAGAATTTGTTCCAAGATGCTGTC
CTTGTCTTAAAGCTCCTTAAGCTTGCGTTTCTGTCCAGCATGCACTTGCCAAGTGGCCGGGCAGCTGGGTGAGTGTTTC
CGTGTTTGCCTTTGCTTAGCCAGGAGTGTCCTGCTGCGGTGGGTTTCTGCACCACAGATTCCAGGGCCCCCTCCCTTGC
TCACCCAGGCCAATGTCTTGTGTGTTCCCCAAGAGGCCCCCAGGGCACCAGGCACTGGGGCATGCTCCATGGATTCTG
CCGCCTCCAGACCACCCACATGGGGCCTCCTGACCCTCATCGCTCACACGGTCACCTAATAAGCCTTATGCTGTTCTCA
GGGCTACCCTGGTGCCCAAAAAGGGTCAGCCACTCTGCCAGTTTAGGGGAGAAAACTTCTCACCTGTCCAAAGCATAG
CCTTGCTCCTGCCCGGCCTACCCAGCTATGACACTGTCCCTGAGCAGAGATGAGCACAGGACTTTGGGCCCTGGATGC
CGGAGAGTGGGTGTTTGTGTGATTCCCCTGCAGTCTGGAACAGGCCCCAAAGGCAACAGCATGAAGGCTGTCCAGAG
GTTCTCCATCACCCTCAGCCGAGTGGGGTGCTGAGCAGTGAGGGAGGGGACCTGGGAGGGGGGCCCAGCCTGGATC
CTGCAGGGGAGAAGAGAAGACAGCCAGAAGCCAGCAGCTGTGGCTCAGATCTGAGCCCGAGCAGCCTCTCGAGGTG
GAGGCAGACACCCCCCACCCCACCCCGTGCAGAAAGAAGCCTTGCCAGCCTGCCCTGAGGCTGGTACAGAGTCCAGG
CAGGCTCAGTGGCCATCATGCCCCTACGATGACTGTCACTCCCTCTCCGTGCGCCTGGCCTCTGCTGGCTCTGGCCAGG
GGTGGTCACAGCACTAGGGTGGCAGGGTGGCCTCTGACTCTGCGCCAGCCTGCACTGGCCTGTGCTGCCCTGGCCTC
TGCTGGCTCTGGCTCTGGCACCGGTCCCGTGTTGGCTCCTTCAGCCTTCACATACCTGCTGCGGCCACCACAGGCCCAG
GACCCCCACAGGTGGCCACCCCACCTCCACCCCAGGAGCCCCAGGTATCCAGCTGTCACCCCCTCCCTCCCTCCTGGCC
TCCCCCTGTCCTTCTCCAGTTGCCTTCTTTTCCTGCGGGCGCACCACCCACCTGCCTGCCTCACCTGTTCCGCCTCAGCCC
CCAGGGTCCCCGACATCCTGAGCTCAGTGAGGAGGGGCTCGGGAGCCCCAGAAGCCGAGGGGCCCCTGCCCTGCCC
ATCTCCGGCTCCCTTTAGCCCCCTGCCAGCCCCATGTAAGTAGCCTGGGTCCTGCTGCTGTGGGGGTCATGTTGGAGG
GCTGGCAACCCCCTAGAGGGGCCACTCCAGAGCCGAGGGCAGGCTGAGCGTGGACCCTGGCTCCAGCCTCATCACCC
CACAATCCCTCACTGGGGCTTTCCAGGGTGGCCCCAGCCCATCGAGCCCCACCTCTTTGTGAGGAGGGCCCTGGACCA
CTTTCCTGCTCAAGGCCACTGGGCAGGATGGGAGGCCCTGGAGGCTCGGGCCTCAATTCCAGTCTTCAGGGTCGGTG
CAGGCCTCACTCCACCTCAGCTTGCGGGCGGGGGGGCTCCCTGCTATTGAGGCAGGCTCTGATTCAGGGCCTGATCCC
AGGGCCCAAGGGGTCTAGAACACGGGACCCCTCCCACTGGCCTCCTCCGCCTTGCCGCCGCCTCGTGTGTCTGTCTGC
CTCATGTTCACGTCTCATCTGTTCCACCCCAGCCCCCAGGATCTCTGACATCCTGAACTCTGTGAGAAGGGGTTCAGGA
ACCCCAGAAGCCGAGGGCCCCCTCTCAGCGGGGCCCCCGCCCTGCCTGTCTCCGGCTCTCCTAGGCCCCCTGTCCTCCC
CGTGTAAGTAGTGGCCCCCAGGCCTGCCGCCTCTGCTGCCGGACAGCTCCCTGCGAATGGCCGGCGCTCAGCAGCTTC
CCACCTGCATGCACGGCCCAGCTACCCTGCCCCGGCGCCGCAGCCTGGAGTCCTGCCCTGGCGGGGCTTCCTGTGGGC
TCCCATGCTAACCAGCAGGGCAGCTCCTGGCTTCTCCCTAAGGGGCCCAGACCCCTCCACGGCTCCTGCTCCCACTGCC
ACTCCCCGCTCGCTGTCCAGCCCCAGGCCCCTCTCCAAAATGTCTGTCCCAGCCCTGGGCAGCCCTGGCCCCTCCGAGG
CCCCCCATGCCCCTAGGCCCTCTCTGCTGATCACTGTCCCAGCCCCACAGACTTCACACCCACCCAGGGGCCCTGCCCA
TGGTGCCCAGGAGCTGCACTCAGGGCCACCCTGGTTCCTGATGTGGCCCCAACCCCTGAGCACCCTCCCTCAGTCTAG
GAGGCTGAGGAAGGTGCCAAAACTGGAACCCCGACCAGGGTCTCTGGAGCTCACCAACAAGGGGATAGTACGGAGA
ATCATAAGCCTGGCCTCTGCTGACCTGGGCTGTCCTCATGGGGCCAGGCCAGGCCTCCTCTGTAACGCCCGTGACTCC
CTCCTCTCCCTGTAACCCCGTCCAGCGTTCCTCAAGGGCCACTTACCTGACAGCTTCTTGCTGGCCAGCAGCCTCTCCCT
GGAGGGTGCCCTCTGCCCCCAGCAGCTTCAGCCCACGCCACCCGACAGCCAGAGCATCTGCCCTTCACTCCTGCAGCC
TCCTCTCCACGCACCACGCTGTCCGCAGCAGCACCCTCTGTCCCCCTGTCTCCCTCCGTCCCCCCATATCCCCCTCGGTC
AGCCTACAACCTCTCCACGTCCCCCTAAGTCCACGCTCTATCCCTACATCCCCCTCTGTCCCCCAAATTCCCCTCTTTCCC
TCATTTCCATTTTCCTCCCCAAACTCTGCTCTGCCCCTCACATTCTCCCTCTGTCCCCCACACCCTCCTCTGTCCCCCAGAC
TCTCCCTCTGTCCCCCACACCCTCCTCTGTCCCCCATATACCCCTCTGTCCCCCACACCCACCTTGGTCCCTTCACGCCCTT

Fig. 14B cont.

TTCTGTCCCCCACACCCCCTCTGTTCCCTACACTCTCCCTCTGTCCTCCAGACCCTCCTCTGTCCCCCACACTCCCTCTGTC
CCCCACACCCCCTGTCCCCCACACTCTCCCTCTGCCCCCCAGACCCTCCTCTGTCCCCTACACTCCCTCTGTCCCCCATAT
CCCCCTCTGTCCCCCACACCCTCCTCTGTCCTCCACCCCCTGCCCCCCATACCCCCTTCTGTCCCCCACACTTCCTCTGTCT
TCCACACCCCCTCCTGTCCCCCACACCCCCTCTGTCCCCCAGACTCTCCCTCTGTCCCCCACACTCCGTCTGTCCCCCACA
CCTCCTGTCTTCCACACCCCCTTCTGTCCCCCACACCCCCTCTGTCCCCCATACTCTCCTCTGTCCCCCACCTCCCCCTCTG
TTCCCCACACCGCCTTCTGTCCCCCACACCCCCTCTGTCTTCCACTTCCCCTCTGTCCCCCACATCCCCCTCTGTCCCCTGC
ACCCTCCTCTGTCCCCTGCACCCTCCTCTGTCCCCTGCACCTCTCTCTGTCCCCCACATCCCCCTCTGTCCTCCACACTCCC
TCTGTCCCCCACATCCACCTTGGTCCCCTCACGCACCCCCATCCCCCATGACCCCTTCTGTCCCCCACACCCCCTCTGTCT
TCCACACCCCCCTCTGTCCCCCACACCCACCTTGGTCCCCTCATGCCCCCCATCCCCTACACCCCCACTTTGTCCCCCCAC
ATGCCCCTCTGTCCCCCACGTTCCCTTCTGTCTCCCACGTCTCCTCCATTTCCCGTTTCCCTCTCTGTCCCCCAAGCTCCCC
TCCATCCCCCACATCCCCTTCTTTCCCCTATATCCCCTCTGTCGGCCCAGGTCCACCATCTTCCCCCCACACCCCCCCATTC
TCCCTTCCTCCCCTCTGTCCCCTTGTGCCCCATCCCCCACATCTGCCTCTGTGCCCCTCAATCTCTGGCTTGGCTGTCTGC
CCATGGTTTCTCTCCTGCGTGCCCCCCGTGCCTGCCTTGTGTTCACGTCTCGTCTGTTCCGCCCCAGCCCCCAGGATCTC
TGACATCCTGAACTCTGTGAGGAGGGGCTCAGGGACCCCAGAAGCCGAGGGCCCCTCGCCAGTGGGGCCCCCGCCCT
GCCCATCTCCGACTATCCCTGGCCCCCTGCCCACCCCATGTAAGTAGCACCTTGAGTGGCCGTGGCAGCGGCTGCCCG
GAGGGGCTCGGGGCGTGCGAGCCTGGCAGTGGTGCTCTGGGAAGGGCCATTCTTGCGGAGGAGGGCGGGGCACAG
GATCCCTCTGCTGGGTCCCAGGGAATTGCTTTGAAGCACATGAAGGTGCCACTGGGTCTCAGAAAATGGAGGTTATG
GTTATGAAGTGTGTATGACATATGTGTATAGGAAGAGCGTCCGAAAGAGCAGGTTTGTTGCCGACCCCAGCATTCGC
AACCCTGAGGTCCACAGCTTTCTCCTGATGGGAGGGGAATGGGTGGCAAAGGGTCTGCGCGTGTGGCAAGGGCTAG
CACGCCAGGAGCTGCTGGCTTGGGTCAAGGTGGACCTGCTGGGCCGGGACAGAAAAGTGTCAGTCCCGGCCTGAGA
CGCTCTAGCATTAGAGCTGTCCAAGTCCAGACAGCAGGGAGCAGGTGGGGATCGGGAGGCGCGGATCTGGGGGGC
AGCTGGGGCCAGGCTGAAACAGAGCGGGCGGGACAGGAAGCACAGGCTGGGCAGCCTCCCCGGCCAGGGAGGAGC
CAGGCTGGGCCACCTCCCGGTCTGTCTGCCGACTACCCGCAGTATCACTTACAGGGATGGATGACATCCCAGGGCTGC
TGCCACCCCCACCTGTGGGGAGACACCAGACTGGGGGTGGTGTGGAGATACTCTTAGAGAAGAGGCTGCTGGGCCA
CGGGCTCGGCATGGCAGGGCAGTGGCTAGGTAAGTACTTGAGGGACAGGTGGGGTCTGCTTGCCACCGTCCCCTCTG
CAGGCTGGGCCTGGGGGCTGCTGCAGGCGGCCAGGGCAGAAGGGTGTGGGGAGAGTGAACCCACAGGAGCAGCG
GCTCGAGGAGGGGGATGCAGGCTGCAGGCTCAAAGGGGCACTGGATCCACCCTGGGTGCCCGAGAGAGCAGGGGG
CAGCCCCTGGAGGGGTACTCACCCCCAGAGCTTCTGTGGTCGGCTGAGGACCCCCAGCAGGGGTTGACTGAGGGGAT
CAGAGGCAAGCAGCTGAGGGGAGAGGCCAGGTTCTTGATGCTGATAGGGTCGGGGTGCCTGGGCGACCAGAACTCA
AGGAGGGAGGCATGGGGAGGGGCCGCCGTGCAGCTGGGGTGGGTGCACCGCAGAGCCTCTGGGAGTGGTCAGAAC
CCCCGACACCTGCCACTTCTACAGCAGCTCATCTGATTTTAAGGGGCTTGCTGCCCTTGCAGAAGTGGAGGGGTGTGC
CCAAAGGAGCCTGCCTGGAAGGTCACCCCATCAGGTTGGCATGACCCCAGCCCAGGACTGCAGCCTGCCCTCAAGGT
CTGTGCAGTATCTGGGGTGAGTCCTCTGAGGACAGGGCCCAGGGTGGGTGTGGAGTGGCCAGCTCGGGGCTCGGTG
TCCAGGCTCACCTTCAGGGGCCACAGCACAGACCTGCCCTTCCAGAGTCTTCCCTGAGCTTGGCTGGGGAGGAGGGG
GCTGCAGGAAGGAGCTGTGAGCAGGGCAGGATGGAGATTCGTGTGGCCCTCCTGGGAGGGGCTGGGCAGGGCTGG
GAAAGGGGTGGGTGAGATGTTCCGGAACTCAGGGAAAGGAAGAGTCTGGGTACTGCCCTGGGGGCACCTGGGCCC
AGGTGGCAGGTGGCCAGCTTTCTGCCTCCTTTCCACCTCCTTTCTCCAGAAGGCACCCACCAGCTGTGTAAATAGGGCA
GGTGCCCACGGCCCGCCTCAGGCCCCGTCTCCTCCCCACCCACGCTCTCTAATCGCGGATTATACACAATCCAGCCTGA
TCCCTGGGCAGCTGCCCTCCCTCCCGCAGCCACCTCTGGCTCTGAGAGATGGGCTTGGGGCCAGCCTGGGGTCCCAG
GAGTCCAGGCCAGGATGAGAACCTGCTCTGACCCCACCTGGACGCATTAGGCCTGCCTGGACCTGTTGCCTCACCCCA
AGAGAGCCACAGGCAATGCAAAGGCTCCTGTTCATGTCAGGGCACCTGGAAGGCCTGACTTGCAGAGGCTCTTGGCT
CGTGCAGACCCCTCCAAGCCCAGGCCCTGCCCACCACCTCCCCTTTGTCTCTGGAACTGCCAGGACAGCTTGTCCTCAG
CCAGCAGGTTTCCCGACCCGGGCACCTCTTCATGTTGGGCCCCCCTCCTTTCCCTCCATCAGGGATCATGCCCTTCTTCA
GGGGCCTGGATATCAAGGACACAAAAGCTCCCATGTGCTATGTGGGGAGGCAGAGTGGGGGCTGGGTTGAGCTGG

Fig. 14B cont.

GGTCTGGGCAGCGCCATTCCGCAGGGCAGGGGCAGCCTAGGCTTCCCATCTGTGGAATGGGTGGGTGGGTCTCACA
ACGGACCTGCTTCCCGTACTTCAGCACGGTTACCACTCTTGATTGGAACTCTGACCATGCATCTCCTCTTCTGTTTACTT
CACGCTTTCTCTTCCCATCAACTCCCATTTTAATTACAATTTGTTTAAAAGCACTGCATATTACTTCATTAAACAGAAGAT
TAGTTTCACTTACCATTAGTGTAAGGTGACTATAGAACCAAAGCAGACTGGAAACCAAATGACATAATGTCATTCTCTT
CTCCATTCCAGCTGCCTGCTGCTGTGCGCCTGAGAACCCCTGTGGAGTGGGAGGGGCAGCTGTCTCTGTACATTAGAA
AGGGAGGTTAACTAAGTGACAGGAGGTGTTTGGGACATGTGGACACCAGACTTCTCTCTTGATGCAAGGAGGGCAG
AGCCAGGCAGCCTAGTGGGGGCTGGCTTGGGGGCTGCTGGAAGGACTGGCTACAGGTGGAAGAGAGGTCAGACCT
GAAGCTTGGGGCCACCTCCAGGAAAGGACAGGTGAAAGTGGAGGCATGAGGCAGGGGAGAGGCAGGTGCCAGGC
AGAGGGTGGAGAGGAGGCAGGAACATAGCAGCTGGGGCGGGGGCGGGCCTCAAGTGTCATATGCTACTTTCCTGG
GGCCCAGGGGCAAGGACAGGAACAGCCACAGCATGTGTTGGGACAGAGCCCTGTGCCTTCCTAGAGCTGGGCAGGT
GGAATGGGGCAGGAATGGGACTCGTGGTGGCTGCAGCAGGAACTGGAGGGGAAGGGGCTTCTGGATCCTGCAGCC
TACCTTCCTAGAGGCCAGCTTTCCGGGGTCCACCAGGTGGGTGGGAACTGGGCTTGTGTAGCAAGACTGCCCTGAGG
ACCATCCATGACATGGTCTAGATGAAAGTTAGGAAAGAAAGGGAGACAAGCTGGCAGCAGAAGTACAGCTGGGTCA
GGAGCAAGGGCCTTTCCAGATAGGGACAACCCAAGAGTGCACATGTGCCCACGCCACACAACACAGGCACACACGAC
ACGTGCACGCTCATAGGCACTGCACACACACATGCACAGGTGCTCATGCATATGTATGAGCTTCATCTACACACATTCA
CATGCCGTCCTGCTTATGTGCATGTTTCCATACATGCACATGAATGCACAATCACGTGTACACACATGCATGTGATCAC
ATACATGAACATGTGTGCACCCCACTCCTCAGGTGCCATCGGGCTCCTCCTGCTGTCACTGTGCAGCAGGGGACATGA
GGCCCCAGAGCAGACAGGTGCAGCACAGGCGTTCCCAGGCAGTGCCCCACACACATGCATGAGCACACCCGGGCAT
GTGGCGCCTCCTTTGTGGACTCAGTCACCTGCCAGGTGGGCTCCCTGGTGGTGTGAGCTCCCAGAGGTCTGGCGAGA
GAGATAAAGGCAACCCCACCACCAGGCGTGCTGAGAATTCCCTCTTCTGGCTGGGCACAGTGGCTCATACCTGTAATC
CCAGCACTTTGGGAGGCCGAGGTGGGCAGATCACTTGAGGTTAGGAGTTTGAGACCAGCCTGGCCAATATGGTGAA
ACCTCATCTCCACTAAAAATATACACACACAAAAATTAGCTGGGTGTGGTGGTGTGCACCTGTAGTTCCAGCTACTCG
GGAGGCTGAGGCAGGAGAATCGCTTGAACCTGGGAGTCAGAGACTGCAGTGAGCCGAGATCATGTCACTGCACTCC
AGCCCGGGTGACAGAGTGAGACTCCATCTAAAAAAAAAAAAAGAATTCCCTCCTCTGGGAATTTAGACCACAGACAGG
TTGCATGTATGTGGCCGTTGGAGGCAGCACTCACAGCAAAGAGTGGAAACGTCACCACAGGGCCTGCCTTCTGGTGA
AAATGGTGTCCTGCAGGGCGGGCAGCTGTTTGAGGGCAGGTGTCCCAGGTGCGGCCTGCAGCAGCCTGAGGGTCAC
AGAGCGCAGTGCTGGGAGTGCAGAGACTTCCCCCACAGGGAGAGTTCCCAGGAACCTGCTTCCGGTGCACTTCTGGG
GGTTTGAGTTTTTTCCACGGACGAATTACTTTGAGAAACCACTGTTACTCGTGTGTATAG[Y]GTGAGCGTGCGTGTGCAT
GTGTGTTCTGTGTGTGAGTGTGCATGTATGTGCGTGCCTGCGTATATATCCTCGCAGATACGGCTAGGGACCTCACTC
AGGACAGTAGTTCTGCCTGAGGAGAGTGAATGCGGCAAGATTGAGGAGAACACAGGCATCTTCAAACTACATGTGCG
GTGCTTTATTTCTTTAAAAATGCGTCTAAAGCAAATAGGAAAATGTTAAGATTTGAATCCGTAGAGTGTGGGTTCTATT
ATTCTCTCCACATCTTCCATACGTTTAAAATCTTTTGCAATGAAAATAAGCTGTAGTTAAAGCAGCAATGCAGGCTGCC
AGTGAGCGCCCCGGAGGCCAGTGAGGACCAGCATGGCTGGGTGGCCTGTTGGAATCCAAGGGGGGCGGGCAGGAG
CTGCAGGCAGGCGCCCGGGAGTAGCCCGGGCATGGGGGTGCGGGGCAACAGGGATGTCTGCAGGGGTAGCATGTG
GGCCCCGGACTGCAAGCAGGTGGAGCCAGCCGGATGCGGCTCCTATGAGAAAAGCGGGGAACAAGAGACCACGCTC
GTTCTTCCTGCTGCGGGGACAGCCCTGGTCATCGCTCCGGGGAACCCTGCAGCCTGCGCCGCACGTGGCCGCCCCCTG
CTGCTTCCTCCTCCCCGGCCTCCGGGTGGCCTTGCTGACGGCTCCTTCTCTGAGGCAGGTCTCTGCCTTCTCGCCTGGT
GCCTGCACTCAGTAGCCCCCTCACCAGAGCTGCTGGGTGAAGGAAGCACTAAGAACCCAAGGCTCGGGAGGAGAGT
GGGGCCGGGAAGCTGCAGGGAAGCGCAGGGCCAGGCCTGGTGGGCCCAGGGGCTGGCTCACGGGAGGGCAGGAG
GGAGACTGTGGCGGACAGCACGTGGGGCCAGGAGGTGACCTCCAAGTGGATTGTGGGTGGGTTTTTTGTCCTCTTTC
TGCATTTTCCAGGCATTTTGTAATGTGGATAGAATATTTCTGTTCTTCAAAAATACTTTAGTTAAGAAAAATAAGATGG
AAGCTGTTGCACTTGAAAATGAGGAAGCCACTGGTGATGCAGGGGGGGCGGCGGAGAGGACCTCTTCTGCAAATAG
CGGCAGGAACACGGCATGGATGCAGCTCGCGCTCCCCCAGGCCCTCCCCTGGGCTGTGTGGAGGGGTCCGGGGGA

Fig. 14B cont.

ATGGGCCAGCGCCCAGTGGTCACCTGGCCATGTCTCCCCACAG^CCCGGAAGCAGGAGATCATTAAGACCACGGAGC
AGCTCATCGAGGCCGTCAACAACGGTGACTTTGAGGCCTACGC^GT (SEQ ID NO: 125)

Coverage
348
114
PBS
Compound A
Novel exons
KALRN

Fig. 15C

CTCAG$^{Y}$**AATTCAAGATGGATAAGCCGCCTTCAGTCTCAGCCAGGCTGTGCTCTGGGAAACC TGAGGGAACTGGCTCCAGGGTCAGC*TGA*GCCAAGCTGCTCATGTGACCCCTCTCCTCCCAG GCTGCTCACTTGCTCCAGCCCCGGATGATGCTGTGTGTTTTGCTATTTGTGAACCTTGGTC CCCAACAGATGACACAAATGCGTATTGCTGTGCTTGCTCTGTGTGCGTGTGTGTGTGCAC GCGTGCGTGAATCATTGCCAAGGAATTGACACATCACACAAG**$^{Y}$GTAATAC (SEQ ID NO: 126)

Fig. 15D

CCCAG$^{v}$GCTGCTCACTTGCTCCAGCCCCGGATGATGCTGTGTGTTTTGCTATTTGTGAACC
TTGGTCCCCAACAGATGACACAAATGCGTATTGCTGTGCTTGCTCTGTGTGCGTGTGTGT
GTGCACGCGTGCGTGAATCATTGCCAAGGAATTGACACATCACACAAG$^{v}$GTAATAC (SEQ ID NO: 127)

CTTCCAG^vCTGCCTGGGTTTCCTGGAAAGAACTCTTATCCCCAGGAACTAGTTTGTTGAAT AAATGCTGGTGAATGAATGAATGATTGAACAGATGAATGAGTGATGAGTAGATAAAAGG ATGGATGGAGAGATGG^vGTGAGTACA (SEQ ID NO: 128)

(B)

TCCAG^vCCCTAACCACTCAGGATTGGGCCGTTTGTGTCTGGGTATGTCTCTTCCAGCTGCC TGGGTTTCCTGGAAAGAACTCTTATCCCCAGGAACTAGTTTGTTGAATAAATGCTGGTGA ATGAATGAATGATTGAACAGATGAATGAGTGATGAGTAGATAAAAGGATGGATGGAGAG ATGG^vGTGAGTACA (SEQ ID NO: 129)

OLIGONUCLEOTIDES TARGETING RNA BINDING PROTEIN SITES

SEQUENCE LISTING

The instant application contains a Sequence Listing which has been submitted electronically in ASCII format and is hereby incorporated by reference in its entirety. Said ASCII copy, created on Jul. 21, 2021, is named 51551-008001_Sequence_Listing_7_21_21_ST25 and is 45,306 bytes in size.

The present invention relates to antisense oligonucleotides which are complementary, such as fully complementary, to RNA binding protein target sites on multiple RNAs, such as TDP-43 binding sites on multiple RNA transcripts, and are capable of restoring RNA binding protein functionality to the multiple RNA transcript, such as for use in conditions and medical indications where the RNA binding protein is functionally depleted.

BACKGROUND

TAR DNA binding protein 43 (TDP-43) is a versatile RNA/DNA binding protein involved in RNA-related metabolism. Dysregulation of TDP-43 deposits act as inclusion bodies in the brain and spinal cord of patients with the motor neuron diseases: amyotrophic lateral sclerosis (ALS) and frontotemporal lobar degeneration (FTLD) (Prasad et al., Front. Mol. Neurosci., 2019).

TDP-43 is predominantly localized in the nucleus but also shuttles to the cytoplasm for some of its functions (Ayala et al., 2008). In disease, such as in ALS and FTLD, there is an increase in the cytoplasmic TDP-43 concentration leading to cytoplasmic inclusion formation (Neumann et al., 2006; Winton et al., 2008a). The cytoplasmic mis-localization can be associated with nuclear depletion, resulting in a reduction or loss of TDP-43 function. There are TDP-43 mutations which result in aberrant splicing of TDP-43 target RNAs, resulting in widespread splicing aberration (see for example Arnold et al., PNAS 2013 110 E736—745 and Yang et al., PNAS. U.S.A. 111, E1121-E1129).

Klim et al., reports that STMN2 loss upon reduced TDP-43 function is due to altered STMN2 splicing, and suggests restoring STMN2 as a therapeutic strategy for ALS.

TDP-43 depletion is indicated in a range of diseases, referred to as TDP-43 pathologies, and including for example diseases such as amyotrophic lateral sclerosis (ALS), frontotemporal lobar degeneration (FTLD), Progressive supranuclear palsy (PSP), Primary lateral sclerosis, Progressive muscular atrophy, Alzheimer's disease, Parkinson's disease, autism, Hippocampal sclerosis dementia, Down syndrome, Huntington's disease, polyglutamine diseases, such as spinocerebellar ataxia 3, myopathies and Chronic Traumatic Encephalopathy.

Tollervey et al., Nature Neuroscience 2010, 452-458 reports on the characterization of the RNA targets and position dependent splicing regulation of TDP-43 in healthy brain tissue and brain tissue from FTLD patients. Most TDP-43 binding sites mapped to introns, long non-coding RNAs (lncRNA) and intergenic transcripts, which were enriched for UG-rich motifs. The conserved RNP segments in TDP-43 are involved in binding to TAR DNA sequences and RNA sequences with UG-repeats (Ayala et al., J. Mol. Biol. 2005; 348:575-588). TDP-43 depletion in cells, such as in TDP-pathologies is correlated to the loss of RNA binding of TDP-43 to TDP-43 RNA targets.

TDP-43 binding sites in human RNAs are available on line from the A database of RNA binding proteins and associated motifs—see attract.cnic.es/results/e9f29380-8921-406e-84a8-27ce9b9398b4. Certain characterized human RNA TDP-43 binding sites disclosed include the following RNA sequences: GUGAAUGA, GUUGUGC, UGUGUGUGUGUG (SEQ ID NO: 20), GAAUGG, UGUGUGUG, GAAUGA, UGUGUG, GUUGUUC, and GUUUUGC.

Melamed et al., reports on premature polyadenylation-mediated loss of STMN2 as a hallmark of TDP-43 neurodegeneration. WO2019/241648 discloses 2'O-methoxyethyl ASOs for increasing STMN2 expression.

The present inventors have identified antisense oligonucleotides which are complementary, such as fully complementary to TDP-43 nucleic acid binding sites and are capable of restoring the processing or regulation of TDP-43 RNA transcripts targets, e.g. the expression and splicing of RNA transcripts, that are dysregulated in cells showing TDP-43 loss of function, and thereby provides a novel approach to restore TDP-43 functionality in TDP-43 depleted cells (i.e. cells with a loss of TDP-43 function), as well as a novel therapeutic approach for the treatment of TDP-43 pathologies.

OBJECTIVE OF THE INVENTION

The present invention relates to antisense oligonucleotides which are complementary to conserved TDP-43 binding sites on pre-mRNA transcripts, which are capable of restoring RNA binding protein function in the processing of multiple independent mRNAs in TDP-43 depleted cells.

The present invention provides oligonucleotides for restoring RNA binding protein functionality, such as TDP-43 functionality, or TDP-43 like functionality, in cells which have a reduced level of functioning TDP-43.

The present invention provides oligonucleotide which are capable of restoring the nuclear function of TDP-43 in the RNA processing or expression of one or more TDP-43 target RNAs, and thereby restore, at least partially, or enhance, the functional phenotype of the TDP-43 target RNA(s). Such oligonucleotide compounds are referred to herein as RNA binding protein mimics, such as TDP-43 mimics.

The present invention provides antisense oligonucleotides which are complementary to TDP-43 binding sites, and their use in therapy, such as for the treatment of TDP-43 pathologies.

The present invention further provides oligonucleotides which are complementary to TDP-43 binding sites on multiple RNA transcripts, i.e. RNA transcripts which are transcribed from distinct genetic loci. The multiple RNA transcripts may, for example, be independently selected from the group consisting of pre-mRNAs, mRNAs, and lncRNA.

SUMMARY OF INVENTION

The invention provides an antisense oligonucleotide of 8 to 40 nucleotides in length, which comprises a contiguous nucleotide sequence of at least 8 nucleotides in length which is complementary to, such as fully complementarity, a sequence selected from the group consisting of (5'-3') (UG)n, (GU)n, wherein n is 4-20, UGUGUGUG, UGUGUGUGU, UGUGUGUGUG (SEQ ID NO: 37), UGUGUGUGUGU (SEQ ID NO: 38), UGUGUGUGUGUG (SEQ ID NO: 35), UGUGUGUGUGUGU (SEQ ID NO: 39), GUGUGUGU, GUGUGUGUG, GUGUGUGUGU (SEQ ID NO: 40), GUGUGUGUGUG (SEQ ID NO: 41), GUGUGUGU- GUGU (SEQ ID NO: 42), GUGUGUGUGUGUG (SEQ ID NO: 43), and GUGAAUGA, wherein the antisense oligonucleotide is capable of restoring the functional phenotype of one or more TDP-43 target RNA(s) in a cell which is TDP-43 depleted, such as a cell which is expressing aberrant TDP-43 protein; or a pharmaceutically acceptable salt thereof.

The contiguous nucleotide sequence may comprise one or more modified nucleosides.

As explained in the background section, functional TDP-43 is primarily a nuclear localized protein, which may exist in the cytoplasm. However, aggregation of TDP-43 in the cytoplasm, what are referred to as cytoplasmic inclusions (also referred to as aberrant TDP-43), is associated with non-functional TDP-43, and this is associated with a loss of nuclear TDP-43 functionality for example in the processing of numerous pre-mRNAs. Cells which express TDP-43 in cytoplasmic inclusions are therefore to be considered TDP-43 depleted.

The antisense oligonucleotide may be an isolated antisense oligonucleotide or a purified oligonucleotide. The antisense oligonucleotide of the invention is a manufactured (man-made) antisense oligonucleotide.

The functional phenotype may for example be RNA processing events which are modulated by or dependent upon functional TDP-43 (i.e. non-aberrant TDP-43, typically nuclear TDP-43), and/or whose fidelity is dependent upon functional TDP-43. The enhancement of TDP-43 functionality by use of the antisense oligonucleotides of the invention may therefore be evaluated by assessing the fidelity of RNA processing events which are modulated by or dependent upon functional TDP-43, as for example illustrated herein, with reference to the STMN2, ARHGAP32, SLC5A7, CERT1, CAMK2B, KALRN and UNC13A RNA processing.

The invention provides for an antisense oligonucleotide, of 8 to 40 nucleotides in length, which comprises a contiguous nucleotide sequence of at least 8 nucleotides in length with at least 75% complementarity, such as at least 90% complementarity or 100% complementarity, to a sequence selected from the group consisting of (5'-3') (UG)n, (GU)n, wherein n is 4-20, UGUGUGUG, UGUGUGUGU, UGUGUGUGUG (SEQ ID NO: 37), UGUGUGUGUGU(SEQ ID NO: 38), UGUGUGUGUGUG(SEQ ID NO: 35), UGUGUGUGUGUGU(SEQ ID NO: 39), GUGUGUGU, GUGUGUGUG, GUGUGUGUGU(SEQ ID NO: 40), GUGUGUGUGUGU(SEQ ID NO: 42), GUGUGUGUGUGUG(SEQ ID NO: 43), and GUGAAUGA, or a pharmaceutically acceptable salt thereof, for use in medicine.

The contiguous nucleotide sequence may comprise one or more modified nucleosides.

The invention provides for an antisense oligonucleotide, of 8 to 40 nucleotides in length, which comprises a contiguous nucleotide sequence of at least 8 nucleotides in length with at least 75% complementarity, such as at least 90% complementarity or 100% complementarity to a sequence selected from the group consisting of (5'-3') (UG)n, (GU)n, wherein n is 4-20, UGUGUGUG, UGUGUGUGU, UGUGUGUGUG (SEQ ID NO: 37), UGUGUGUGUGU(SEQ ID NO: 38), UGUGUGUGUGUG(SEQ ID NO: 35), UGUGUGUGUGUGU(SEQ ID NO: 39), GUGUGUGU, GUGUGUGUG, GUGUGUGUGU(SEQ ID NO: 40), GUGUGUGUGUGU(SEQ ID NO: 42), GUGUGUGUGUGUG(SEQ ID NO: 43), and GUGAAUGA, or a pharmaceutically acceptable salt thereof, for use in the treatment of a disease characterized by TDP-43 pathology.

The contiguous nucleotide sequence may comprise one or more modified nucleosides.

Advantageously, the antisense oligonucleotide or contiguous nucleotide sequence thereof comprises at least 12 or at least 13 contiguous nucleotides, which are complementary, such as fully complementary, to the sequence UGUGUGUGUGUG (SEQ ID NO: 35), or GUGUGUGUGUGU (SEQ ID NO: 42), or UGUGUGUGUGUGU (SEQ ID NO: 39), or GUGUGUGUGUGUG (SEQ ID NO: 43).

In some embodiments, the antisense oligonucleotide or contiguous nucleotide sequence comprises at least 14 contiguous nucleotides which are complementary, such as fully complementary, to the sequence UGUGUGUGUGUGUG (SEQ ID NO: 46), or GUGUGUGUGUGUGU (SEQ ID NO: 47).

In some embodiments, the antisense oligonucleotide or contiguous nucleotide sequence comprises at least 18 contiguous nucleotides which are complementary, such as fully complementary, to the sequence (UG)n or (GU)n, wherein n is an integer 6-20, such as 7-9.

In some embodiments, the antisense oligonucleotide or contiguous nucleotide sequence comprises at least 18 contiguous nucleotides which are complementary, such as fully complementary, to the sequence UGUGUGUGUGUGUGUGUG (SEQ ID NO: 48), or GUGUGUGUGUGUGUGUGU (SEQ ID NO: 49).

In some embodiments, the antisense oligonucleotide according to the invention, or the contiguous nucleotide sequence thereof comprises the sequence CACACACA or ACACACAC.

In some embodiments, the antisense oligonucleotide according to the invention, or the contiguous nucleotide sequence thereof comprises the sequence CACACACACACA (SEQ ID NO: 14) or ACACACACACAC (SEQ ID NO: 5).

In some embodiments, the antisense oligonucleotide according to the invention, or the contiguous nucleotide sequence thereof comprises the sequence CACACACACACAC (SEQ ID NO: 15) or ACACACACACACA (SEQ ID NO: 6).

In some embodiments, the antisense oligonucleotide according to the invention, or the contiguous nucleotide sequence thereof comprises the sequence CACACACACACACACA (SEQ ID NO: 16) or ACACACACACACACAC (SEQ ID NO: 7).

In some embodiments, the antisense oligonucleotide according to the invention, or the contiguous nucleotide sequence thereof comprises the sequence (SEQ ID NO: 20).

In some embodiments, the antisense oligonucleotide according to the invention, or the contiguous nucleotide sequence thereof comprises the sequence (SEQ ID NO: 21).

In some embodiments, the antisense oligonucleotide according to the invention, or the contiguous nucleotide sequence thereof comprises the sequence (SEQ ID NO: 22).

In some embodiments, the antisense oligonucleotide according to the invention, or the contiguous nucleotide sequence thereof comprises the sequence (SEQ ID NO: 23).

In some embodiments, the antisense oligonucleotide according to the invention, or the contiguous nucleotide sequence thereof comprises the sequence (SEQ ID NO: 24).

In some embodiments, the antisense oligonucleotide according to the invention, or the contiguous nucleotide sequence thereof comprises the sequence (SEQ ID NO: 25).

In some embodiments, the antisense oligonucleotide according to the invention, or the contiguous nucleotide sequence thereof comprises the sequence (SEQ ID NO: 26).

In some embodiments, the antisense oligonucleotide according to the invention, or the contiguous nucleotide sequence thereof comprises the sequence (SEQ ID NO: 27).

In some embodiments, the antisense oligonucleotide according to the invention, or the contiguous nucleotide sequence thereof comprises the sequence (SEQ ID NO: 28).

In some embodiments, the antisense oligonucleotide according to the invention, or the contiguous nucleotide sequence thereof comprises the sequence (SEQ ID NO: 29).

In some embodiments, the antisense oligonucleotide according to the invention, or the contiguous nucleotide sequence thereof comprises the sequence (SEQ ID NO: 30).

In some embodiments, the antisense oligonucleotide according to the invention, or the contiguous nucleotide sequence thereof comprises the sequence (SEQ ID NO: 31).

In some embodiments, the antisense oligonucleotide according to the invention, or the contiguous nucleotide sequence thereof comprises the sequence (SEQ ID NO: 32).

In some embodiments, the antisense oligonucleotide according to the invention, or the contiguous nucleotide sequence thereof comprises the sequence (SEQ ID NO: 33).

In some embodiments, the antisense oligonucleotide according to the invention, or the contiguous nucleotide sequence thereof comprises the sequence (SEQ ID NO: 34).

In some embodiments, the antisense oligonucleotide according to the invention, or the contiguous nucleotide sequence thereof comprises the sequence (SEQ ID NO: 50).

In some embodiments, the antisense oligonucleotide according to the invention, or the contiguous nucleotide sequence thereof comprises the sequence (SEQ ID NO: 51).

In some embodiments, the antisense oligonucleotide according to the invention, or the contiguous nucleotide sequence thereof comprises the sequence (SEQ ID NO: 52).

In some embodiments, the antisense oligonucleotide according to the invention, or the contiguous nucleotide sequence thereof comprises the sequence (SEQ ID NO: 53).

In some embodiments, the antisense oligonucleotide according to the invention, or the contiguous nucleotide sequence thereof comprises the sequence (SEQ ID NO: 54).

In some embodiments, the antisense oligonucleotide according to the invention, or the contiguous nucleotide sequence thereof comprises the sequence (SEQ ID NO: 55).

In some embodiments, the antisense oligonucleotide according to the invention, or the contiguous nucleotide sequence thereof comprises the sequence (SEQ ID NO: 56).

In some embodiments, the antisense oligonucleotide according to the invention, or the contiguous nucleotide sequence thereof comprises the sequence (SEQ ID NO: 57).

In some embodiments, the antisense oligonucleotide according to the invention, or the contiguous nucleotide sequence thereof comprises the sequence (SEQ ID NO: 58).

In some embodiments, the antisense oligonucleotide according to the invention, or the contiguous nucleotide sequence thereof comprises the sequence (SEQ ID NO: 59).

In some embodiments, the antisense oligonucleotide according to the invention, or the contiguous nucleotide sequence thereof comprises the sequence (SEQ ID NO: 60).

In some embodiments, the antisense oligonucleotide according to the invention, or the contiguous nucleotide sequence thereof comprises the sequence (SEQ ID NO: 61).

In some embodiments, the antisense oligonucleotide according to the invention, or the contiguous nucleotide sequence thereof comprises the sequence (SEQ ID NO: 62).

In some embodiments, the antisense oligonucleotide according to the invention, or the contiguous nucleotide sequence thereof comprises the sequence (SEQ ID NO: 63).

In some embodiments, the antisense oligonucleotide according to the invention, or the contiguous nucleotide sequence thereof comprises the sequence (SEQ ID NO: 64).

In some embodiments, the antisense oligonucleotide according to the invention, or the contiguous nucleotide sequence thereof comprises the sequence (SEQ ID NO: 65).

In some embodiments, the antisense oligonucleotide according to the invention, or the contiguous nucleotide sequence thereof comprises the sequence (SEQ ID NO: 66).

In some embodiments, the antisense oligonucleotide according to the invention, or the contiguous nucleotide sequence thereof comprises the sequence (SEQ ID NO: 67).

In some embodiments, the antisense oligonucleotide according to the invention, or the contiguous nucleotide sequence thereof comprises the sequence (SEQ ID NO: 68).

In some embodiments, the antisense oligonucleotide according to the invention, or the contiguous nucleotide sequence thereof comprises the sequence (SEQ ID NO: 69).

In some embodiments, the antisense oligonucleotide according to the invention, or the contiguous nucleotide sequence thereof comprises the sequence (SEQ ID NO: 70).

In some embodiments, the antisense oligonucleotide according to the invention, or the contiguous nucleotide sequence thereof comprises the sequence (SEQ ID NO: 71).

In some embodiments, the antisense oligonucleotide according to the invention, or the contiguous nucleotide sequence thereof comprises the sequence (SEQ ID NO: 72).

In some embodiments, the antisense oligonucleotide according to the invention, or the contiguous nucleotide sequence thereof comprises the sequence (SEQ ID NO: 73).

In some embodiments, the antisense oligonucleotide according to the invention, or the contiguous nucleotide sequence thereof comprises the sequence (SEQ ID NO: 74).

In some embodiments, the antisense oligonucleotide according to the invention, or the contiguous nucleotide sequence thereof comprises the sequence (SEQ ID NO: 75).

In some embodiments, the antisense oligonucleotide according to the invention, or the contiguous nucleotide sequence thereof comprises the sequence (SEQ ID NO: 76).

In some embodiments, the antisense oligonucleotide according to the invention, or the contiguous nucleotide sequence thereof comprises the sequence (SEQ ID NO: 77).

In some embodiments, the antisense oligonucleotide according to the invention, or the contiguous nucleotide sequence thereof comprises the sequence (SEQ ID NO: 78).

In some embodiments, the antisense oligonucleotide according to the invention, or the contiguous nucleotide sequence thereof comprises the sequence (SEQ ID NO: 79).

In some embodiments, the antisense oligonucleotide according to the invention, or the contiguous nucleotide sequence thereof comprises the sequence (SEQ ID NO: 80).

In some embodiments, the antisense oligonucleotide according to the invention, or the contiguous nucleotide sequence thereof comprises the sequence (SEQ ID NO: 81).

In some embodiments, the antisense oligonucleotide according to the invention, or the contiguous nucleotide sequence thereof comprises the sequence (SEQ ID NO: 82).

In some embodiments, the antisense oligonucleotide according to the invention, or the contiguous nucleotide sequence thereof comprises the sequence (SEQ ID NO: 83).

In some embodiments, the antisense oligonucleotide according to the invention, or the contiguous nucleotide sequence thereof comprises the sequence (SEQ ID NO: 84).

In some embodiments, the antisense oligonucleotide according to the invention, or the contiguous nucleotide sequence thereof comprises the sequence (SEQ ID NO: 85).

In some embodiments, the antisense oligonucleotide according to the invention, or the contiguous nucleotide sequence thereof comprises the sequence (SEQ ID NO: 86).

In some embodiments, the antisense oligonucleotide according to the invention, or the contiguous nucleotide sequence thereof comprises the sequence (SEQ ID NO: 87).

In some embodiments, the antisense oligonucleotide according to the invention, or the contiguous nucleotide sequence thereof comprises the sequence (SEQ ID NO: 88).

In some embodiments, the antisense oligonucleotide according to the invention, or the contiguous nucleotide sequence thereof comprises the sequence (SEQ ID NO: 89).

In some embodiments, the antisense oligonucleotide according to the invention, or the contiguous nucleotide sequence thereof comprises the sequence (SEQ ID NO: 90).

In some embodiments, the antisense oligonucleotide according to the invention, or the contiguous nucleotide sequence thereof comprises the sequence (SEQ ID NO: 91).

In some embodiments, the antisense oligonucleotide according to the invention, or the contiguous nucleotide sequence thereof comprises the sequence (SEQ ID NO: 92).

In some embodiments, the antisense oligonucleotide according to the invention, or the contiguous nucleotide sequence thereof comprises the sequence (SEQ ID NO: 93).

In some embodiments, the antisense oligonucleotide according to the invention, or the contiguous nucleotide sequence thereof comprises the sequence (SEQ ID NO: 94).

In some embodiments, the antisense oligonucleotide according to the invention, or the contiguous nucleotide sequence thereof comprises the sequence (SEQ ID NO: 95).

In some embodiments, the antisense oligonucleotide according to the invention, or the contiguous nucleotide sequence thereof comprises the sequence (SEQ ID NO: 96).

In some embodiments, the antisense oligonucleotide according to the invention, or the contiguous nucleotide sequence thereof comprises the sequence (SEQ ID NO: 97).

In some embodiments, the antisense oligonucleotide according to the invention, or the contiguous nucleotide sequence thereof comprises the sequence (SEQ ID NO: 98).

In some embodiments, the antisense oligonucleotide according to the invention, or the contiguous nucleotide sequence thereof comprises the sequence (SEQ ID NO: 99).

In some embodiments, the antisense oligonucleotide according to the invention, or the contiguous nucleotide sequence thereof comprises the sequence (SEQ ID NO: 100).

In some embodiments, the antisense oligonucleotide according to the invention, or the contiguous nucleotide sequence thereof comprises the sequence (SEQ ID NO: 101).

In some embodiments, the antisense oligonucleotide according to the invention, or the contiguous nucleotide sequence thereof comprises the sequence (SEQ ID NO: 102).

In some embodiments, the antisense oligonucleotide according to the invention, or the contiguous nucleotide sequence thereof comprises the sequence (SEQ ID NO: 103).

In some embodiments, the antisense oligonucleotide according to the invention, or the contiguous nucleotide sequence thereof comprises the sequence (CA)n or (AC)n, wherein n is an integer 6-20, such as 7-9.

In some embodiments, the antisense oligonucleotide according to the invention, or the contiguous nucleotide sequence thereof comprises a sequence selected from the group consisting of SEQ ID NO: 1-18 or a sequence selected from SEQ ID NOs 1-34 and SEQ ID NOs 50-103.

In some embodiments, the antisense oligonucleotide according to the invention, or the contiguous nucleotide sequence thereof, consists of a sequence selected from the group consisting of SEQ ID NO: 1-18 or a sequence selected from SEQ ID NOs 1-34 and SEQ ID NOs 50-103.

The invention provides an antisense oligonucleotide selected from the group consisting of compound ID No #1-18, or a pharmaceutically acceptable salt thereof. The oligonucleotide of the invention may therefore be an antisense oligonucleotide selected from the group consisting of compound ID No #1-18, or a pharmaceutically acceptable salt thereof.

In some embodiments, the antisense oligonucleotide according to the invention has a length of at least 12 or at least 13 nucleotides.

In some embodiments, the contiguous nucleotide sequence of the antisense oligonucleotide is at least 12 nucleotides in length.

In some embodiments the antisense oligonucleotide or contiguous nucleotide sequence thereof according to any aspect of the invention has a length of at least 12 contiguous nucleotides.

In some embodiments the antisense oligonucleotide or contiguous nucleotide sequence thereof according to any aspect of the invention has a length of at least 13 contiguous nucleotides.

In some embodiments the antisense oligonucleotide or contiguous nucleotide sequence thereof according to any aspect of the invention has a length of at least 14 contiguous nucleotides.

In some embodiments the antisense oligonucleotide or contiguous nucleotide sequence thereof according to any aspect of the invention has a length of at least 15 contiguous nucleotides.

In some embodiments the antisense oligonucleotide or contiguous nucleotide sequence thereof according to any aspect of the invention has a length of at least 16 contiguous nucleotides.

In some embodiments the antisense oligonucleotide or contiguous nucleotide sequence thereof according to any aspect of the invention has a length of at least 17 contiguous nucleotides.

In some embodiments the antisense oligonucleotide or contiguous nucleotide sequence thereof according to any aspect of the invention has a length of at least 18 contiguous nucleotides.

In some embodiments the antisense oligonucleotide or contiguous nucleotide sequence thereof according to any aspect of the invention has a length of at least 19 contiguous nucleotides.

In some embodiments the antisense oligonucleotide or contiguous nucleotide sequence thereof according to any aspect of the invention has a length of at least 20 contiguous nucleotides.

In some embodiments the antisense oligonucleotide or contiguous nucleotide sequence thereof according to any aspect of the invention has a length of at least 21 contiguous nucleotides.

In some embodiments the antisense oligonucleotide or contiguous nucleotide sequence thereof according to any aspect of the invention has a length of at least 22 contiguous nucleotides.

In some embodiments the antisense oligonucleotide or contiguous nucleotide sequence thereof according to any aspect of the invention has a length of at least 23 contiguous nucleotides.

In some embodiments the antisense oligonucleotide or contiguous nucleotide sequence thereof according to any aspect of the invention has a length of at least 24 contiguous nucleotides.

In some embodiments the antisense oligonucleotide or contiguous nucleotide sequence thereof according to any aspect of the invention has a length of at least 25 contiguous nucleotides.

In some embodiments the antisense oligonucleotide or contiguous nucleotide sequence thereof according to any aspect of the invention has a length of at least 26 contiguous nucleotides.

In some embodiments the antisense oligonucleotide or contiguous nucleotide sequence thereof according to any aspect of the invention has a length of at least 27 contiguous nucleotides.

In some embodiments the antisense oligonucleotide or contiguous nucleotide sequence thereof according to any aspect of the invention has a length of at least 28 contiguous nucleotides.

In some embodiments the antisense oligonucleotide or contiguous nucleotide sequence thereof according to any aspect of the invention has a length of at least 29 contiguous nucleotides.

In some embodiments the antisense oligonucleotide or contiguous nucleotide sequence thereof according to any aspect of the invention has a length of at least 30 contiguous nucleotides.

In some embodiments the antisense oligonucleotide or contiguous nucleotide sequence thereof according to any aspect of the invention has a length of at least 31 contiguous nucleotides.

In some embodiments the antisense oligonucleotide or contiguous nucleotide sequence thereof according to any aspect of the invention has a length of at least 32 contiguous nucleotides.

In some embodiments, the antisense oligonucleotide according to the invention has a Gibbs free energy of the antisense oligonucleotide to a complementary target RNA, of lower than about $-10\Delta G$, such as lower than about $-15$ AG, such as lower than about $-17$ $\Delta G$. Advantageously, the contiguous nucleotide sequence of such antisense oligonucleotides is at least 12, such as at least 13 nucleotides in length.

Advantageously the antisense oligonucleotide of the invention may comprise one or more modified nucleosides.

Advantageously the antisense oligonucleotide of the invention may comprise LNA nucleosides. LNA nucleotides within the contiguous nucleotide sequence are further advantageous. In some embodiments, the antisense oligonucleotide of the invention may comprise LNA nucleosides and non-LNA nucleosides, such as DNA nucleosides. In some embodiments, the antisense oligonucleotide, or contiguous nucleotide sequence thereof, may comprise LNA and DNA nucleosides. In some embodiments, all of the nucleosides of the antisense oligonucleotide, or contiguous nucleotide sequence thereof, are independently selected from LNA and DNA nucleosides. Advantageously, the length of contiguous DNA nucleosides present within the antisense oligonucleotide, or contiguous nucleotide sequence thereof, is limited so as to prevent RNaseH recruitment which results in target RNA degradation. Suitably the antisense oligonucleotide or contiguous nucleotide sequence thereof does not comprise more than four contiguous DNA nucleosides, more advantageously does not comprise more than 3 contiguous DNA nucleosides.

When used, advantageously, the antisense oligonucleotide according to the invention is capable of modulating the splicing of two or more TDP-43 target pre-mRNAs (target RNAs). By way of example, the two or more TDP-43 target RNAs may be independently selected from the group consisting of STMN2 pre-mRNA, ARHGAP32 pre-mRNA, SLC5A7 pre-mRNA, CERT1 pre-mRNA, CAMK2B pre-mRNA, KALRN pre-mRNA and UNC13A pre-mRNA.

In some embodiments the antisense oligonucleotide according to the invention is capable of modulating the splicing of two or more TDP-43 target pre-mRNAs (target RNAs).

In some embodiments the antisense oligonucleotide according to the invention is capable of modulating the splicing of three or more TDP-43 target pre-mRNAs (target RNAs).

In some embodiments the antisense oligonucleotide according to the invention is capable of modulating the splicing of four or more TDP-43 target pre-mRNAs (target RNAs).

In some embodiments the antisense oligonucleotide according to the invention is capable of modulating the splicing of two, three, four, five, six, seven, eight, nine, ten or more TDP-43 target pre-mRNAs (target RNAs).

In some embodiments, the antisense oligonucleotide is capable of enhancing the expression of STMN2 (wild type), and is further capable of enhancing the fidelity of pre-mRNA splicing of at least one, such as two or more pre-mRNAs selected from the group consisting of ARHGAP32 pre-mRNA, SLC5A7 pre-mRNA, CERT1 pre-mRNA, CAMK2B pre-mRNA, KALRN pre-mRNA and UNC13A pre-mRNA, when administered to a TDP-43 depleted cell. In some embodiments, the two or more selected pre-mRNAs are selected from the groups consisting of STMN2 and ARHGAP32; STMN2 and SLC5A7; STMN2 and CERT1; ARHGAP32 and SLC5A7; ARHGAP32 and CERT1; and SLC5A7 and CERT1.

In some embodiments, the antisense oligonucleotide is capable of enhancing the fidelity of pre-mRNA splicing of two or more pre-mRNAs selected from the group consisting of STMN2 pre-mRNA, ARHGAP32 pre-mRNA, SLC5A7 pre-mRNA, CERT1 pre-mRNA, CAMK2B pre-mRNA, KALRN pre-mRNA and UNC13A pre-mRNA, when administered to a TDP-43 depleted cell. In some embodiments, the two or more selected pre-mRNAs are selected from the groups consisting of STMN2 and ARHGAP32; STMN2 and SLC5A7; STMN2 and CERT1; ARHGAP32 and SLC5A7; ARHGAP32 and CERT1; and SLC5A7 and CERT1.

In some embodiments, the antisense oligonucleotide is capable of enhancing the fidelity of pre-mRNA splicing of three or more pre-mRNAs selected from the group consisting of STMN2 pre-mRNA, ARHGAP32 pre-mRNA, SLC5A7 pre-mRNA, CERT1 pre-mRNA, CAMK2B pre-mRNA, KALRN pre-mRNA and UNC13A pre-mRNA when administered to a TDP-43 depleted cell.

In some embodiments, the two or more selected pre-mRNAs are selected from the groups consisting of STMN2 and ARHGAP32; STMN2 and SLC5A7; and STMN2 and CERT1 pre-mRNA.

In some embodiments, the antisense oligonucleotide is capable of enhancing the fidelity of pre-mRNA splicing of STMN2 pre-mRNA, ARHGAP32 pre-mRNA, SLC5A7 pre-mRNA, CERT1 pre-mRNA, CAMK2B pre-mRNA, KALRN pre-mRNA and UNC13A pre-mRNA when administered to a TDP-43 depleted cell.

In some embodiments, the antisense oligonucleotide is capable of increasing the expression of STMN2 when administered to a TDP-43 depleted cell which is expressing STMN2 pre-mRNA.

In some embodiments, the antisense oligonucleotide is capable of decreasing the proportion of STMN2 mature mRNAs which comprise a cryptic exon (ce1) between exon 1 and exon 2, as compared to the wildtype STMN2 mature mRNA with a contiguous exon1/exon2 junction, when administered to a TDP-43 depleted cell which is expressing STMN2 pre-mRNA.

In some embodiments, the antisense oligonucleotide is capable of decreasing the level of aberrantly spliced ARHGAP32 mature mRNA, when administered to a TDP-43 depleted cell which is expressing ARHGAP32 pre-mRNA.

In some embodiments, the antisense oligonucleotide is capable of decreasing the level of aberrant exon inclusion in SLC5A7 mRNA transcript, when administered to a TDP-43 depleted cell which is expressing SLC5A7 pre-mRNA.

In some embodiments, the antisense oligonucleotide is capable of decreasing the level of aberrant exon inclusion in CERT1 mRNA transcript, when administered to a TDP-43 depleted cell which is expressing CERT1 pre-mRNA.

In some embodiments, the antisense oligonucleotide is capable of decreasing the level of aberrant exon inclusion in CAMK2B mRNA transcript, when administered to a TDP-43 depleted cell which is expressing CAMK2B pre-mRNA.

In some embodiments, the antisense oligonucleotide is capable of decreasing the level of aberrant exon inclusion in KALRN mRNA transcript, when administered to a TDP-43 depleted cell which is expressing KALRN pre-mRNA.

In some embodiments, the antisense oligonucleotide is capable of decreasing the level of aberrant exon inclusion in UNC13A mRNA transcript, when administered to a TDP-43 depleted cell which is expressing UNC13A pre-mRNA.

In some embodiments, the antisense oligonucleotide is capable of correcting the aberrant splicing of two or more of STMN2, CERT1, SLC5A7, ARHGAP32, CAMK2B, KALRN and UNC13A pre-mRNA in a TDP-43 depleted cell.

In some embodiments, the antisense oligonucleotide does not comprise a region of more than 3, or more than 4, contiguous DNA nucleosides.

In some embodiments, the antisense oligonucleotide, is not capable of mediating RNAseH cleavage.

In some embodiments, the antisense oligonucleotide is a morpholino antisense oligonucleotide.

In some embodiments, the antisense oligonucleotide, or contiguous nucleotide sequence thereof, comprises one or more affinity enhancing nucleosides, such as 2'sugar modified nucleosides which enhance the binding affinity between the antisense oligonucleotide and a complementary RNA molecule, for example and advantageously, to provide a lower Gibbs free energy, such as a Gibbs free energy lower −10, such as lower than −15.

In some embodiments, the antisense oligonucleotide or contiguous nucleotide sequence thereof, comprises one or more modified nucleosides, such as one or more affinity enhancing 2' sugar modified nucleoside, such as a 2' sugar modified nucleoside independently selected from the group consisting of: 2'-O-alkyl-RNA; 2'-O-methyl RNA (2'-OMe); 2'-alkoxy-RNA; 2'-O-methoxyethyl-RNA (2'-MOE); 2'-amino-DNA; 2'-fluro-RNA; 2'-fluoro-DNA; arabino nucleic acid (ANA); 2'-fluoro-ANA; locked nucleic acid (LNA), or a combination thereof.

In some embodiments the antisense oligonucleotide, or contiguous nucleotide sequence thereof, comprises 2'-O-methoxyethyl-RNA (2'-MOE) nucleosides. In some embodiments, all the nucleosides in the antisense oligonucleotide, or contiguous nucleotide sequence thereof, are 2'-O-methoxyethyl-RNA (2'-MOE) nucleosides, optionally linked by phosphorothioate internucleoside linkages.

In some embodiments the antisense oligonucleotide, or contiguous nucleotide sequence thereof, comprises 2'-O-methy nucleosides. In some embodiments, all the nucleosides in the antisense oligonucleotide, or contiguous nucleotide sequence thereof, are 2'-O-methy nucleosides, optionally linked by phosphorothioate internucleoside linkages.

In some embodiments, one or more of the modified nucleosides within the antisense oligonucleotide, or contiguous nucleotide sequence thereof, is a locked nucleic acid nucleoside (LNA), such as an LNA nucleoside selected from the group consisting of constrained ethyl nucleoside (cEt), or β-D-oxy-LNA.

In some embodiments, the contiguous nucleotide sequence of the antisense oligonucleotide comprises of nucleosides LNA nucleosides and DNA nucleosides, optionally linked by phosphorothioate internucleoside linkages.

In some embodiments, the antisense oligonucleotide or contiguous nucleotide sequence thereof is a mixmer or a totalmer.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103, or at least 8 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 9 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 10 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 11 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 12 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 13 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 14 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 15 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 16 contiguous nucleotides thereof.

In some embodiments, the antisense oligonucleotide or contiguous nucleotide sequence thereof comprises a sequence of nucleobases selected from the group consisting of SEQ ID Nos 1-18, a sequence selected from SEQ ID NOs 1-34 and SEQ ID NOs 50-103 or at least 17 contiguous nucleotides thereof.

In some embodiments, wherein the cytosine bases present in the antisense oligonucleotide or contiguous nucleotide sequence thereof are independently selected from the group consisting of cytosine and 5-methyl cytosine.

In some embodiments, the cytosine bases present in the antisense oligonucleotide or contiguous nucleotide sequence thereof are 5-methyl cytosine.

In some embodiments, the LNA cytosine bases present in the antisense oligonucleotide or contiguous nucleotide sequence thereof are LNA 5-methyl cytosine.

In some embodiments, the LNA cytosine bases present in the antisense oligonucleotide or contiguous nucleotide sequence thereof are LNA 5-methyl cytosine, and DNA cytosine bases are cytosine.

Advantageously, one or more of the internucleoside linkages positioned between the nucleosides on the contiguous nucleotide sequence are modified. In some embodiments, at least about 75%, at least about 80%, at least about 85%, at least about 90%, at least about 95%, or about 100% of the internucleoside linkages positioned between the nucleosides on the contiguous nucleotide sequence are modified.

In some embodiments, one or more, or all of the modified internucleoside linkages are phosphorothioate linkage. In some embodiments, one or more, or all of the linkages within the contiguous nucleotide sequence, are phosphorothioate linkages.

In some embodiments, all of the internucleoside linkages present in the contiguous nucleotide sequence are phosphorothioate internucleoside linkages.

In some embodiments, all of the internucleoside linkages present in the antisense oligonucleotide are phosphorothioate internucleoside linkages.

In some embodiments, the length of the contiguous nucleotide sequence is 8-32 nucleotides.

In some embodiments, the length of the contiguous nucleotide sequence is 8-20 nucleotides.

In some embodiments, the length of the contiguous nucleotide sequence is 12-18 nucleotides.

In some embodiments, the length of the contiguous nucleotide sequence is 13-18 nucleotides.

In some embodiments, the length of the contiguous nucleotide sequence is 14-18 nucleotides.

In some embodiments, the length of the contiguous nucleotide sequence is 10-32 nucleotides.

In some embodiments, the length of the contiguous nucleotide sequence is 20-32 nucleotides.

In some embodiments, the length of the contiguous nucleotide sequence is 21-32 nucleotides.

In some embodiments, the length of the contiguous nucleotide sequence is 22-32 nucleotides.

In some embodiments, the length of the contiguous nucleotide sequence is 23-32 nucleotides.

In some embodiments, the length of the contiguous nucleotide sequence is 24-32 nucleotides.

In some embodiments, the length of the contiguous nucleotide sequence is 25-32 nucleotides.

In some embodiments, the length of the contiguous nucleotide sequence is 26-32 nucleotides.

In some embodiments, the length of the contiguous nucleotide sequence is 27-32 nucleotides.

In some embodiments, the antisense oligonucleotide consists of the contiguous nucleotide sequence.

In some embodiments, the antisense oligonucleotide comprises or consists of an oligonucleotide selected from the group consisting of 16.1, 8.3, 18.3, 18.4, 16.2, 18.2, 7.2, 15.2, 16.3, 15.3, 8.1, 8.2, 7.3, 6.4, 6.3, 18.1, 7.1, 14.2, 6.2, 14.4, 15.4, 10.1, and 15.5.

The invention provides for an antisense oligonucleotide selected from the group consisting of (compound ID #) 16.1, 8.3, 18.3, 18.4, 16.2, 18.2, 7.2, 15.2, 16.3, 15.3, 8.1, 8.2, 7.3, 6.4, 6.3, 18.1, 7.1, 14.2, 6.2, 14.4, 15.4, 10.1, and 15.5.

The oligonucleotide of the invention may comprise one or more conjugate groups, i.e. the oligonucleotide may be an antisense oligonucleotide conjugate.

The invention provides for a conjugate comprising the oligonucleotide according to the invention, and at least one conjugate moiety covalently attached to said oligonucleotide.

The invention provides for a salt, such as a pharmaceutically acceptable salt of the antisense oligonucleotide, or the conjugate, of the invention, such as a sodium salt or a potassium salt.

The invention provides for a pharmaceutical composition comprising the oligonucleotide of claim, or the conjugate of the invention, and a pharmaceutically acceptable diluent, solvent, carrier, salt and/or adjuvant.

The invention provides for a pharmaceutical composition comprising the oligonucleotide of the invention, or the conjugate of the invention, and a pharmaceutically acceptable diluent or solvent, and a cation. The cation may for example be a sodium cation or a potassium cation. The diluent/solvent maybe water.

The invention provides for a method, such as an in vivo or in vitro method, for enhancing TDP-43 functionality in a cell which is expressing aberrant or depleted levels of TDP-43, said method comprising administering an oligonucleotide of the invention or the conjugate according to the invention, or the salt or composition according to the invention, in an effective amount to said cell.

The invention provides for a method for treating or preventing a TDP-43 pathology in a subject comprising administering a therapeutically or prophylactically effective amount of an oligonucleotide of the invention or the conjugate according to the invention, or the salt or composition according to the invention, to a subject suffering from or susceptible to the TDP-43 pathology.

The invention provides for an oligonucleotide of the invention or the conjugate according to the invention, or the salt or composition according to the invention, for use as a medicament.

The invention provides for an oligonucleotide of the invention or the conjugate according to the invention, or the salt or composition according to the invention, for use in the treatment of a TDP-43 pathology.

The invention provides for the use of the oligonucleotide of the invention or the conjugate according to the invention, or the salt or composition according to the invention, for the preparation of a medicament for treatment or prevention of a TDP-43 pathology.

The invention provides for the use or method of the invention, wherein the TDP-43 pathology is a neurological disorder selected from the group consisting of amyotrophic lateral sclerosis (ALS), frontotemporal lobar degeneration (FTLD), Progressive supranuclear palsy (PSP), Primary lateral sclerosis, Progressive muscular atrophy, Alzheimer's disease, Parkinson's disease, Autism, Hippocampal sclerosis dementia, Down syndrome, Huntington's disease, polyglutamine diseases, such as spinocerebellar ataxia 3, myopathies and Chronic Traumatic Encephalopathy.

In some embodiments, the TDP-43 pathology is a neurological disorder selected from the group consisting of amyotrophic lateral sclerosis (ALS), frontotemporal lobar degeneration (FTLD).

The invention provides pharmaceutical compositions comprising the antisense oligonucleotide of the invention and a pharmaceutically acceptable diluents, carriers, salts and/or adjuvants.

The invention provides for a pharmaceutically acceptable salt of the antisense oligonucleotide of the invention. In some embodiments, the pharmaceutically acceptable salt is a sodium salt, a potassium salt or an ammonium salt.

The invention provides for a pharmaceutical solution of the oligonucleotide of the invention, wherein the pharmaceutical solution comprises the oligonucleotide of the invention and a pharmaceutically acceptable solvent, such as phosphate buffered saline.

The invention provides for the oligonucleotide of the invention in solid powdered form, such as in the form of a lyophilized powder.

Typically, the antisense oligonucleotide of the invention comprises a contiguous nucleotide sequence of at least 8 or at least 10 nucleotides in length, such as 10-32, 15-32, 20-32, 21-32, 22-32, 23-32, 24-32, 25-32, 26-32, 27-32 or 10-20 nucleotides in length, wherein the contiguous nucleotide sequence is at least 75% complementary, such as at least 90% complementary to or fully complementary to a TDP-43 RNA binding sequence. In some embodiments, all of the nucleosides of the antisense oligonucleotide form the contiguous nucleotide sequence.

In some embodiments, the antisense oligonucleotide of the invention is capable of modulating the splicing of the at least two human pre-mRNAs. For example, the splicing of human STMN2, CERT1, SLC5A7, ARHGAP32, CAMK2B, KALRN and UNC13A pre-mRNAs are dependent upon TDP-43 binding, as illustrated in the examples.

In a further aspect the invention provides methods for treating or preventing neurodegenerative disease such as amyotrophic lateral sclerosis (ALS), comprising administering a therapeutically or prophylactically effective amount of the oligonucleotide of the invention to a subject suffering from or susceptible to the disease.

In a further aspect the oligonucleotide or composition of the invention is used for the treatment or prevention of a neurodegenerative disease as neurodegenerative disorders characterized by TDP-43 pathology or mis-localization of TDP-43 from the nucleus, such as amyotrophic lateral sclerosis (ALS).

SEQUENCE LISTING

The sequence listing submitted with this application is hereby incorporated by reference.

BRIEF DESCRIPTION OF FIGURES

(FIG. 5A) Graphical user interface illustrating normalized reads mapped to the 5' end of the STMN2 gene of untreated Glutaneurons, Glutaneurons treated with compound A, compound A+B and compound A+C. Grey rectangle highlights the aligned reads that usage of alternative splice acceptor site. (FIG. 5B) Relative expression of wild type STMN2 transcript in untreated Glutaneurons, Glutaneurons treated with compound A, compound A+B and compound A+C.

FIG. 6—Illustration of an example of the aberrant splicing event which results in the cryptic exon inclusion in STMN2 mRNA in TDP-43 depleted cells. The figure illustrates the nucleotide sequence of the STMN2 cryptic exon containing mRNA transcript (SEQ ID NO: 120) and the amino acid sequence (SEQ ID NO: 124) is the resulting truncated stathmin-2 protein (referred to herein as STMN2 protein). The shaded bold nucleotide sequence is the STMN2 exon 1 sequence and the underlined nucleotide sequence is the cryptic exon sequence which originates from intron 1, and the cryptic splice site is indicated by a v symbol. The ATG start codon, TAG stop codon and polyadenylation signal are highlighted.

(FIG. 7A) Graphical user interface illustrating normalized reads aligned to hg38 (partial zoom to ARHGAP32) of untreated Glutaneurons, Glutaneurons treated with compound A, compound A+B and compound A+C. Grey rectangle illustrates the aligned reads showing usage of alternative splice acceptor site. (FIG. 7B) Relative expression of the ARHGAP32 isoform with inclusion of alternative last exon (position 200153 in ENSG00000134909) in untreated Glutaneurons, Glutaneurons treated with compound A, compound A+B and compound A+C.

FIG. 8—Nucleotide sequence of the novel last exon of the ARHGAP32 gene (SEQ ID NO: 121), the novel cryptic splice site is indicated by a ^symbol, with the non-bold test representing the cryptic exon which is enriched in the TDP-43 depleted cells. The inclusion of the cryptic exon results in the inclusion of two polyadenylation sites (shaded text) within the cryptic exon, resulting in the expression of a truncated version of the Rho GTPase-activating protein 32, protein encoded by ARHGAP32. The italicized texts is the GT rich RNA binding protein binding site.

(FIG. 9A) Graphical user interface illustrating normalized reads aligned to SLC5A7 of untreated Glutaneurons, Glutaneurons treated with compound A, compound A+B and compound A+C. Grey rectangle illustrates the aligned reads showing inclusion of the alternative exon. (FIG. 9B) Relative expression of the SLC5A7 isoform with inclusion of alternative exon in untreated Glutaneurons, Glutaneurons treated with compound A, compound A+B and compound A+C.

FIG. 10—Nucleotide sequence of the novel exon to be included from the SLC5A7gene (SEQ ID NO: 122). The novel cryptic splice site is indicated by a ^symbol, with the non-bold underlined text representing the cryptic exon which is enriched in the TDP-43 depleted cells. The italicized texts is the GT rich RNA binding protein binding site (TDP-43 binding site).

(FIG. 11A) Graphical user interface illustrating normalized reads aligned to CERT1 of untreated Glutaneurons, Glutaneurons treated with compound A, compound A+B and compound A+C. Grey rectangle illustrates the aligned reads showing inclusion of the alternative exon. (FIG. 11B) Relative expression of the CERT1 isoform with inclusion of alternative exon in untreated Glutaneurons, Glutaneurons treated with compound A, compound A+B and compound A+C.

FIG. 12—Nucleotide sequence of the novel in frame exon included from the CERT1 gene in TDP-43 depleted cells (SEQ ID NO: 123). The new exon of CERT1 is shown in the underlined text, and the TDP-43 binding sites is in italics.

FIGS. 14A and 14B—FIG. 14A shows a graphical illustration showing mapping of normalized reads mapped to CAMK2B gene. Glutaneurons treated with compound A or untreated cells (PBS) as control, followed mRNA isolation and NGS. The position of the novel exons within the CAMK2B gene upon loss of TDP43 protein is illustrated with a horizontal grey rectangle (only exons surrounding the novel exon of CAMK2B is shown). The novel splice donor site is shown with a grey arrow. The CAMK2B pre-mRNA is transcribe from the minus strand. FIG. 14B shows the sequence (SEQ ID NO: 125) of the novel CAMK2B exon that is observed upon loss of TDP43 protein. In bold is the canonical exon observed in Glutaneurons. Underlined is the novel exon, and in italic is shown the first of many stop codons. ^ shows the canonical splice sites and ᵛ shows the position of the novel splice acceptor site.

FIGS. 15A-15D—FIG. 15A shows Graphical illustration showing mapping of normalized reads mapped to KALRN gene. Glutaneurons treated with compound A or untreated cells (PBS) as control, followed mRNA isolation and NGS. The position of the novel exons within the KALRN gene upon loss of TDP43 protein is illustrated in the grey rectangle (only exons surrounding the novel exon of KALRN is shown). FIG. 15B shows a graphical illustration zooming in on the mapping of normalized reads mapped to KALRN gene containing the aberrantly spliced exons. Glutaneurons treated with compound A or untreated cells (PBS) as control, followed mRNA isolation and NGS. The position of the novel exons within the KALRN gene upon loss of TDP43 protein is illustrated in the horizontal grey rectangles. Arrows indicates the splice sites used upon loss of TDP43 protein. FIG. 15C shows the sequence (SEQ ID NO: 126) of the novel KALRN exon that is observed upon loss of TDP43 protein. In bold is the novel exon observed in Glutaneurons. In italic is shown the first of many stop codons within the coding sequence. ᵛ shows the position of the novel splice sites. FIG. 15D shows ng the sequence (SEQ ID NO: 127) of the novel KALRN exon that is observed upon loss of TDP43 protein. In bold is the novel exon observed in Glutaneurons. In italic is shown the first of many stop codons within the coding sequence. ᵛ shows the position of the novel splice sites.

FIGS. 16A-16C-FIG. 16A shows Illustration of the aberrant splicing event which results in the inclusion of either the cryptic exon of 128 nucleotides (A) (SEQ ID NO: 128), or 178 nucleotides (B) (SEQ ID NO: 129). In bold is the nucleotide sequence of the two cryptic exons of UNC13A. The splice sites are illustrated by V and the intronic sequence 5' and 3' to the exon is shown in regular capital letters. Shown is the reverse complement sequence as UNC13A gene is positioned don the minus strand of chromosome 19. FIG. 16B shows a graphical illustration showing mapping of normalized reads mapped to UNC13A gene. Glutaneurons treated with compound A or untreated cells (PBS) as control, followed mRNA isolation and NGS. The position of the novel exons within the UNC13A gene upon loss of TDP43 protein is illustrated in the grey rectangle (only exons surrounding the novel exon of UNC13A is shown). FIG. 16C shows Graphical illustration showing the novel exons within the UNC13A gene upon loss of TDP43 protein. Glutaneurons treated with compound A or untreated cells (PBS) as control, followed mRNA isolation and NGS. The arrows illustrate the novel splice sites.

DEFINITIONS

Figure 1:
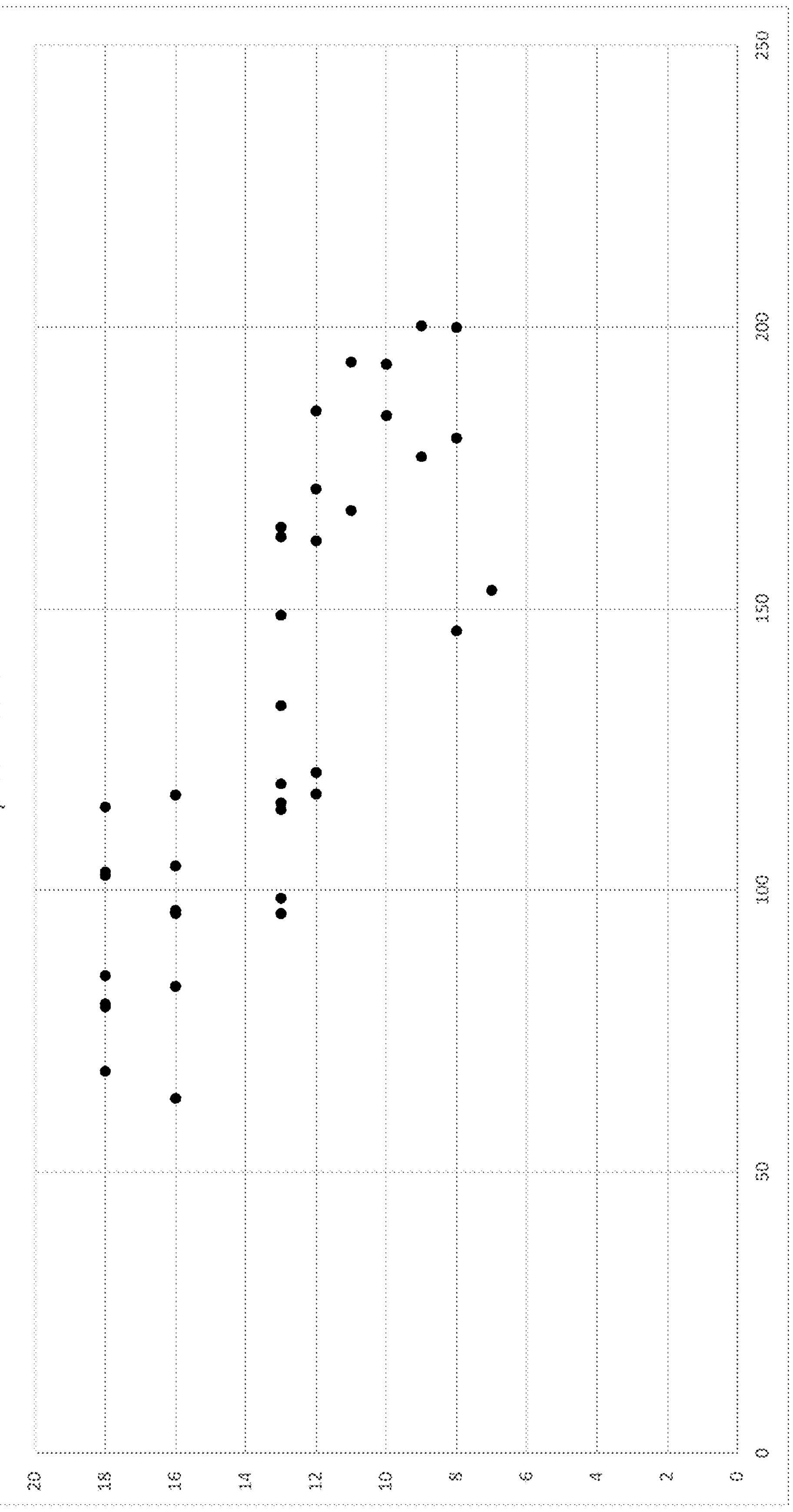
FIG. 1—Correlation between oligonucleotide length and the efficacy in correction of STMN2 mRNA processing in TDP-43 depleted cells, as measured by the ratio of aberrant STMN2 mRNA vs. WT STMN2 mRNA expression level. Of note the more effective compounds were at least 12 nucleotide in length.

RNA Binding Protein Mimics and TDP-43 Mimics

TDP-43 is the TAR RNA/DNA binding protein which in humans is encoded on the human chromosome 1: 11,012, 653-11,022,858 forward strand (Gene ENSG00000120948, Chr 1: 11,012,344-11,025,739, example of a typical TDP-43 transcript=ENST00000439080.6), and is widely involved in RNA splicing, stability and metabolism. In healthy cells the TDP-43 protein is located in the nucleus, however in several neurodegenerative diseases, dysfunction TDP-43 aggregates form in the cytoplasm (often associated with hyper-phosphorylated and ubiquitinated TDP-43).

TDP-43 is an example of a RNA binding protein which binds to GU repeats in numerous independent RNA transcripts. The interaction of RNA binding proteins, such as TDP-43 with the population of numerous RNA transcripts has a profound effect on the biology of the RNA transcripts, such as the splicing on pre-mRNA, RNA stability, RNA accumulation, and therefore provides a mechanism for effecting the expression of populations of independent RNAs in a cell. This is of particular relevance in the case of TDP-43 depletion, where the loss of RNA binding of functional TDP-43 is closely associated with neurodegeneration.

The present invention provides antisense oligonucleotides which are complementary to GU rich regions on multiple RNA transcripts, such as conserved TDP-43 binding sites on a population of pre-mRNA transcripts. As is illustrated in the examples, the administration of the oligonucleotides of the invention can restore the functional processing of multiple independent RNA transcripts, which are otherwise aberrantly processed in the depletion or absence of the RNA binding protein, for example TDP-43. The antisense oligonucleotides of the invention, otherwise referred to as compounds of the invention, may therefore be referred to as RNA binding protein mimics, or TDP-43 mimics, in that they restore the functionality of the RNA binding protein, such as TDP-43, in regulating the RNA biology of multiple RNA transcripts.

By way of example, the RNA binding protein functionality, such as TDP-43 functionality, which is restored or enhanced by the use of the compounds of the invention (e.g. in TDP-43 depleted cells), is the expression, processing, e.g. splicing events of pre-mRNA transcripts, resulting in a restoration of functional gene expression which is otherwise dysregulated in cells with reduced level of functional TDP-43 (referred to herein as TDP-43 depleted cells). This may result in an enhanced gene expression or an enhanced quality of gene expression.

Advantageously, the compounds of the invention are capable of mimicking the functional TDP-43, and restoring the nuclear function of TDP-43 in the expression of one or more TDP-43 target RNAs, and thereby restore the functional phenotype of the TDP-43 target RNA(s).

It will be understood that other RNA binding proteins may bind to the TDP-43 binding sites, and as such the TDP-43 mimics referred to herein are oligonucleotides, which are complementary to the TDP-43 binding sites of one or more RNA targets, such as multiple nucleic acid targets (i.e. RNA targets which are described from distinct genetic loci), and which are capable of restoring the expression of the normal (wildtype)

As reported in Arnold et al., PNAS 2013, some TDP-43 pathologies are associated with certain TDP-43 mutations, and these may not necessarily be associated with TDP-43 cytoplasmic depletion. In the context of the present invention the normal function of TDP-43 may be genetically disrupted, and this is therefore also considered a potential source of depletion or normal TDP-43, a phenotype which can be addressed using the TDP-43 mimics of the present invention.

Examples of TDP-43 RNA Targets

Figure 13:
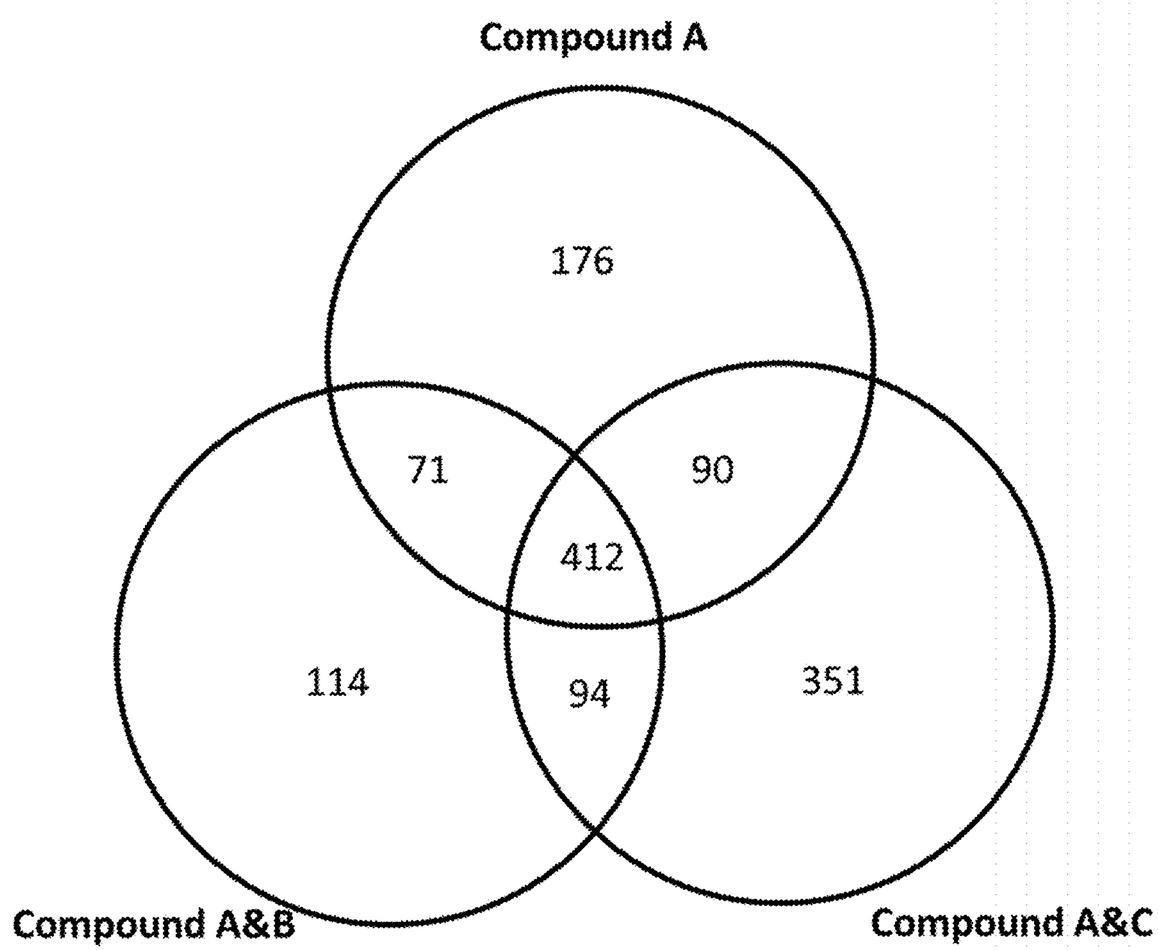
FIG. 13—Venn diagram. Number of transcripts that shows alternative splicing with a p-value below 0.01 and which shows more than a two-fold change compared to the control. The control for compound A is untreated Glutaneurons, whereas the control for compound A+B, and A+C is the TDP-43 knock down (compound A). In the TDP-43 depleted cells (treated with compound A only), there were a total of 925 transcripts which were alternatively spliced due to TDP-43 depletion. When the TDP-43 depleted cells were subsequently treated with a STMN2 targeting oligonucleotide (compound B), there were 114 transcripts which were alternatively spliced as compared to the compound A treated cells. When the TDP-43 depleted cells were subsequently treated with a RNA protein binding site targeting oligonucleotide of the invention (compound C), there were 351 transcripts which were alternatively spliced as compared to the compound A treated cells. This indicates that the compounds of the invention are more effective in modulating global RNA splicing as compared to the STMN2 targeting oligonucleotides.

As is illustrated in FIG. 13, the depletion of TDP-43 in neuronal cells results in a profound alteration in the RNA processing of a large population of RNA transcripts in the cell—In this example, 749 RNA transcripts illustrated alternative RNA processing as determined by RNA sequencing, after depletion of TDP-43.

The examples illustrate seven of these TDP-43 target RNAs: STMN2, ARHGAP32, SLC5A7, CERT1, CAMK2B, KALRN and UNC13A.

Arnold et al., PNAS 2013 110 E736—745 identifies widespread aberrations of pre-mRNA splicing of TDP-43 binding RNAs in TDP-43 depleted cells (TDP-43 ASO depleted mice), and illustrates the identification of indicative TDP-43 regulated splicing events using micro-array analysis. RNAs identified by Arnold et al., whose splicing is regulated by TDP-43 include Eif4h, Taf1b, Kcnip2, (TDP-43 mutation dependent), Sort1, Kcnd3, Ahi1, Atxn2, Ctnnd (dose dependent).

STMN2 (Klim et al., Nat Neurosci. 2019 February; 22(2): 167-179)—TDP-43 depletion in neuronal cells (e.g. in ALS) results in a mis-splicing of the STMN2 transcript. STMN2 encodes a microtubule regulator, whose expression declines after TDP-43 knockdown and TDP-43 mis-localization as well as in patient-specific motor neurons and postmortem patient spinal cord.

Post-translational stabilization of STMN2 rescued neurite outgrowth and axon regeneration deficits induced by TDP-43 depletion. TDP-43 depletion results in the incorporation of a cryptic intron between exon1 and 2 of STMN2. WO2019/241648 discloses fully MOE modified phosphorothioate ASOs which are used to suppress the mis-splicing of STMN2.

The above-mentioned transcripts and the associated TDP-43 depletion splicing events may be used to assay for restoration of TDP-43 functionality using the compounds of the invention.

TDP-43 Pathologies

A TDP-43 pathology is a disease which is associated with reduced or aberrant expression of TDP-43, often associated by an increase in cytoplasmic TDP-43, particularly hyper-phosphorylated and ubiquitinated TDP-43.

TDP-43 depletion is indicated in a range of diseases, referred to as TDP-43 pathologies, and include for example such as amyotrophic lateral sclerosis (ALS), frontotemporal lobar degeneration (FTLD), Progressive supranuclear palsy (PSP), Primary lateral sclerosis, Progressive muscular atrophy Alzheimer's disease, Parkinson's disease, Autism, Hippocampal sclerosis dementia, Down syndrome, Huntington's disease, polyglutamine diseases, such as spinocerebellar ataxia 3, myopathies and Chronic Traumatic Encephalopathy.

Cells which are Depleted in TDP-43

Cells which are depleted in TDP-43 refer to cells where the functional level of TDP-43 is reduced. It will be understood that in TDP-43 pathologies, aberrant TDP-43 expression results in accumulation of dysfunctional cytoplasmic TDP-43, and a reduction in the functional nuclear TDP-43 level—as such cells which are depleted in TDP-43 may be characterized by a reduction in the functional level of TDP-43, and may therefore be associated with an increase in the level of dysfunctional TDP-43. For in vitro assessment, TDP-43 depletion may be engineered for example by genetic engineering approaches (e.g. CRISPR/CAS9), or as illustrated in the examples, by use of an antisense oligonucleotide inhibitor of TDP-43 (illustrated by a gapmer oligonucleotide targeting the human TDP-43 transcript).

In some embodiments the cell which is depleted in TDP-43 is a neuronal cell.

Sequences Complementary to TDP-43 Binding Sites

TDP-43 binding sites are characterized by poly GU motifs (see the A database of RNA binding attract.cnic.es/results/e9f29380-8921-406e-84a8-27ce9b9398b4 #) for example, and suitably for antisense oligonucleotide intervention may comprise a motif of (GU)n or (UG)n, where n is at least 3 or preferably at least 4. In some embodiments n is 4, 5, 6, 7, 8, 9 or 10.

In some embodiments the TDP-43 binding site may comprise a sequence selected from the group consisting of (UG)n, (GU)n, wherein n is 4-20, UGUGUGUG, UGUGUGUGU, UGUGUGUGUG, UGUGUGUGUGU, UGUGUGUGUGUG, UGUGUGUGUGUGU, GUGUGUGU, GUGUGUGUG, GUGUGUGUGU, GUGUGUGUGUG, GUGUGUGUGUGU (SEQ ID NO: 42), GUGUGUGUGUGUG, and GUGAAUGA.

In some embodiments, the TDP-43 binding site may comprise a sequence selected from the group consisting of GUGAAUGA, GUUGUGC, UGUGUGUGUGUG (SEQ ID NO: 35), GAAUGG, UGUGUGUG, GAAUGA, UGUGUG, GUUGUUC, and GUUUUGC. In some embodiments, the TDP-43 binding site may comprise the sequence UGUGUGUGUGUGUG (SEQ ID NO: 46).

In some embodiments the oligonucleotide of the present invention may comprise a sequence which is complementary to, such as fully complementary to one or more sequences selected from the group consisting of (UG)n, (GU)n, wherein n is 4-20, UGUGUGUG, UGUGUGUGU, UGUGUGUGUG, UGUGUGUGUGU, UGUGUGUGUGUG, UGUGUGUGUGUGU, GUGUGUGU, GUGUGUGUG, GUGUGUGUGU, GUGUGUGUGUG, GUGUGUGUGUGU, GUGUGUGUGUGUG, and GUGAAUGA.

The oligonucleotide of the present invention may comprise a sequence which is complementary to, such as fully complementary to, the TDP-43 binding site sequence, such as one or more sequences, selected from the group consisting of (GU)n, (UG)n, GUGAAUGA, GUUGUGC, GAAUGG, UGUGUGUG, GAAUGA, UGUGUG, UGUGUGUGUGUG (SEQ ID NO: 35), GUUGUUC, and GUUUUGC.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotides of the invention are man-made, and are chemically synthesized, and are typically purified or isolated.

The oligonucleotides of the invention may comprise one or more modified nucleosides such as 2' sugar modified nucleosides. The oligonucleotides of the invention may comprise one or more modified internucleoside linkages, such as one or more phosphorothioate internucleoside linkages.

Antisense Oligonucleotides

The term "antisense oligonucleotide" as used herein is defined as an oligonucleotide capable of modulating expression of a target gene by hybridizing to a target nucleic acid, in particular to a contiguous sequence on a target nucleic acid. Antisense oligonucleotides are not essentially double stranded and are therefore not siRNAs or shRNAs. The antisense oligonucleotides of the present invention may be single stranded. It is understood that single stranded oligonucleotides of the present invention can form hairpins or intermolecular duplex structures (duplex between two molecules of the same oligonucleotide), as long as the degree of intra or inter self-complementarity is less than approximately 50% across of the full length of the oligonucleotide.

In some embodiments, the single stranded antisense oligonucleotides of the invention may not contain RNA nucleosides.

Advantageously, the antisense oligonucleotides of the invention comprise one or more modified nucleosides or nucleotides, such as 2' sugar modified nucleosides. Furthermore, in some antisense oligonucleotides of the invention, it may be advantageous that the nucleosides which are not modified are DNA nucleosides.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleosides of the antisense oligonucleotide constitute the contiguous nucleotide sequence. The contiguous nucleotide sequence is the sequence of nucleotides in the oligonucleotide of the invention which are complementary to, and in some instances fully complementary to, the target nucleic acid or target sequence.

In some embodiments the antisense oligonucleotide comprises the contiguous nucleotide sequence, and may optionally comprise further nucleotide(s), for example a nucleotide linker region which may be used to attach a functional group (e.g. a conjugate group) to the contiguous nucleotide sequence. The nucleotide linker region may or may not be complementary to the target nucleic acid. It is understood that the contiguous nucleotide sequence of the oligonucleotide cannot be longer than the oligonucleotide as such and that the oligonucleotide cannot be shorter than the contiguous nucleotide sequence.

Nucleotides and Nucleosides Nucleotides and nucleosides are the building blocks of oligonucleotides and polynucleotides, and for the purposes of the present invention include both naturally occurring and non-naturally occurring nucleotides and nucleosides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. Advantageously, one or more of the modified nucleosides of the antisense oligonucleotides of the invention comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing. Exemplary modified nucleosides which may be used in the compounds of the invention include LNA, 2'-O-MOE and morpholino nucleoside analogues.

Modified Internucleoside Linkage

The term "modified internucleoside linkage" is defined as generally understood by the skilled person as linkages other than phosphodiester (PO) linkages, that covalently couple two nucleosides together. The oligonucleotides of the invention may therefore comprise one or more modified internucleoside linkages such as one or more phosphorothioate internucleoside linkage.

In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% or more of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

Advantageously, all the internucleoside linkages of the contiguous nucleotide sequence of the oligonucleotide are phosphorothioate, or all the internucleoside linkages of the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but which are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research 45:2055 and Bergstrom (2009) Current Protocols in Nucleic Acid Chemistry Suppl. 371.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine, 5' nitroindole.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term "chimeric oligonucleotide" is a term that has been used in the literature to describe oligonucleotides comprising sugar modified nucleosides and DNA nucleosides. In some embodiments, it may be advantageous for the antisense oligonucleotide of the invention to be a chimeric oligonucleotide.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research 45:2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which, across the contiguous nucleotide sequence, are complementary to a reference sequence (e.g. a target sequence or sequence motif). The percentage of complementarity is thus calculated by counting the number of aligned nucleobases that are complementary (from Watson Crick base pairs) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

Within the present invention the level of complementarity between the contiguous nucleotide sequence of the antisense oligonucleotide and the TDP-43 binding site, or target sequence, may be at least about 75%.

Within the present invention the level of complementarity between the contiguous nucleotide sequence of the antisense oligonucleotide and the target TDP-43 binding site, or target sequence, may be at least about 80%.

Within the present invention the level of complementarity between the contiguous nucleotide sequence of the antisense oligonucleotide and the TDP-43 binding site, or target sequence, may be at least about 85%.

Within the present invention the level of complementarity between the contiguous nucleotide sequence of the antisense oligonucleotide and the TDP-43 binding site, or target sequence, may be at least about 90%.

Within the present invention the level of complementarity between the contiguous nucleotide sequence of the antisense oligonucleotide and the TDP-43 binding site, or target sequence, may be at least about 95%.

In some embodiments the contiguous nucleotide sequence may be fully complementary to the TDP-43 binding site, or target sequence. The term "fully complementary", refers to 100% complementarity.

The compounds of the invention are complementary to TDP-43 binding sites in TDP-43 target RNAs.

As illustrated in the examples, complete complementarity may not be required and in some embodiments, the oligonucleotide may comprise one, two, three, four, five, six, seven, eight or more mismatches to a TDP-43 target RNA TDP-43 RNA binding site to which it effectively binds. In this regard, oligonucleotides maybe designed which are sufficiently complementary to multiple but not identical TDP-43 binding sites in different TDP-43 Target RNAs. In some embodiments an universal base such as inosine may be used in complementary positions in the antisense oligonucleotide where these is not perfect identity of TDP-43 binding site sequence in the multiple TDP-43 RNA targets.

In some embodiments the contiguous nucleotide sequence may include one or more mismatches to a TDP-43 binding site, or target sequence.

In some embodiments the contiguous nucleotide sequence may include two or more mismatches to a TDP-43 binding site, or target sequence.

In some embodiments the contiguous nucleotide sequence may include three or more mismatches to a TDP-43 binding site, or target sequence.

In some embodiments the contiguous nucleotide sequence may include four or more mismatches to a TDP-43 binding site, or target sequence.

In some embodiments the contiguous nucleotide sequence may include five or more mismatches to a TDP-43 binding site, or target sequence.

In some embodiments the contiguous nucleotide sequence may include six or more mismatches to a TDP-43 binding site, or target sequence.

In some embodiments the contiguous nucleotide sequence may include seven or more mismatches to a TDP-43 binding site, or target sequence.

In some embodiments the contiguous nucleotide sequence may include eight or more mismatches to a TDP-43 binding site, or target sequence.

In some embodiments, oligonucleotides of the present invention which contain one more, such as two or more, three or more, four or more, five or more, six or more, seven or more, or eight or more mismatches, may hybridize to a target nucleic acid with estimated ΔG° values below −10 kcal for oligonucleotides that are 10-32 nucleotides in length.

In some embodiments, oligonucleotides of the present invention which contain one more, such as two or more, three or more, four or more, five or more, six or more, seven or more, or eight or more mismatches, may hybridize to a target nucleic acid with estimated ΔG° values below −12 kcal, −15 kcal, −17 kcal, −20 kcal, −30 kcal, −40 kcal, −50 kcal or −60 kcal for oligonucleotides that are 10-32 nucleotides in length.

Calculation of ΔG° values is discussed below.

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy ΔG° is a more accurate representation of binding affinity and is related to the dissociation constant ($K_d$) of the reaction by $\Delta G° = -RT\ln(K_d)$, where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1 M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, Chem. Comm. 36-38 and Holdgate et al., 2005, Drug Discov Today.

The skilled person will know that commercial equipment is available for ΔG° measurements. $\Delta G^0$ can also be estimated numerically by using the nearest neighbor model as described by SantaLucia, 1998, Proc Nat/Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In some embodiments, oligonucleotides of the present invention hybridize to a target nucleic acid with estimated $\Delta G^0$ values below −10 kcal for oligonucleotides that are 10-30 nucleotides in length. In some embodiments the degree or strength of hybridization is measured by the standard state Gibbs free energy $\Delta G^0$. The oligonucleotides may hybridize to a target nucleic acid with estimated $\Delta G^0$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Exemplary TDP-43 RNA Targets In some embodiments, a TDP-43 target RNA is the mammalian protein known as stathmin 2, or SCG10, SCGN10, for example the human STMN2 as disclosed as Gene: ENSG00000104435 (ensemble.org), encoded on human Chromosome 8: 79,610,814-79,666,175 forward strand (GRCh38:CM000670.2).

In some embodiments, a TDP-43 target RNA is the mammalian protein known as Ceramide transporter 1 (CERT1) for example the human CERT1 as disclosed as Gene: ENSG000001 13163 (ensemble.org), encoded on human Chromosome 5: 75,356,345-75,512,138 reverse strand (GRCh38:CM000667.2).

In some embodiments, aTDP-43 target RNA is the mammalian protein known as solute carrier family 5 member 7, for example the human SLC5A7 as disclosed as Gene: ENSG00000115665(ensemble.org), encoded on human Chromosome 2: 107,986,523-108,013,994 forward strand (GRCh38:CM000664.2).

In some embodiments, aTDP-43 target RNA is the mammalian protein known as Rho GTPase activating protein 32, for example the human ARHGAP32, as disclosed as Gene:

ENSG00000134909(ensemble.org), encoded on human Chromosome 11: 128,965,060-129,279,324 reverse strand (GRCh38:CM000673.2).

In some embodiments, aTDP-43 target RNA is CAMK2B.

In some embodiments, aTDP-43 target RNA is KALRN.

In some embodiments, aTDP-43 target RNA is UNC13A.

Target Cell The term "target cell" as used herein refers to a cell which is expressing the targeted TDP-43 RNA targets whose expression is to be corrected by the administration of the compound of the invention. Suitably the target cell is further TDP-43 depleted. For experimental use, TDP-43 depletion may be engineered into the cell, e.g. via genetic engineering (e.g. CRISPR/CAS9) or via the use of ASO inhibitors of TDP-43.

In some embodiments the target cell may be in vivo or in vitro. In some embodiments the target cell is a mammalian cell such as a rodent cell, such as a mouse cell or a rat cell, or a primate cell such as a monkey cell or a human cell.

In some embodiments the target cell is a neuronal cell.

For in vitro evaluation, the target cell may be a glutamatergic neuron (also referred to herein as a glutaneuron cell), such as a human glutamatergic neuron, such as a human glutamatergic neuron which is TDP-43 depleted. Human glutamatergic neuron are available from Cellular Dynamics (iCell GlutaNeurons). For in vitro evaluation the target cell, such as the glutaneuron are in vitro. TDP-43 depletion of the target cell, for example for in vitro evaluation, may be achieved for example using antisense oligonucleotides or siRNA reagents, or may be engineered into the cells e.g. via CRISPR/Cas9 editing, or shRNA vector expression. As further illustrated in the examples, the target cell, for example for in vitro use, may be a human pluripotent stem cell-derived neuron, for example these are obtainable as iCell GlutaNeurons Kit, 01279 Cat. R1034 (Fujifilm Cellular Dynamics).

Splice Modulation Splice modulation can be used to correct cryptic splicing, modulate alternative splicing, restore the open reading frame, and induce protein knock-down.

Splice modulation may be assayed by RNA sequencing (RNAseq), which allows for a quantitative assessment of the different splice products of a pre-mRNA, or by digital droplet PCR using PCR assays designed to be specific for one or the other splice form. In some embodiments of the invention, the antisense oligonucleotide modulates the splicing of the STMN2 pre-mRNA, e.g. they reduce the level of mature STMN2 mRNA which comprises a RNA sequence positioned between the exon 1 and exon 2 (as illustrated in the examples), for example in the target cell or TDP-43 depleted cells. In some embodiments of the invention, the antisense oligonucleotide modulates the splicing of the STMN2 pre-mRNA, e.g. they enhance the level of mature correctly spliced STMN2 mRNA which does not comprise a RNA sequence positioned between the exon 1 and exon 2, referred to as WT STMN2 transcript, for example in the target cell.

In some embodiments of the invention, the antisense oligonucleotide of the invention modulates the splicing of CERT1 in the target cell, such as by reducing the inclusion of an aberrant exon in the mature CERT1 mRNA, as illustrated in the examples.

In some embodiments of the invention, the antisense oligonucleotide of the invention modulates the splicing of SLC5A7 in the target cell, such as by reducing the inclusion of an aberrant exon in the mature SLC5A7 mRNA, as illustrated in the examples.

In some embodiments of the invention, the antisense oligonucleotide of the invention modulates the splicing of ARHGAP32in the target cell, such as by reducing the inclusion of an aberrant exon in the mature ARHGAP32 mRNA, as illustrated in the examples.

High affinity modified nucleosides A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar modifications The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in DNA and RNA nucleosides.

Substituents may, for example be introduced at the 2', 3', 4' or 5' positions. 2' sugar modified nucleosides A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl.

Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

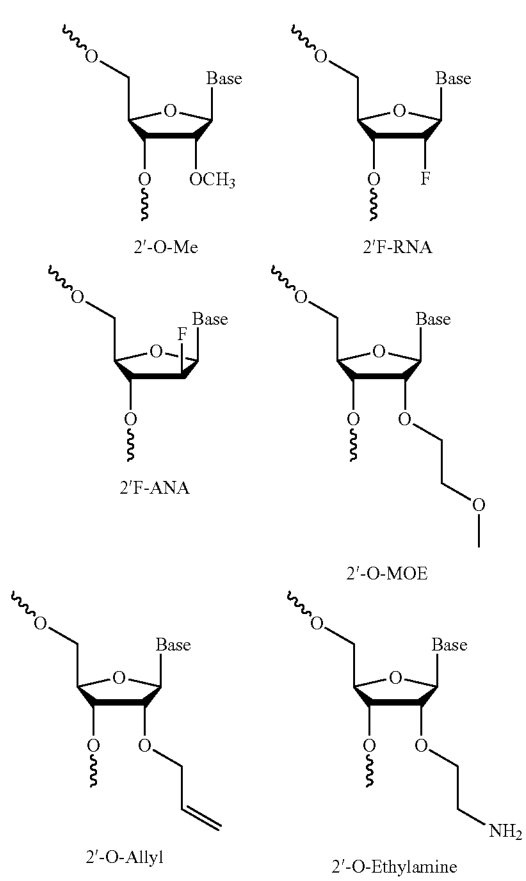

In relation to the present invention 2' substituted sugar modified nucleosides does not include 2' bridged nucleosides like LNA.

Locked Nucleic Acid Nucleosides (LNA nucleoside) A "LNA nucleoside" is a 2'—modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1

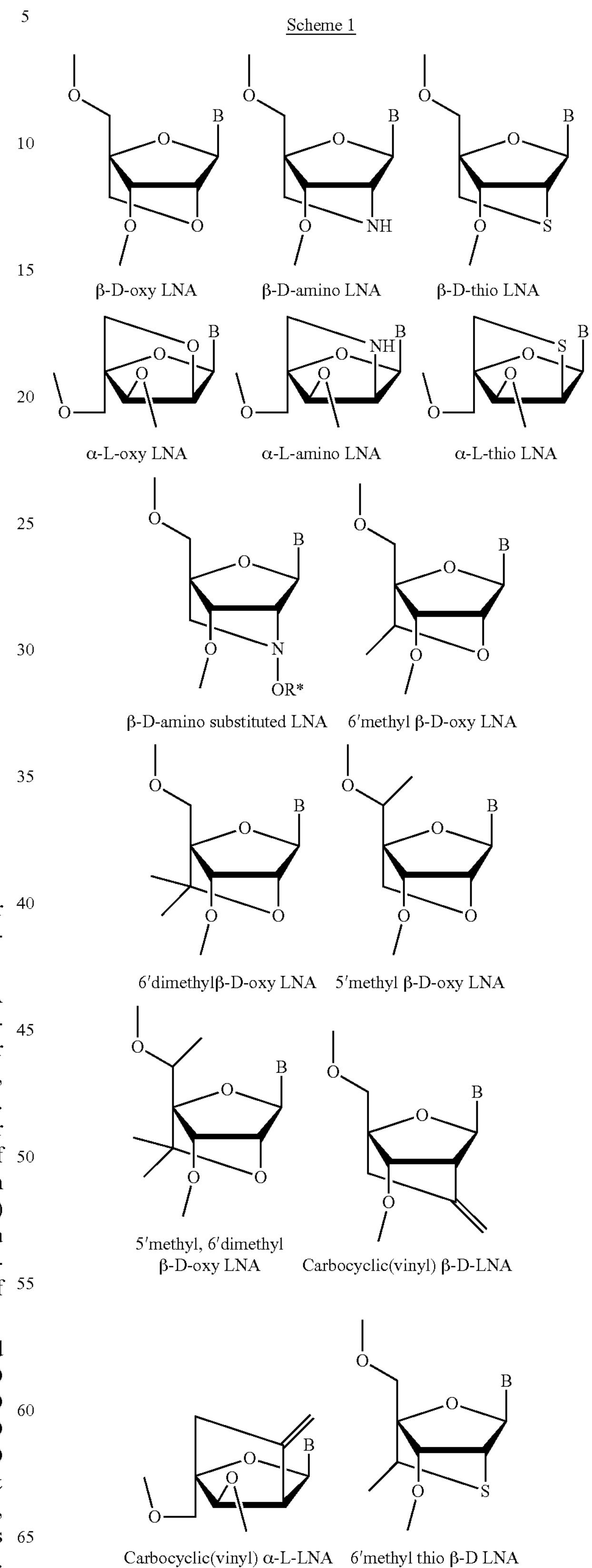

-continued

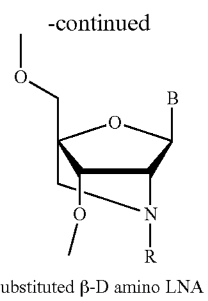

Substituted β-D amino LNA

Particular LNA nucleosides are beta-D-oxy-LNA, 6'-methyl-beta-D-oxy LNA such as (S)-6'-methyl-beta-D-oxy-LNA (ScET) and ENA.

A particularly advantageous LNA is beta-D-oxy-LNA.

Morpholino Oligonucleotides

In some embodiments, the oligonucleotide of the invention comprises or consists of morpholino nucleosides (i.e. is a Morpholino oligomer and as a phosphorodiamidate Morpholino oligomer (PMO)).

Splice modulating morpholino oligonucleotides have been approved for clinical use—see for example eteplirsen, a 30 nt morpholino oligonucleotide targeting a frame shift mutation in DMD, used to treat Duchenne muscular dystrophy. Morpholino oligonucleotides have nucleobases attached to six membered morpholine rings rather ribose, such as methylenemorpholine rings linked through phosphorodiamidate groups, for example as illustrated by the following illustration of 4 consecutive morpholino nucleotides:

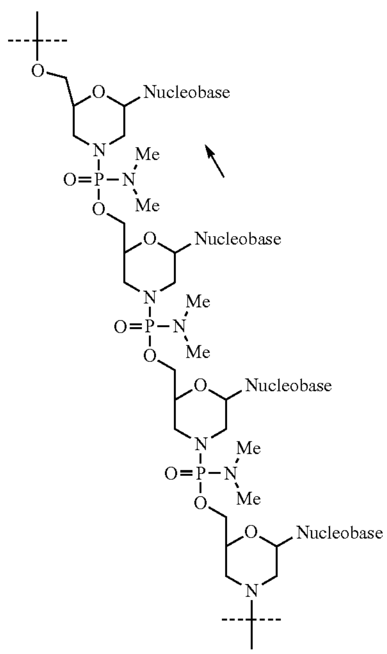

In some embodiments, morpholino oligonucleotides of the invention may be, for example 20-40 morpholino nucleotides in length, such as morpholino 25-35 nucleotides in length.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant RNase H1 is available from Lubio Science GmbH, Lucerne, Switzerland. DNA oligonucleotides are known to effectively recruit RNaseH, as are gapmer oligonucleotides which comprise a region of DNA nucleosides (typically at least 5 or 6 contiguous DNA nucleosides), flanked 5' and 3' by regions comprising 2' sugar modified nucleosides, typically high affinity 2' sugar modified nucleosides, such as 2-O-MOE and/or LNA. For effective modulation of splicing, degradation of the pre-mRNA is not desirable, and as such it is preferable to avoid the RNaseH degradation of the target.

Therefore, the oligonucleotides of the invention is preferably not gapmer oligonucleotide. RNaseH recruitment may be avoided by limiting the number of contiguous DNA nucleotides in the oligonucleotide—therefore for effective splice modulation mixmers and totalmers designs may therefore be used.

Mixmers and Totalmers

For splice modulation it is often advantageous to use antisense oligonucleotides which do not recruit RNAseH. As RNaseH activity requires a contiguous sequence of DNA nucleotides, RNaseH activity of antisense oligonucleotide may be achieved by designing antisense oligonucleotides which do not comprise a region of more than 3 or more than 4 contiguous DNA nucleosides. This may be achieved by using antisense oligonucleotides or contiguous nucleoside regions thereof with a mixmer design, which comprise sugar modified nucleosides, such as 2' sugar modified nucleosides, and short regions of DNA nucleosides, such as 1, 2 or 3 DNA nucleosides. Mixmers are exemplified herein by every second design, wherein the nucleosides alternative between 1 LNA and 1 DNA nucleoside, e.g. LDLDLDLDLDLDLDLL, with 5' and 3' terminal LNA nucleosides, and every third design, such as LDDLDDLDDLDDLDDL, where every third nucleoside is a LNA nucleoside.

A totalmer is an antisense oligonucleotide or a contiguous nucleotide sequence thereof which does not comprise DNA or RNA nucleosides, and may for example comprise only 2'-O-MOE nucleosides, such as a fully MOE phosphorothioate, e.g. MMMMMMMMMMMMMMMMMMMM, where M=2'-O-MOE, which are reported to be effective splice modulators for therapeutic use. Alternatively, a mixmer may comprise a mixture of modified nucleosides, such as MLMLMLMLMLMLMLMLMLML, wherein L=LNA and M=a non LNA modified nucleoside such as a 2'-O-MOE nucleosides.

Advantageously, the internucleoside nucleosides in mixmers and totalmers may be phosphorothioate, or a majority of nucleoside linkages in mixmers may be phosphorothioate. Mixmers and totalmers may comprise other internucleoside linkages, such as phosphodiester or phosphorodithioate, by way of example.

Region D' or D" in an oligonucleotide

The contiguous sequence of nucleobases of the oligonucleotide of the invention is typically complementary to multiple TDP-43 binding sites present in distinct TDP-43 RNA targets. The region of the antisense oligonucleotide which is complementary to, such as fully complementary to, the TDP-43 binding site is referred to as the contiguous nucleotide sequence. In some embodiments all of the nucleosides of the antisense oligonucleotide are within the contiguous nucleotide sequence (i.e. the antisense oligonucleotide and contiguous nucleotide sequence are of the same length of nucleotides). In some embodiments the antisense oligonucleotide comprises the contiguous nucleotide sequence and optionally a nucleotide-based linker region which may link the oligonucleotide to an optional functional group such as a conjugate, or other non-complementary terminal nucleotides (e.g. region D' or D").

The oligonucleotide of the invention may in some embodiments comprise or consist of the contiguous nucleotide sequence of the oligonucleotide which is complementary to the target nucleic acid, such as a mixmer or totalmer region, and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the mixmer or totalmer, to a conjugate moiety or another functional group. When used for joining the contiguous nucleotide sequence with a conjugate moiety is can serve as a biocleavable linker. Alternatively, it may be used to provide exonuclease protection or for ease of synthesis or manufacture.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs within a single oligonucleotide.

In one embodiment the oligonucleotide of the invention comprises a region D' and/or D" in addition to the contiguous nucleotide sequence which constitutes a mixmer or a totalmer.

In some embodiments the internucleoside linkage positioned between region D' or D" and the mixmer or totalmer region is a phosphodiester linkage.

Conjugate

The term conjugate as used herein refers to an oligonucleotide which is covalently linked to a non-nucleotide moiety (conjugate moiety or region C or third region). The conjugate moiety may be covalently linked to the antisense oligonucleotide, optionally via a linker group, such as region D' or D".

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103.

In some embodiments, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In some embodiments the nuclease susceptible linker comprises between 1 and 5 nucleosides, such as DNA nucleoside(s) comprising at least two consecutive phosphodiester linkages. Phosphodiester containing biocleavable linkers are described in more detail in WO 2014/076195.

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In some embodiments the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic. In some embodiments, the treatment is not prophylactic, for example, the treatment is treatment of an existing disease condition which has been diagnosed in the patient.

DETAILED DESCRIPTION OF THE INVENTION

The Oligonucleotides of the Invention

The oligonucleotide of the invention is an antisense oligonucleotide which is complementary to an RNA binding site on multiple independent pre-mRNA transcripts, such as to a TDP-43 RNA binding site on multiple pre-mRNA transcripts. The oligonucleotide of the invention is capable or modulating the expression of the multiple pre-mRNA transcripts, for example via (independently) modulation of pre-mRNA splicing, enhancing RNA stabilization, enhancing expression of the encoded protein, reducing expression of truncated proteins encoded by the pre-mRNA(s). As illustrated in the examples, the oligonucleotide of the invention may therefore be used to enhance the fidelity of pre-mRNA processing into mature mRNA encoding correctly expressed and functional proteins. The oligonucleotides of the invention may therefore be suitable for use in the treatment of diseases which are associated with a dysregulation of pre-mRNA maturation.

In some embodiments, the oligonucleotide of the invention may comprise one, two, three, four, five, six, seven, eight or more mismatches between the oligonucleotide and the target nucleic acid TDP-43 binding region. Despite mismatches hybridization to the target nucleic acid may still be sufficient to show a desired modulation of the TDP-43 RNA target RNA. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

In some embodiments, one, two, three, four, five six, seven, eight or more universal nucleosides, such as inosine, may be used at mismatch positions.

Inosine is a nucleoside having the following structure:

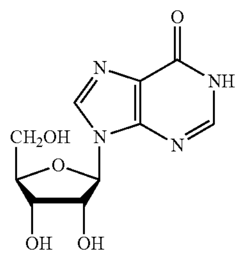

Universal nucleosides are particularly useful when oligonucleotides are targeted to different TDP-43 target RNAs which have non-identical TDP-43 binding regions.

In some embodiments the contiguous nucleotide sequence may include one or more universal nucleotides at positions representing mismatches to a TDP-43 binding site, or target sequence.

In some embodiments the contiguous nucleotide sequence may include two or more universal nucleotides at positions representing mismatches to a TDP-43 binding site, or target sequence.

In some embodiments the contiguous nucleotide sequence may include three or more universal nucleotides at positions representing mismatches to a TDP-43 binding site, or target sequence.

In some embodiments the contiguous nucleotide sequence may include four or more universal nucleotides at positions representing mismatches to a TDP-43 binding site, or target sequence.

In some embodiments the contiguous nucleotide sequence may include five or more universal nucleotides at positions representing mismatches to a TDP-43 binding site, or target sequence.

In some embodiments the contiguous nucleotide sequence may include six or more universal nucleotides at positions representing mismatches to a TDP-43 binding site, or target sequence.

In some embodiments the contiguous nucleotide sequence may include seven or more universal nucleotides at positions representing mismatches to a TDP-43 binding site, or target sequence.

In some embodiments the contiguous nucleotide sequence may include eight or more universal nucleotides at positions representing mismatches to a TDP-43 binding site, or target sequence.

In some embodiments, oligonucleotides of the present invention which contain one more, such as two or more, three or more, four or more, five or more, six or more, seven or more, or eight or more universal nucleotides at positions representing mismatches, may hybridize to a target nucleic acid with estimated ΔG° values below −10 kcal for oligonucleotides that are 10-32 nucleotides in length.

In some embodiments, oligonucleotides of the present invention which contain one more, such as two or more, three or more, four or more, five or more, six or more, seven or more, or eight or more mismatches, may hybridize to a target nucleic acid with estimated ΔG° values below −12 kcal, −15 kcal, −17 kcal, −20 kcal, −30 kcal, −40 kcal, −50 kcal or −60 kcal for oligonucleotides that are 10-32 nucleotides in length.

Calculation of ΔG° values is discussed above.

In some embodiments, the antisense oligonucleotide of the invention or the contiguous nucleotide sequence thereof comprises or consists of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 contiguous nucleotides in length.

In some embodiments, the oligonucleotide or contiguous nucleotide sequence comprises or consists of a sequence selected from the group consisting of sequences SEQ ID NO: 1-18 or a sequence selected from SEQ ID NOs 1-34 and SEQ ID NOs 50-103. It will be understood that the sequence shown in SEQ ID NO: 1-18 or a sequence selected from SEQ ID NOs 1-34 and SEQ ID NOs 50-103 may include modified nucleobases which function as the shown nucleobase in base pairing, for example 5-methyl cytosine may be used in place of methyl cytosine. Inosine may be used as a universal base.

In some embodiments, the antisense oligonucleotide or contiguous nucleotide sequence comprises or consists of 8 to 30 or 8 to 40 nucleotides in length with at least 75%, such as at least 80%, at least 85%, at least 90% identity, at least 90% or more identity to a sequence selected from the group consisting of SEQ ID NO: 1 to 18 or a sequence selected from SEQ ID NOs 1-34 and SEQ ID NOs 50-103. In some embodiments the antisense oligonucleotide or contiguous nucleotide sequence comprises or consists of 8 to 30 or 8 to 40 nucleotides in length with 100% identity to a sequence selected from the group consisting of SEQ ID NO: 1 to 18 or a sequence selected from SEQ ID NOs 1-34 and SEQ ID NOs 50-103.

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15, at least 16 modified nucleosides, at least 17 modified nucleosides, at least 18 modified nucleosides, at least 19 modified nucleosides, at least 20 modified nucleosides, at least 21 modified nucleosides, at least 22 modified nucleosides, at least 23 modified nucleosides, at least 24 modified nucleosides, at least 25 modified nucleosides, at least 26 modified nucleosides, at least 27 modified nucleosides, at least 28 modified nucleosides, at least 29 modified nucleosides, at least 30 modified nucleosides, at least 31 modified nucleosides, at least 32 modified nucleosides or more. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprise one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the oligonucleotide comprises at least one modified internucleoside linkage.

Suitable internucleoside modifications are described in the "Definitions" section under "Modified internucleoside linkage". It is advantageous if at least 75%, such as all, the internucleoside linkages within the contiguous nucleotide sequence are phosphorothioate or boranophosphate internucleoside linkages.

In some embodiments all the internucleotide linkages in the contiguous sequence of the oligonucleotide are phosphorothioate linkages.

Pharmaceutically Acceptable Salts

The invention contemplates pharmaceutically acceptable salts of the antisense oligonucleotides of the invention. In some embodiments, the pharmaceutically acceptable salt is a sodium salt, a potassium salt or an ammonium salt.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 μM solution.

Applications

The oligonucleotides of the invention may be utilized as research reagents for, for example, diagnostics, therapeutics and prophylaxis.

In research, such oligonucleotides may be used to mimic the activity of TDP-43 in cells (e.g. in vitro cell cultures, such as in neuronal cells) and experimental animals thereby facilitating functional analysis of the target or an appraisal of its usefulness as a target for therapeutic intervention.

The present invention provides a method, such as an in vivo or in vitro method, for enhancing TDP-43 functionality in a cell which is expressing aberrant or depleted levels of TDP-43, said method comprising administering an oligonucleotide, the conjugate, the salt or composition according to the invention, in an effective amount to said cell. In some embodiments, the target cell, is a mammalian cell in particular a human cell. The target cell may be an in vitro cell culture or an in vivo cell forming part of a tissue in a mammal. In preferred embodiments the target cell is a neuronal cell, such as a neuronal cell which is depleted in normal TDP-43 activity. In some embodiments, the target cell may express a disease associated variant of TDP-43, and/or express dysfunctional TDP-43.

For therapeutics, the oligonucleotides may be administered to an animal or a human, suspected of having a disease or disorder, which can be treated by mimicking TDP-43.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The invention further relates to use of an oligonucleotide, oligonucleotide conjugate or a pharmaceutical composition as defined herein for the manufacture of a medicament for the treatment of a neurological disorder as neurodegenerative disorders characterized by TDP-43 pathology or mis-localization of TDP-43 from the nucleus, such as ALS.

The invention also provides the oligonucleotide or antisense oligonucleotide of the invention for use in a method of treating a disorder as referred to herein.

In one embodiment, the invention relates to oligonucleotides, oligonucleotide conjugates or pharmaceutical compositions for use in the treatment of a neurological disorder as neurodegenerative disorders characterized by TDP-43 pathology or mis-localization of TDP-43 from the nucleus, such as ALS.

Administration

The oligonucleotides or pharmaceutical compositions of the present invention may, for example be administered for example via intracerebral, intracerebroventricular or intrathecal administration.

In a preferred embodiment the oligonucleotide or pharmaceutical compositions of the present invention are administered by a parenteral route including intravenous, intraarterial, subcutaneous, intraperitoneal or intramuscular injection or infusion, intrathecal or intracranial, e.g. intracerebral or intraventricular, intravitreal administration. In one embodiment the active oligonucleotide or oligonucleotide conjugate is administered intravenously. In another embodiment the active oligonucleotide or oligonucleotide conjugate is administered subcutaneously.

EXAMPLES

Example 1—Evaluation of a Range of "TDP-43" Mimic ASOs in their Ability to Correct Splicing of STMN2 Pre-mRNA in TDP-43 Depleted Neuronal Cells Compounds Used:

Compounds 1, 1-19.1 (compound A)

Material and Methods

Cell Culture Material:

96 well, black/clear, Tissue Culture Treated plate—Flat bottom with Lid, Falcon 353219 Laminin 521 Biolamina DPBS (1×) $CaCl_2$)+/MgCl2+, Gibco 14040-091

DAPT Sigma Aldrich D5942 iCell Motor Neurons Kit, 01279 Cat. R1049 (Fujifilm Cellular Dynamics)

RNA Isolation Material:

Rneasy Plus 96 Kit, Qiagen Cat No.: 74192

Rnase-Free Dnase Set, Qiagen Cat No.: 79254

Library preparation material:

TruSeq® Stranded Total RNA Library Prep Gold, Illumina Cat No.: 20020599

Cell Seeding, Maintenance and LNA Oligonucleotides Treatment:

Human glutamatergic neurons were plated at 2.0×105 cells/cm2 on 96-well plates coated with Poly-L-Ornithine/Laminin. To knockdown TDP-43, cells were incubated with compound A at 5 μM from day 3. From day 10, cells were treated additionally with compound 1.1 to 18.1 at 10 μM for 72 hours and then lysed in lysis buffer (supplied with the kit). Control cells were treated with the diluent alone (PBS). RNA isolation was performed according to the manufacturer's instructions including DNase treatment step.

TDP-43 LNA oligonucleotide—compound A:

SEQ ID NO: 19,1=TCcacactgaacaAACC (Upper case letters are beta-D-oxy LNA, lower case letters are DNA, LNA Cs are 5-methyl cytosine, all internucleoside linkages are phosphorothioate).

Medium was removed and 100 ul/well (96mwp) Lysis Buffer (PureLink® Pro 96 Thermo Fisher Kit) was added. RNA purification was performed as per the manufacturer's instructions, including Dnase I treatment (RNA Purification PureLink® Pro 96 Thermo Fisher Kit)

RNA Sequencing Analysis

Sequencing libraries were generated using TruSeq stranded total RNA library preparation protocol with RiboZero to remove rRNA (Illumina). Libraries were subjected to paired end sequencing on a NovaSeq6000 sequencer (Illumina) with 150-bp read length.

Samples: The human motor neurons (hMNS) treated with and without TARDBP (encoding TDP-43) targeting oligonucleotide 19.1 and the range of TDP-43 mimic ASOs, compound 1.1-18.1. Data analysis was carried out using Partek Flow (mapping using hg38 and Cufflinks).

Figure 2:
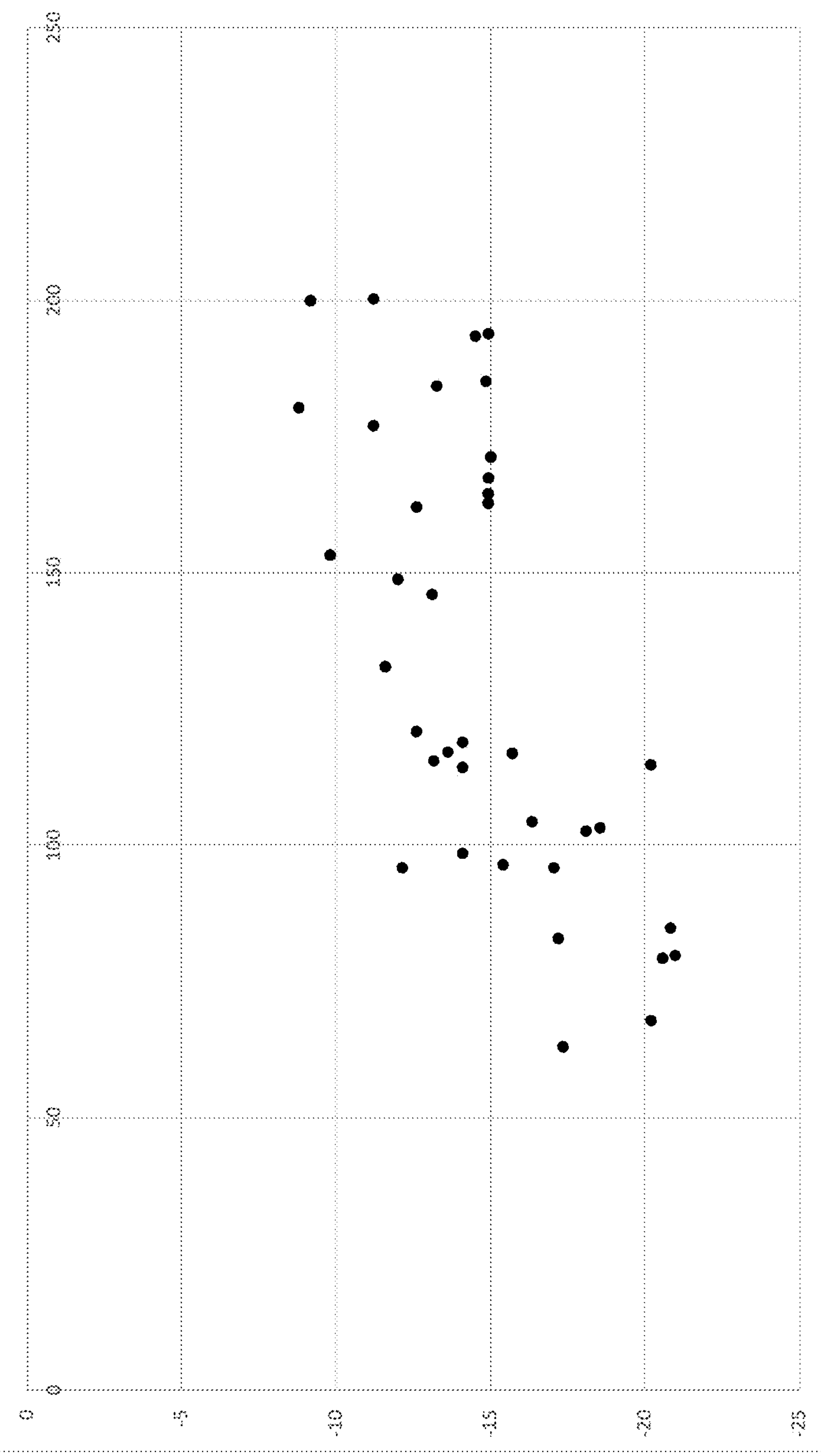
FIG. 2—Correlation between oligonucleotide Gibbs Free energy (AG) and the efficacy in correction of STMN2 mRNA processing in TDP-43 depleted cells, as measured by the ratio of aberrant STMN2 mRNA vs. WT STMN2 mRNA expression level. Of note the more effective compounds had a Gibbs free energy of at least −10 ΔG.
Figure 3:
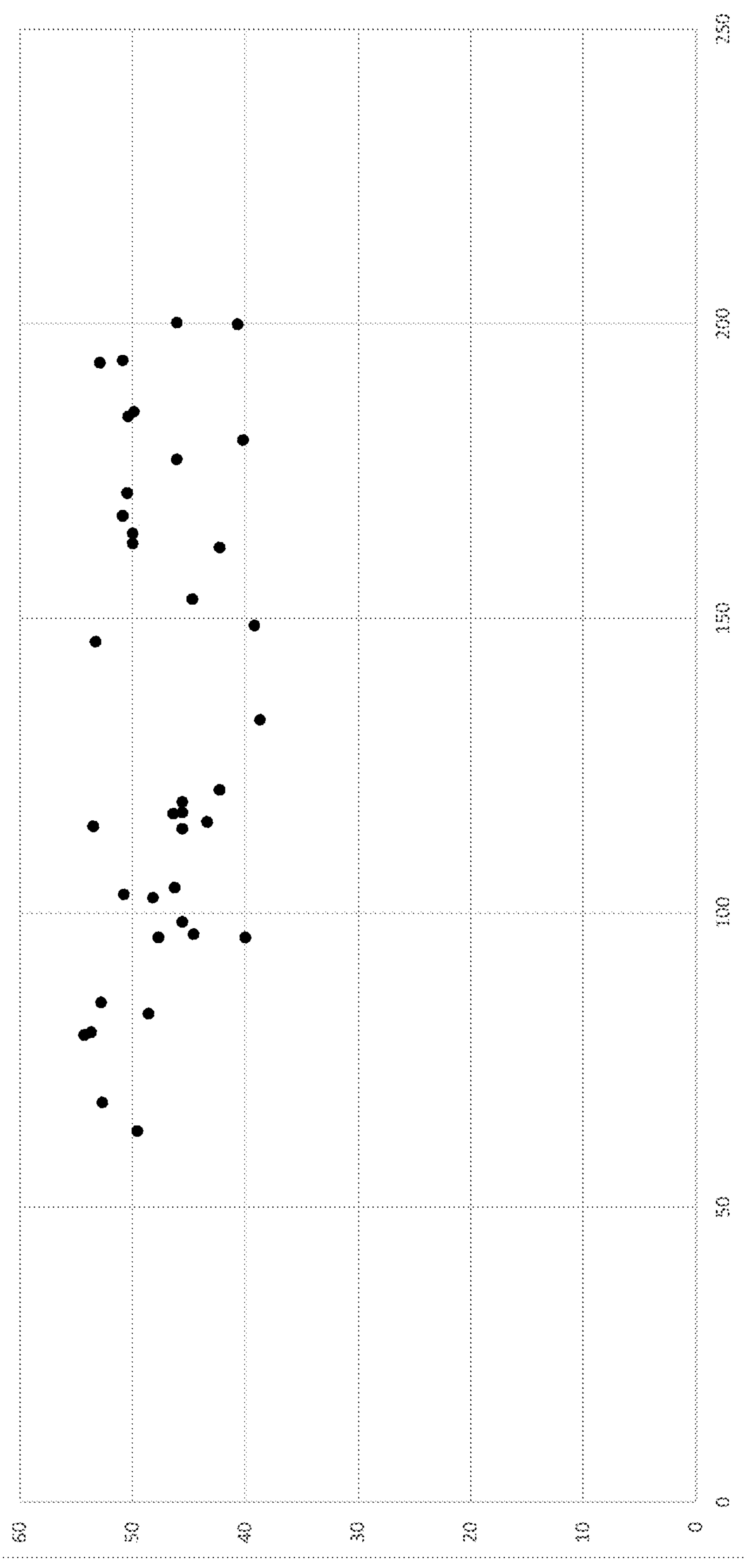
FIG. 3—Lack of a correlation between oligonucleotide melting temperature (predicted Tm) and the efficacy in correction of STMN2 mRNA processing in TDP-43 depleted cells, as measured by the ratio of aberrant STMN2 mRNA vs. WT STMN2 mRNA expression level.

The expression level of STMN2 containing the cryptic exon, and the level of wildtype STMN2 was normalized to the expression level in the untreated control cells (100%), and are shown in Results Table A and illustrated in FIGS. 1-3.

The following compounds resulted in an enhanced expression of the WT STMN2 mRNA in TDP-43 depleted cells: 5.1, 14.1, 1.1, 15.5, 14.2, 15.1, 6.1, 6.4, 13.1, 15.4, 9.1, 10.1, 6.3, 7.1, 18.1, 8.1, 7.3, 16.3, 14.4, 15.3, 6.2, 8.2, 7.2, 18.3, 16.1, 16.2, 15.2, 18.2, and 8.3

The following compounds resulted in an enhanced expression of the WT STMN2 mRNA in TDP-43 depleted cells greater than the expression level in the control cells: 18.1, 8.1, 7.3, 16.3, 14.4, 15.3, 6.2, 8.2, 7.2, 18.3, 16.1, 16.2, 15.2, 18.2, and 8.3. These particularly effective compounds ranged in 12-18 nts in length. These particularly effective compounds ranged in Gibbs free energy of dG of about −12 to about −21.

Of note is that the most effective compounds had a length of 18 nts and a Gibbs free energy of about −20, indicating that compounds of at least 12 nucleotides in length with a Gibbs free energy of at least about −12 are advantageous.

The following compounds reduced the expression of the STMN2 aberrantly spliced mRNA in TDP-43 depleted cells: 18.4, 16.1, 14.2, 6.4, 8.3, 18.3, 8.1, 16.3, 14.3, 6.3, 16.2, 7.1, 3.1, 15.5, 7.3, 18.1, 5.1, 15.3, 18.2, 2.1, 15.4, and 12.1.

The following TDP-43 mimic oligonucleotide compounds resulted in a notable decrease in the ratio of the STMN2 cryptic exon containing STMN2 transcripts compared to the WT STMN2 transcripts (less than 150): 16.1, 8.3, 18.3, 18.4, 16.2, 18.2, 7.2, 15.2, 16.3, 15.3, 8.1, 8.2, 7.3, 6.4, 6.3, 18.1, 7.1, 14.2, 6.2, 14.4, 15.4, 10.1, 15.5.

As illustrated in FIGS. 1-3, there is a clear tendency that compounds with a longer length (FIG. 1) and/or a lower Gibbs free energy (ΔG) (FIG. 2) to be more effective in correcting the TDP-43 mediated correct splicing. Notable the melting temperature of the oligonucleotide/RNA duplex was not found to correlate to a correction of TDP-43 mediated splice correction (FIG. 3).

RESULTS TABLE A

| COMP ID No | SEQ ID NO | Base sequence | STMN2 cryptic exon 2a (A) | STMN2 wt (8) | Ratio (A/B) x 100 | Oligo length | Tm | Gibbs Free energy |
|---|---|---|---|---|---|---|---|---|
| 1.1 | 1 | 5'-ACACACAC-3' | 140 | 78 | 180 | 8 | 64 | -8.8 |
| 2.1 | 2 | 5'-ACACACACA-3' | 126 | 71 | 177 | 9 | 64 | -11.2 |
| 3.1 | 3 | 5'-ACACACACAC-3' | 118 | 64 | 184 | 10 | 65 | -13.3 |
| 4.1 | 4 | 5'-ACACACACACA-3' | 137 | 71 | 194 | 11 | 66 | -14.9 |
| 5.1 | 5 | 5'-ACACACACACAC-3' | 124 | 72 | 171 | 12 | 63 | -15.0 |
| 6.1 | 6 | 5'-ACACACACACACA-3' | 137 | 83 | 164 | 13 | 62 | -14.9 |
| 6.2 | 6 | 5'-ACACACACACACA-3' | 150 | 126 | 119 | 13 | 54 | -14.1 |
| 6.3 | 6 | 5'-ACACACACACACA-3' | 114 | 98 | 115 | 13 | 54 | -13.2 |
| 6.4 | 6 | 5'-ACACACACACACA-3' | 98 | 86 | 114 | 13 | 53 | -14.1 |
| 7.1 | 7 | 5'-ACACACACACACACAC-3' | 116 | 99 | 117 | 16 | 54 | -15.7 |
| 7.2 | 7 | 5'-ACACACACACACACAC-3' | 131 | 136 | 96 | 16 | 49 | -15.4 |
| 7.3 | 7 | 5'-ACACACACACACACAC-3' | 119 | 114 | 104 | 16 | 51 | -16.3 |
| 8.1 | 8 | 5'-ACACACACACACACACAC-3' | 111 | 108 | 103 | 18 | 51 | -18.5 |
| 8.2 | 8 | 5'-ACACACACACACACACAC-3' | 137 | 133 | 103 | 18 | 51 | -18.1 |
| 8.3 | 8 | 5'-ACACACACACACACACAC-3' | 101 | 149 | 68 | 18 | 40 | -20.2 |
| 9.1 | 9 | 5'-CACACAC-3' | 149 | 97 | 153 | 7 | 61 | -9.8 |
| 10.1 | 10 | 5'-CACACACA-3' | 142 | 97 | 146 | 8 | 59 | -13.1 |
| 10.2 | 10 | 5'-CACACACA-3' | 142 | 71 | 200 | 8 | 67 | -9.2 |
| 11.1 | 11 | 5'-CACACACAC-3' | 133 | 66 | 200 | 9 | 67 | -11.2 |
| 12.1 | 12 | 5'-CACACACACA-3' | 129 | 66 | 193 | 10 | 66 | -14.5 |
| 13.1 | 13 | 5'-CACACACACAC-3' | 147 | 88 | 167 | 11 | 63 | -14.9 |
| 14.1 | 14 | 5'-CACACACACACA-3' | 139 | 75 | 185 | 12 | 65 | -14.9 |
| 14.2 | 14 | 5'-CACACACACACA-3' | 96 | 82 | 117 | 12 | 54 | -13.6 |
| 14.3 | 14 | 5'-CACACACACACA-3' | 113 | 70 | 162 | 12 | 62 | -12.6 |
| 14.4 | 14 | 5'-CACACACACACA-3' | 145 | 120 | 121 | 12 | 55 | -12.6 |
| 15.1 | 15 | 5'-CACACACACACAC-3' | 133 | 82 | 163 | 13 | 62 | -14.9 |
| 15.2 | 15 | 5'-CACACACACACAC-3' | 137 | 143 | 96 | 13 | 49 | -12.1 |
| 15.3 | 15 | 5'-CACACACACACAC-3' | 124 | 125 | 99 | 13 | 50 | -14.1 |
| 15.4 | 15 | 5'-CACACACACACAC-3' | 127 | 96 | 133 | 13 | 57 | -11.6 |
| 15.5 | 15 | 5'-CACACACACACAC-3' | 118 | 79 | 149 | 13 | 60 | -12.0 |
| 16.1 | 16 | 5'-CACACACACACACACA-3' | 87 | 138 | 63 | 16 | 39 | -17.3 |
| 16.2 | 16 | 5'-CACACACACACACACA-3' | 115 | 139 | 83 | 16 | 45 | -17.2 |
| 16.3 | 16 | 5'-CACACACACACACACA-3' | 111 | 116 | 96 | 16 | 49 | -17.1 |
| 18.1 | 18 | 5'-CACACACACACACACACA-3' | 121 | 105 | 115 | 18 | 53 | -20.2 |
| 18.2 | 18 | 5'-CACACACACACACACACA-3' | 124 | 146 | 85 | 18 | 46 | -20.8 |

-continued

RESULTS TABLE A

| COMP ID No | SEQ ID NO | Base sequence | STMN2 cryptic exon 2a (A) | STMN2 wt (8) | Ratio (A/B) × 100 | Oligo length | Tm | Gibbs Free energy |
|---|---|---|---|---|---|---|---|---|
| 18.3 | 18 | 5'-CACACACACACACACACA-3' | 107 | 136 | 79 | 18 | 44 | -20.6 |
| 18.4 | 18 | 5'-CACACACACACACACACA-3' | 48 | 60 | 80 | 18 | 44 | -21.0 |
| 19.1 | 19 | 5'-TCCACACTGAACAAACC-3' | 130 | 71 | 183 | — | — | — |

Example 2—Human Pluripotent Stem Cell-Derived Neuronal Culture, Oligonucleotide Treatment and RNA Isolation—Evaluation of TDP-43 Mimic ASOs to Correct Aberrant Slicing of Multiple Independent RNAs in TDP-43 Depleted Cells Oligonucleotides Used Compound A:

A TDP-43 targeting LNA gapmer oligonucleotide, SEQ ID NO: 19 TCcacactgaacaAACC (Upper case letters are beta-D-oxy LNA, lower case letters are DNA, LNA Cs are 5-methyl cytosine, all internucleoside linkages are phosphorothioate)—referred to herein as Compound #19.1.

Compound B—STMN2

A LNA/DNA mixmer which targets and upregulates the expression of STMN2 Compound ID NO 36: ${}^{m}C_{s}a_{s}c_{s}A_{s}c_{s}A_{s}c_{s}G_{s}c_{s}A_{s}c_{s}A_{s}c_{s}a_{s}T_{s}G$ (SEQ ID NO: 36) wherein capital letters are beta-D-oxy LNA nucleotides, lower case letters are 2'deoxyribose nucleosides (DNA nucleoside), ${}^{m}C$ are 5-methyl cytosine beta-D-oxy LNA nucleosides, and subscript s is a phosphorothioate internucleoside linkage.

Compound C—TDP43

A LNA/DNA 18 nt mixmer (compound (8,3) of formula $A_{s}{}^{m}C_{s}A_{s}c_{s}a_{s}c_{s}A_{s}c_{s}A_{s}c_{s}a_{s}c_{s}A_{s}c_{s}A_{s}c_{s}a{}^{m}C$ (SEQ ID NO: 8) wherein capital letters are beta-D-oxy LNA nucleotides, lower case letters are 2'deoxyribose nucleosides (DNA nucleoside), ${}^{m}C$ are 5-methyl cytosine beta-D-oxy LNA nucleosides, and subscript s is a phosphorothioate internucleoside linkage.

The methodology used for performing the experiment was as described in example 1, however after the pre-treatment with compound A, the cells were either treated with compound B or compound C, or no additional compound.

Sequencing libraries were generated using TruSeq stranded total RNA library preparation protocol with RiboZero to remove rRNA (Illumina). Libraries were subjected to paired end sequencing on a NovaSeq6000 sequencer (Illumina) with 150-bp read length and an average output of 100 million paired end reads. Data analysis was performed after trimming of the reads (removal of short reads as well as removal of the last nucleotide from the 3' end). Reads were mapped against hg38 by usage of TopHat 2, and quantification of transcripts was performed by usage of Cufflinks. Identification of alternative spliced transcripts was performed by usage of a pipeline included in Partek Flow.

Sequencing of mRNA was performed at Fasteris (Swiss)-Sequencing was performed in triplicates with an average output of 100 million paired end reads. Data analysis was performed after trimming of the reads (removal of short reads as well as removal of the last nucleotide from the 3' end). Reads were mapped against hg38 by usage of TopHat 2, and quantification of transcripts was performed by usage of Cufflinks. Identification of alternative spliced transcripts was performed by usage of a pipeline included in Partek Flow.

Results

Since TDP-43 is known to be important in canonical splicing of a number of pre-mRNAs (Conti et al., 2015 and Humphrey et al. 2017), we chose to sequence Glutaneurons treated with compound A, A+B, A+C as well as untreated cells. The next generation sequencing (Illumina) was performed on isolated mRNA as paired end (PE) sequencing (2×150 bp) to obtain more than 100 million PE reads. To identify alternative splicing within the transcriptome, the number of reads were subsampled to have 104 million PE reads per sample (treatments were performed in triplicates).

Figure 4:
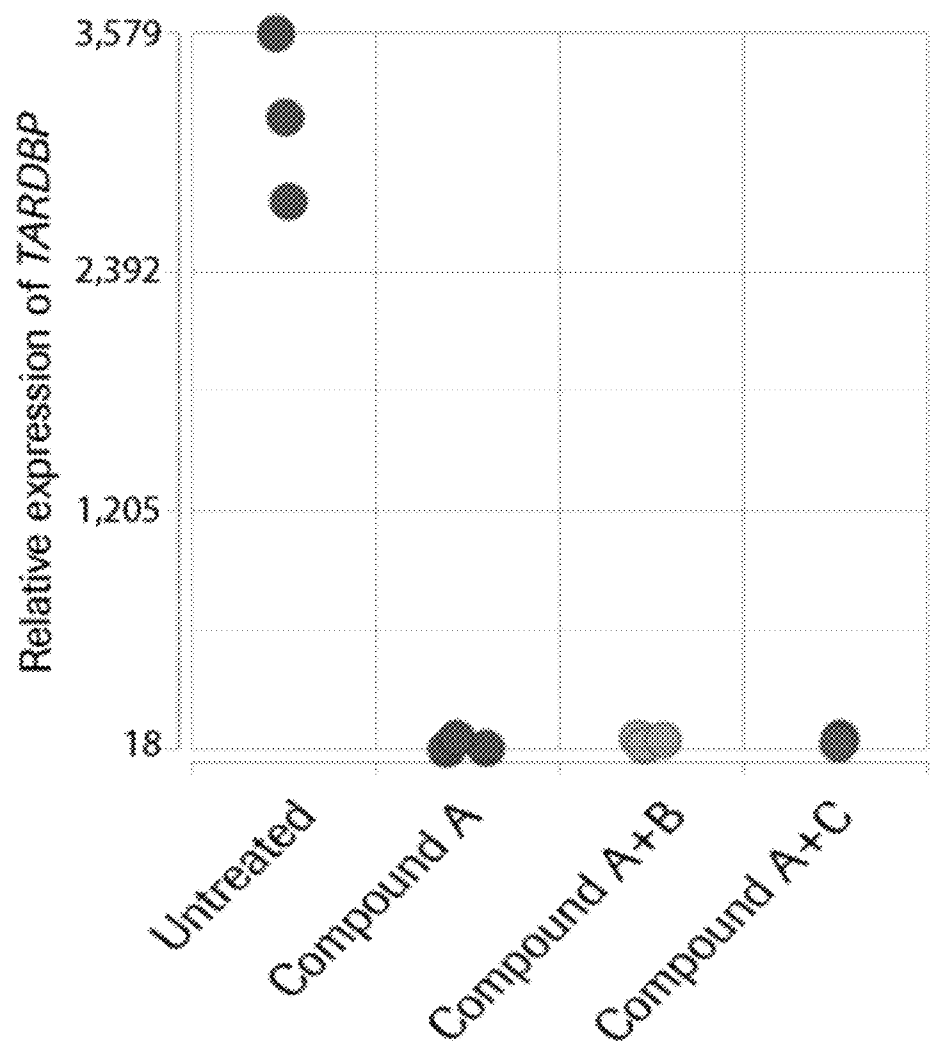
FIG. 4—TARDBP knock down in Glutaneurons upon treatment with compound A. Relative expression of TARDBP in untreated Glutaneurons, Glutaneurons treated with compound A, compound A+B and compound A+C.

To make sure that TARDBP was removed after treatment with the gapmer against TARDBP, we investigated the expression level based on the mRNA-Seq data. There was observed approximate 75-fold knock down of TARDBP encoding TDP-43 protein (remaining TARDBP transcripts less than 2%) (FIG. 4). As seen from the relative expression, treatment with compound A+B or A+C did not change the expression level of TARDBP compared to treatment with TARDBP ASO (compound A) alone (FIG. 4).

STMN2

Figure 5A:
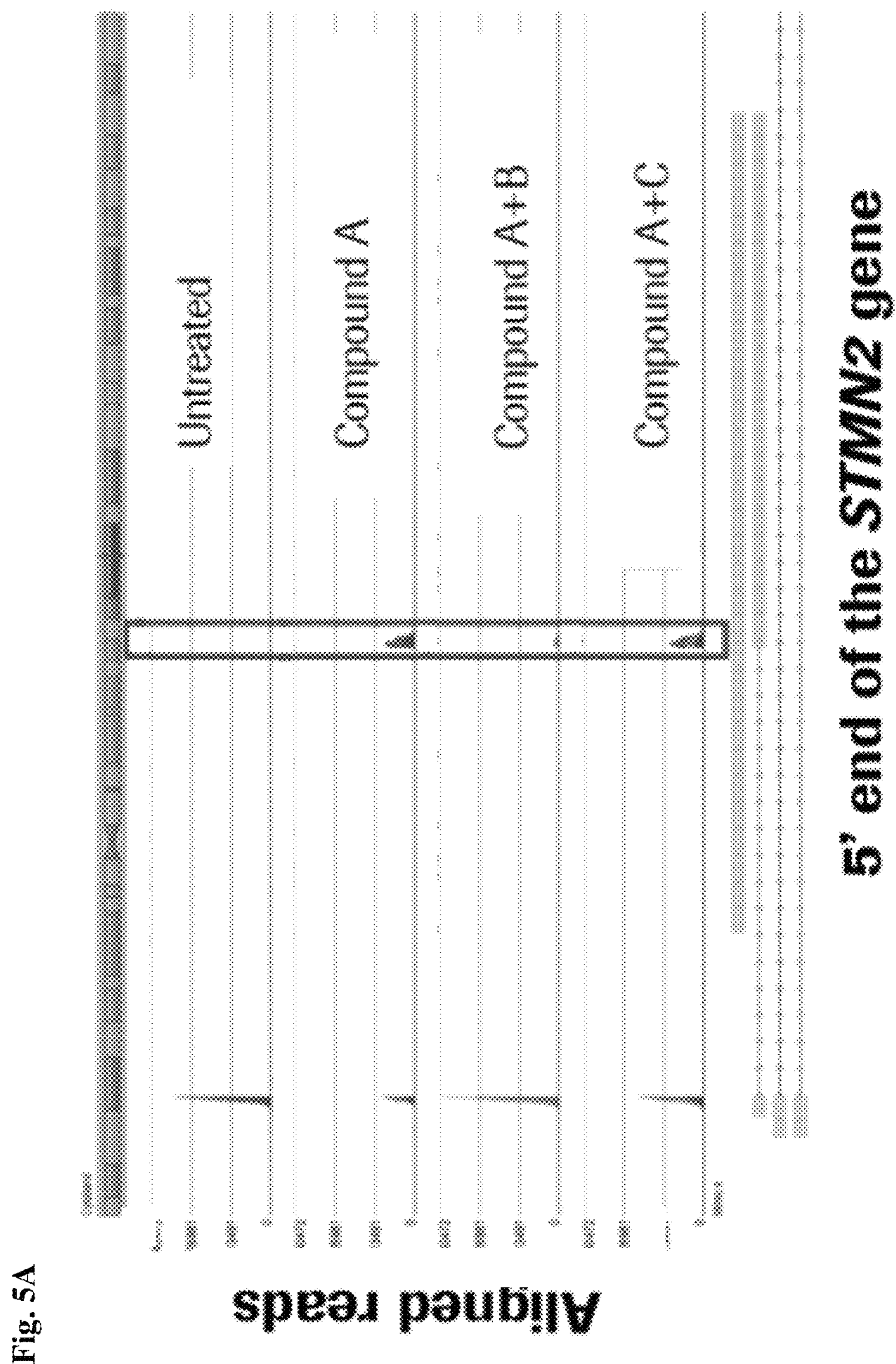
FIGS. 5A and 5B—STMN2 wild type expression in Glutaneurons upon treatment with compound A.
Figure 5B:
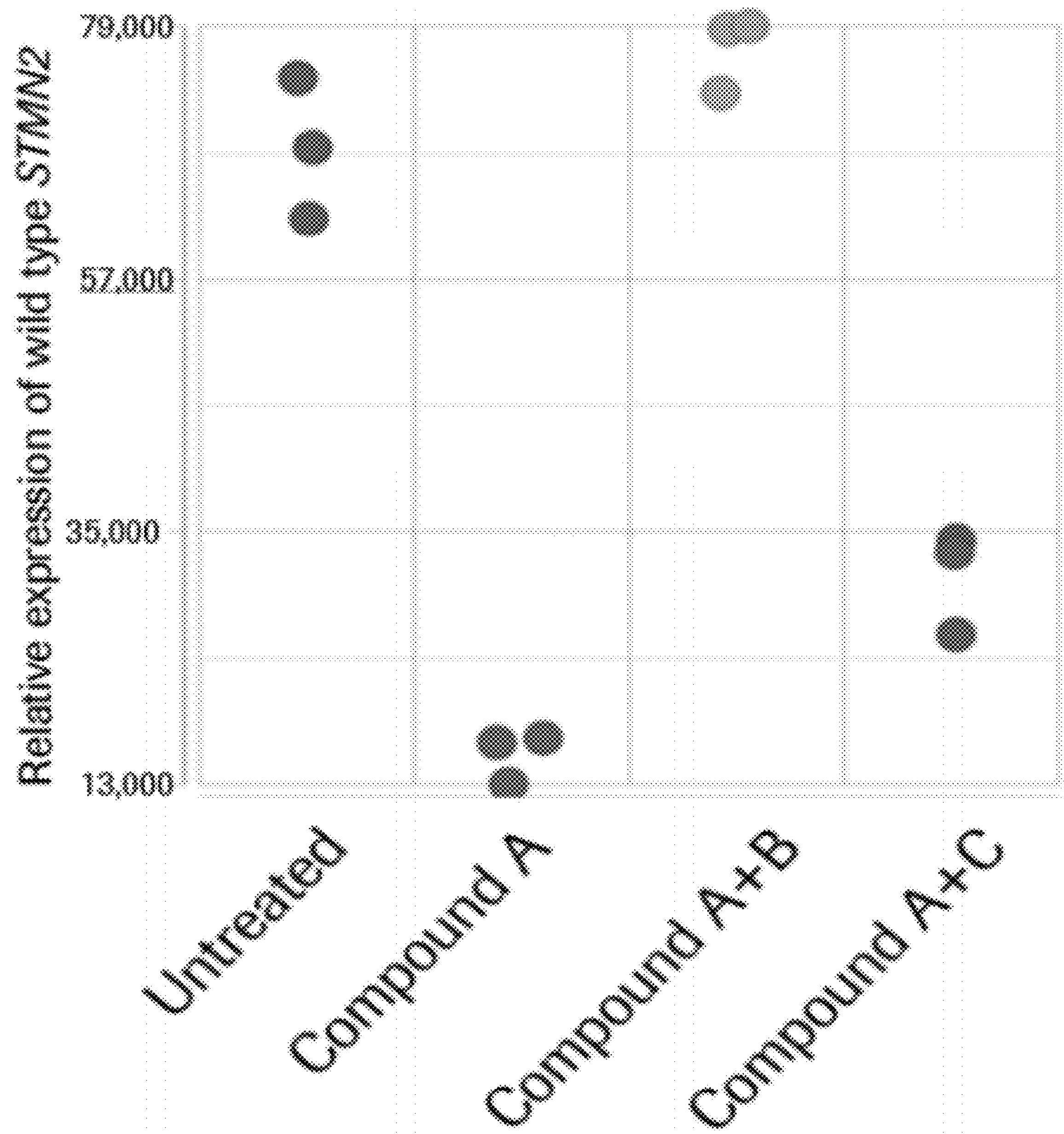

Next we investigated other transcripts that changed splicing pattern upon treatment with compound A (TDP-43 KD), and which could be restored upon treatment with our TDP-43 mimicking oligo (compound C). A TDP-43 mimicking ASO targeting the TDP-43 binding site of STMN2 was included as control (compound B). Initially we looked at the inclusion of the new splice acceptor site that previously was published was affected by our STMN2 specific ASO (compound B) or the general TDP-43 mimicking ASO (compound C). The analysis showed that the amount of wild type (wt) STMN2 was fully restored by treatment with compound A+B, and partially restored with compound A+C (FIGS. 5A and 5B). The restoration of the wild type STMN2 is due to blocking binding to the TDP-43 binding site and thereby preventing the usage of STMN2 splice acceptor site in intron 1. This new splice acceptor site that was published in 2019 (Klim et al. 2019 and Melamed et al. 2019) (positioned at chr8:79,616,822) replaces the acceptor site normally used for STMN2 exon 2. Usage of this new splice acceptor site results in a splice variant that is shortened due to usage of a polyadenylation site 203 nucleotides 3' to the splice acceptor site (FIG. 6).

STMN2 encodes a protein necessary for normal hMN outgrowth and repair. Importantly, we established that post-translational stabilization of STMN2 can rescue deficits in motor neurite outgrowth and axon regeneration induced by TDP-43 knockdown.

Klim, J. R., Williams, L. A., Limone, F. Et al. ALS-implicated protein TDP-43 sustains levels of STMN2, a mediator of motor neuron growth and repair, Nat Neurosci 22, 167-179 (2019) (doi.org/10.1038/s41593-018-0300-4).

ARHGAP32

Figure 7A:
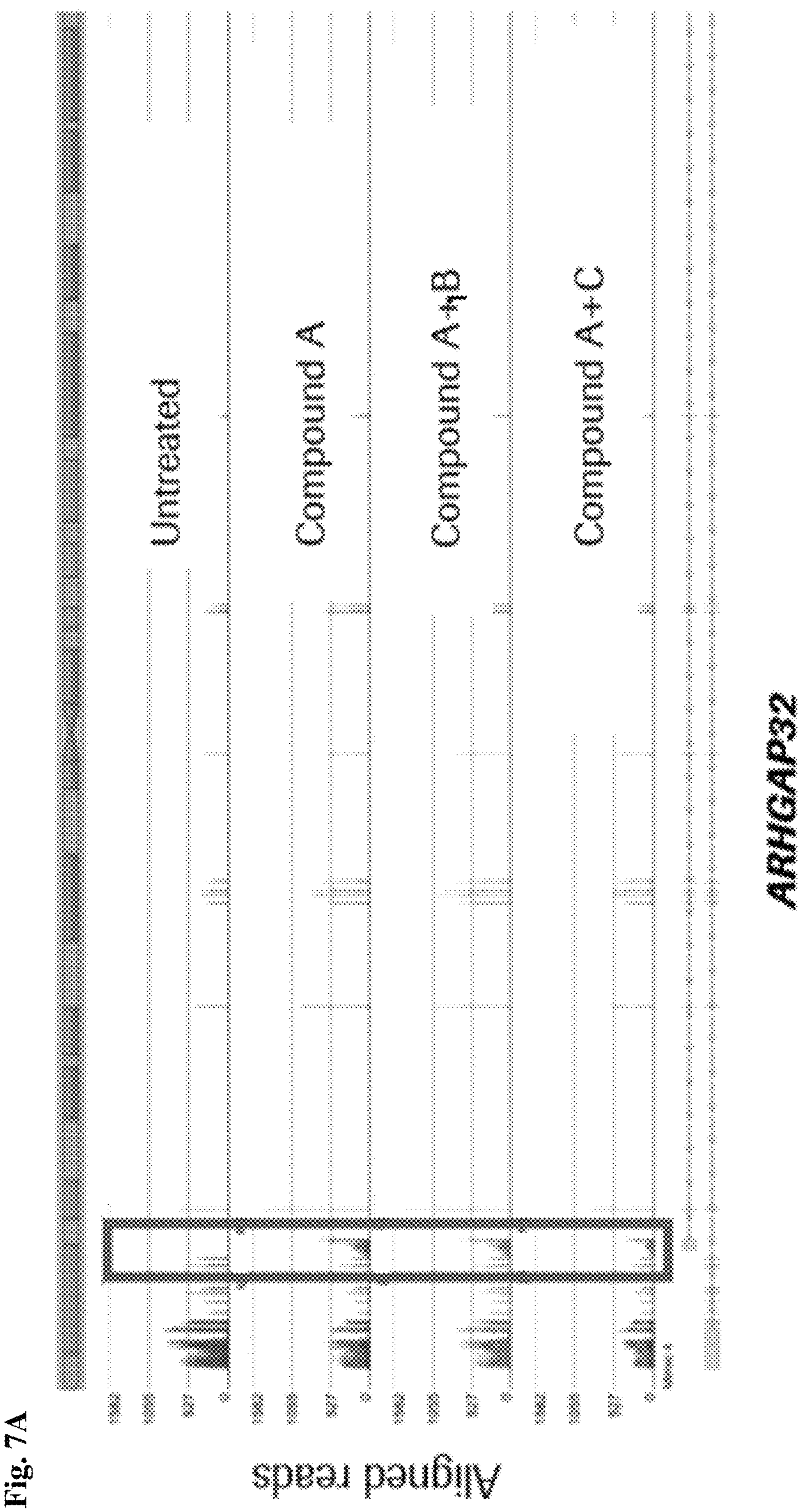
FIGS. 7A and 7B—ARHGAP32 expression in Glutaneurons upon treatment with compound A, B and C.
Figure 7B:
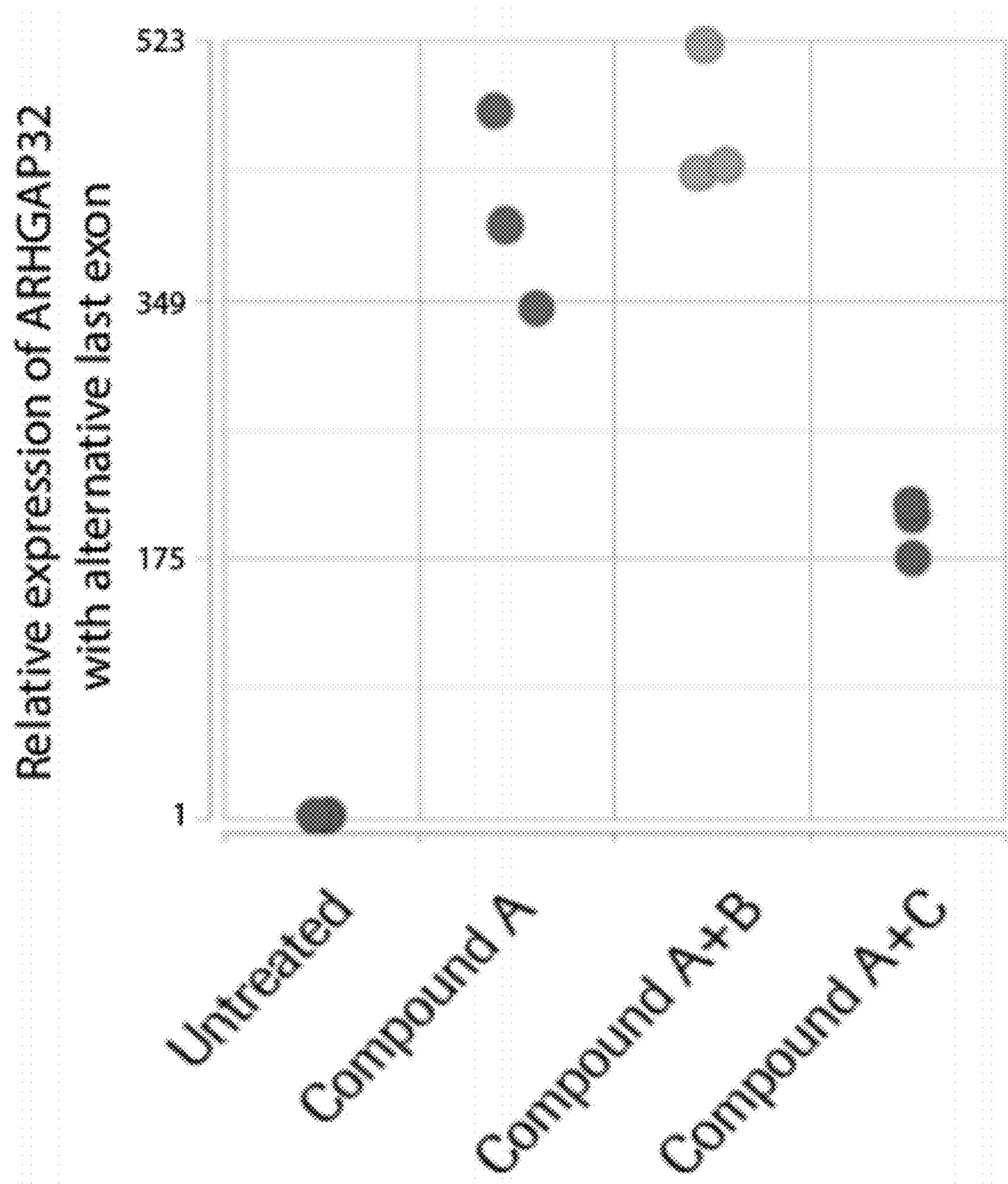

By thorough investigation of the called alternative transcripts, another gene name previously shown to be involved neuronal development and maintenance. This gene, ARHGAP32 encodes the Rho GTPase-activating protein 32, which is expressed primarily in the brain and has been shown to be involved proper neuronal development and maintenance. Knockdown of TDP-43 results in the use of an alternative splice acceptor site at pos. Chr11:128992046 (resulting in an alternative last exon in ENSG00000134909 position 200153 in the gene, experimentally validated as shown in FIG. 7, and illustrated with reference to the ARHGAP32 pre-mRNA sequence in FIG. 8—the alternative splice site is indicated by ^, note only a fragment of the ARHGAP32 pre-mRNA is shown in FIG. 8, also disclosed herein as SEQ ID NO: 35). The new exon created by the use of the alternative splice site also contains two possible polyadenylation site 2471 and 2532 nts downstream of the splice acceptor site (See FIG. 8, shaded text), respectively. The treatment of Glutaneurons where TDP-43 have been reduced with TARDBP gapmer (i.e. TDP-43 depleted cells), shows that addition of an oligonucleotide of the invention (compound C) reduces the usage of the alternative splice acceptor site, whereas the STMN2 targeting mixmer (compound B) did not have any effect (FIG. 7). The second polyadenylation site illustrated in FIG. 8 is preceded by GU-repeat RNA binding protein sequence that is the potential TDP-43 binding site (FIG. 8). The consequence of the use of the alternative splice acceptor site, is that it generates a C-terminal truncated ARHGAP32 protein—resulting in a truncation of Rho GTPase-activating protein 32, as the open reading frame contains a stop codon in the new last exon of this variant. The new protein variant is 390 amino acids long with 6 new amino acids in the C-terminus, compared to wild type Rho GTPase-activating protein 32 which is 2,087 amino acids long. The majority of the Rho-GAP domain is lacking in this variant. The C-terminal part of wild type Rho GTPase-activating protein 32 which is also lacking has been shown to directly interact with TrkA, a high-affinity receptor for nerve growth factor (NGF), that regulates neuronal outgrowth.

SLC5A7

Figure 9A:
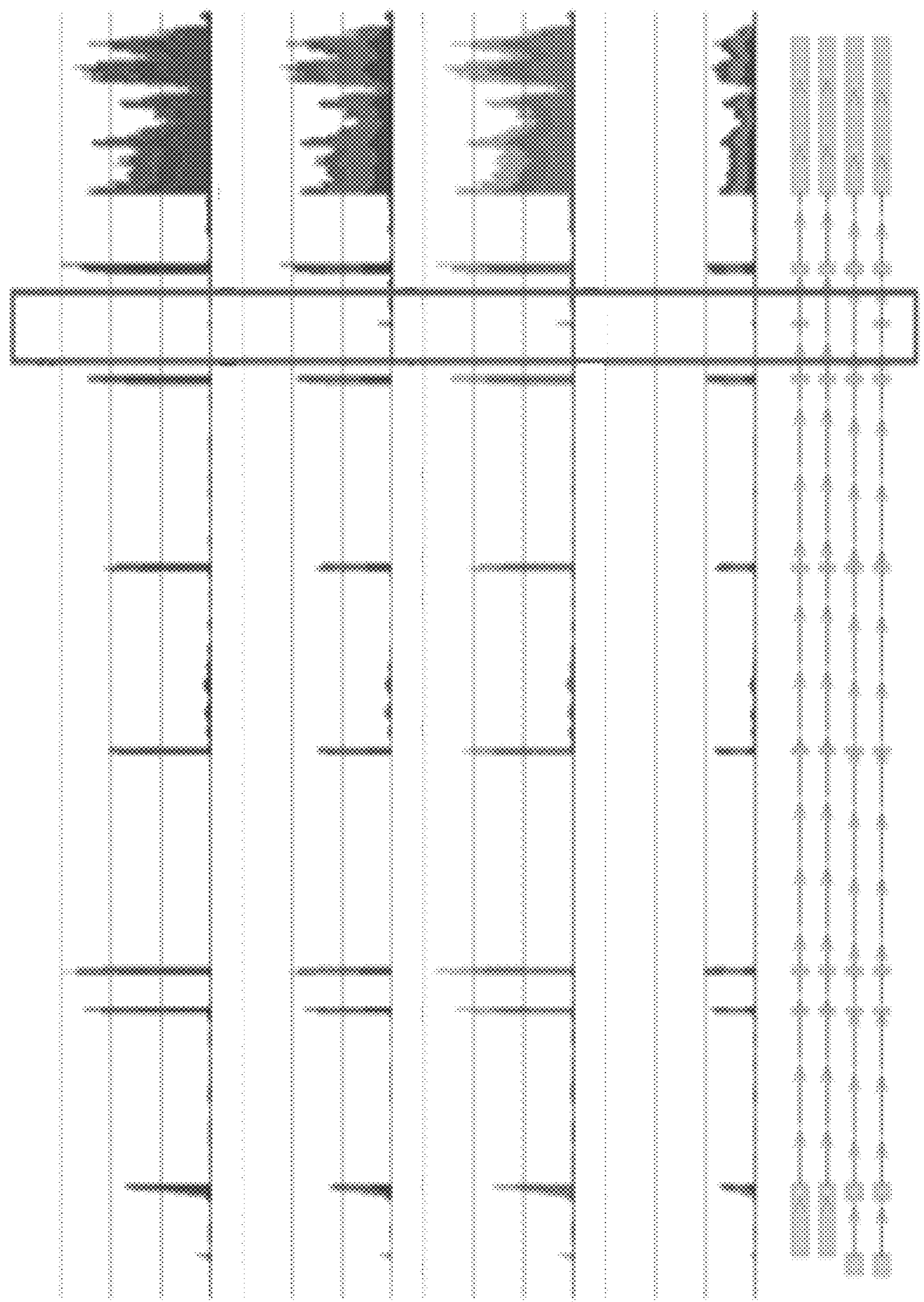
FIGS. 9A and 9B—SLC5A7 expression in Glutaneurons upon treatment with compound A, B and C.
Figure 9B:
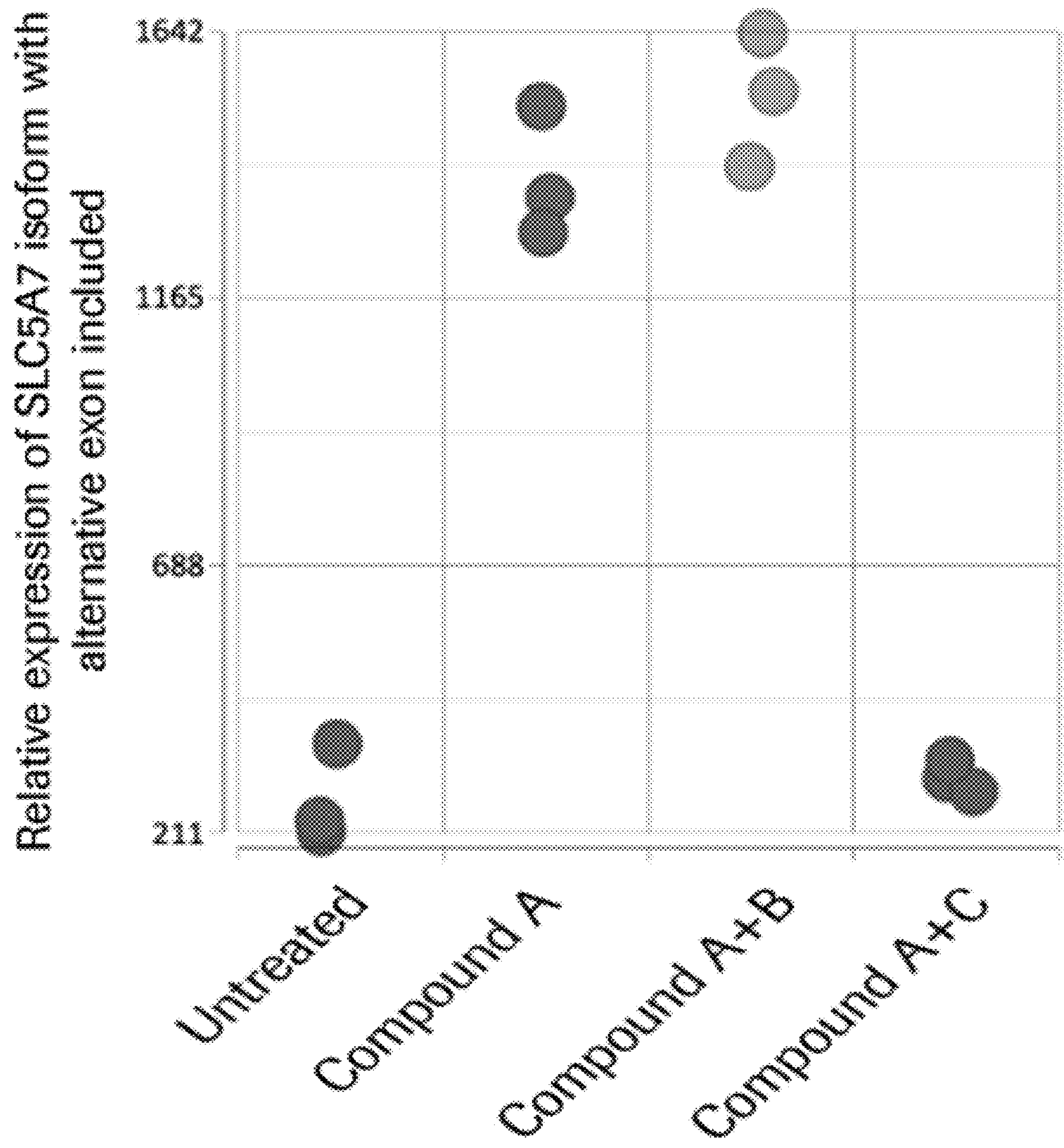

Another pre-mRNA that shows alternative splice is the SLC5A7 transcript encoding High affinity choline transporter 1. Loss of TDP-43 protein increases the use of a splice acceptor site (chr2:108,007,307) and a splice donor site (chr2:108,007,400) resulting in the inclusion of a novel exon with a length of 94 base pairs (chr2:108,007,307-108,007,400) (FIGS. 9A and 9B). As seen from the relative expression, the novel isoform increases more than 6-fold upon knock down of TDP-43 (Compound A). However, subsequent treatment with the TDP-43 mimicking ASO (Compound C) completely abolished the inclusion of this alternative exon, so the expression profile for this transcript variant resembles untreated cells (FIGS. 9A and 9B). The inclusion this exon results in a frameshift during translation and a premature stop codon within the novel exon, to generate a potential truncated variant of 326 amino acids (wild type protein is 580 amino acids long (Uniprot entry Q9GZV3). C-terminal truncations of High affinity choline transporter 1 (SLC5A7) has been shown to cause motor neuron defects, and in some cases an initial diagnosis of ALS (Salter et al. 2018; Neurol Genet. 2018 April; 4(2): e222). The protein consequence of this observed exon inclusion resembles the C-terminal truncations seen in these patients with mutations causing the C-terminal truncation.

CERT1

Figure 11A:
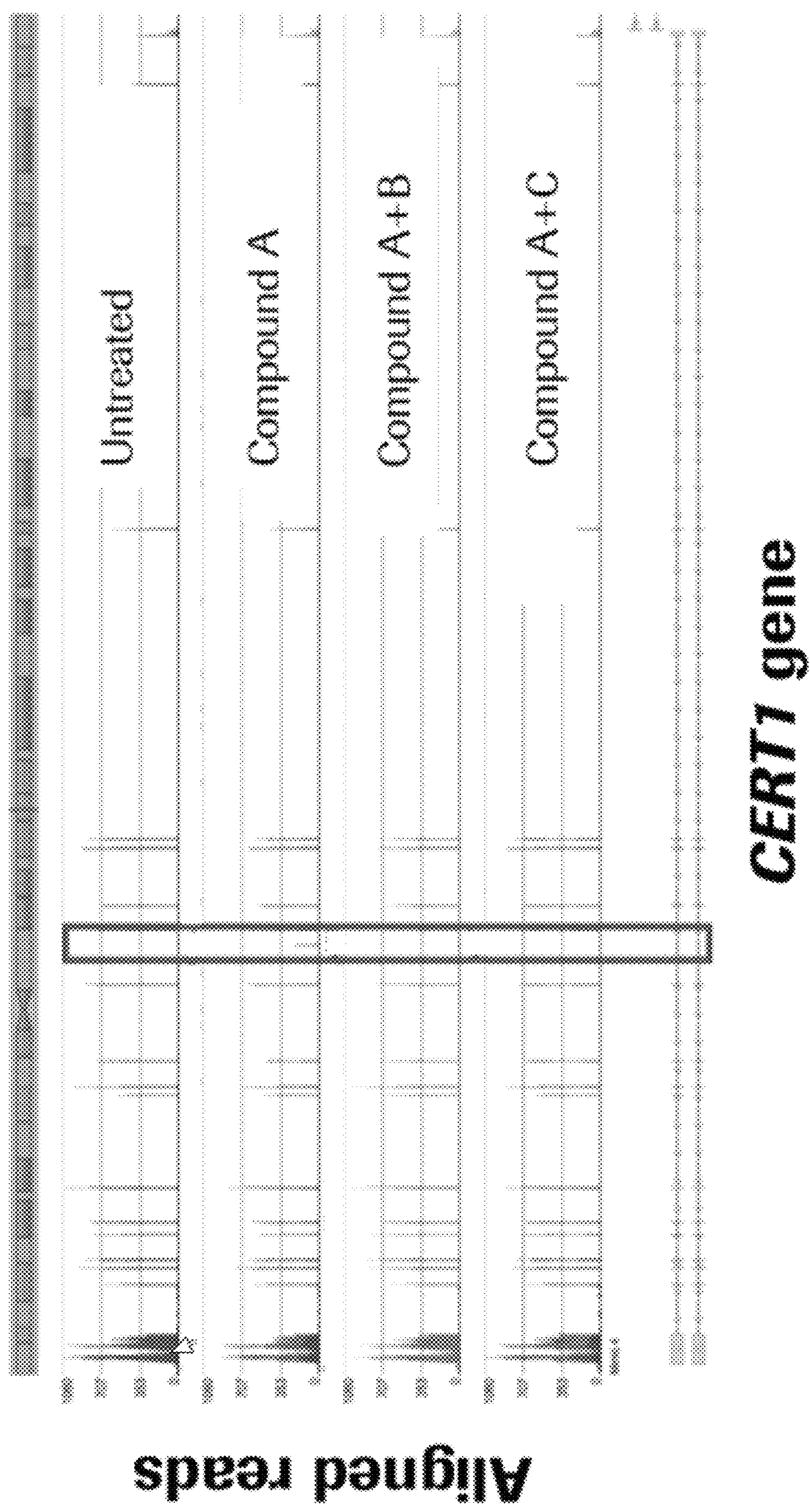
FIGS. 11A and 11B—CERT1 expression in Glutaneurons upon treatment with compound A, B and C.
Figure 11B:
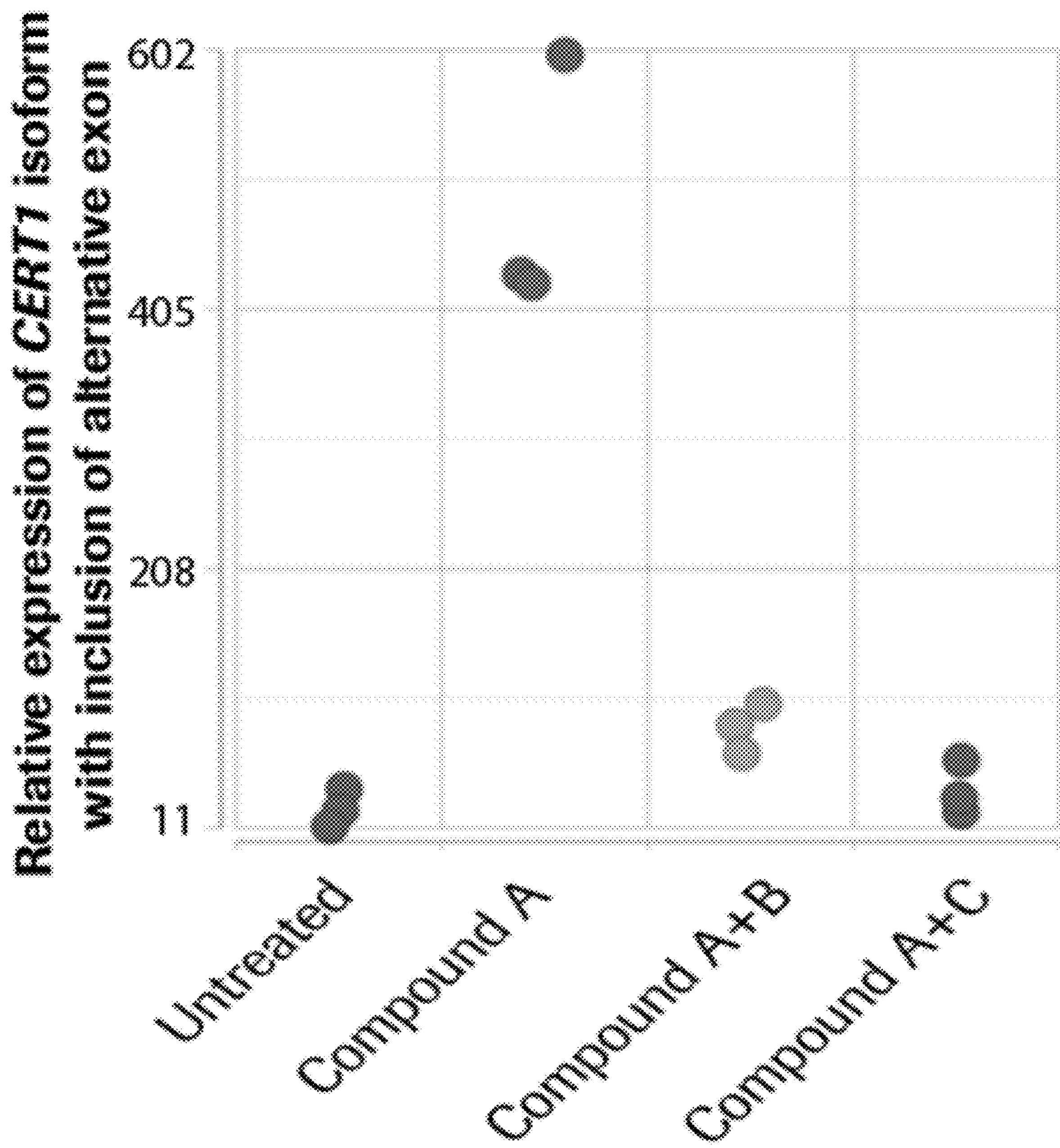

Another transcript that shows alternative splicing is the CERT1 mRNA encoding ceramide transfer protein or (CERT1). Loss of TDP-43 results in the use of a new splice donor and splice acceptor site to include a novel exon located at hg38 chr5:7541 51 97-7541 5235 (position 96395-96433 in ENSG00000113163)(FIGS. 11A-11B and 12). Loss of TDP-43 (compound A) increases novel isoform approximately 18-fold, whereas subsequent treatment with both the STMN2 ASO (Compound A+B) and the TDP-43 mimicking ASO (Compound A+C) remove the inclusion of this novel in frame exon to resemble wild type cells (FIGS. 11A and 11B). Within the pre-mRNA the cryptic exon is followed by a number of potential TDP-43 binding sites (FIG. 12). The cryptic exon is 39 bp in length and thereby does not change the ORF, but introduces 13 amino acids within the ceramide transfer protein (CERT1). The consequence of this is unknown. CERT1 is responsible for the transfer of ceramide from the endoplasmic reticulum (ER) to the Golgi apparatus. Ceramide is synthesized at the ER, then is transferred by CERT1 to Golgi where it is converted to sphingomyelin. Sphingomyelin is a type of sphingolipid found in animal cell membranes, especially in the membranous myelin sheath that surrounds some nerve cell axons. Regulation of the ceramide signaling pathways is involved in several neurodegenerative and neuroinflammatory diseases (Jana et a. J Neurol Sci. 2009 Mar. 15; 278(1-2):5-15).

To compare whether the TDP-43 targeting ASOs (Compound B and compound C) had similar targets, an analysis of alternative spliced transcripts from which a few selection criteria was set up. The p-value should be less than 0.01, and there should be more than a 2-fold change compared to the control analysis. The number of transcripts that shows alternative splicing upon knock down of TARDBP (Compound A versus untreated cells) is 749, whereas the number of transcripts that where alternative spliced using the STMN2 targeting ASO after initial TARDBP KD was 691 transcripts (compound A+B versus compound A). Of these 691 alternatively expressed transcripts, 483 were overlapping with the transcripts identified from TDP-43 KD. Finally, a comparison of the TDP-43 mimicking ASO after TARDBP Knock-down (KD, TDP-43 depletion) was compared to the TARDBP KD (compound A+C versus compound A). That revealed 502 alternatively spliced transcripts that were the same as seen in the initial TDP-43 KD versus untreated cells (FIG. 13). This analysis indicates that the antisense oligonucleotides of the invention have a more global effect on modulating RNA splicing as compared to compounds which are targeted specifically to STMN2, a result which is entirely consistent with the specific transcript analysis for ARHGAP32, SLC5A7 and CERT1 where the STMN2 specific compound B was not able to correct the aberrant splicing caused by TDP-43 depletion, whereas the compounds of the present invention were effective.

Example 3: Rescue of Erroneous mRNA Splicing Caused by the Lack of TDP43 Using CA-Repeat ASO Here we show the ability of CA-repeat antisense oligonucleotides to induce proper splicing on some TDP43 targets (STMN2, KALRN, CAMK2B, CERT1 and UNC13A).

CAMK2B

Another pre-mRNA that shows alternative splicing is the CAMK2B transcript encoding calcium/calmodulin-dependent protein kinase type II subunit beta, and is involved in dendritic spine and synapse formation and neuronal plasticity. CAMK2B is located on chromosome 7:44217150-44334577:-1 (hg38)(Ensembl entry ENSG00000058404).

Figure 14A:
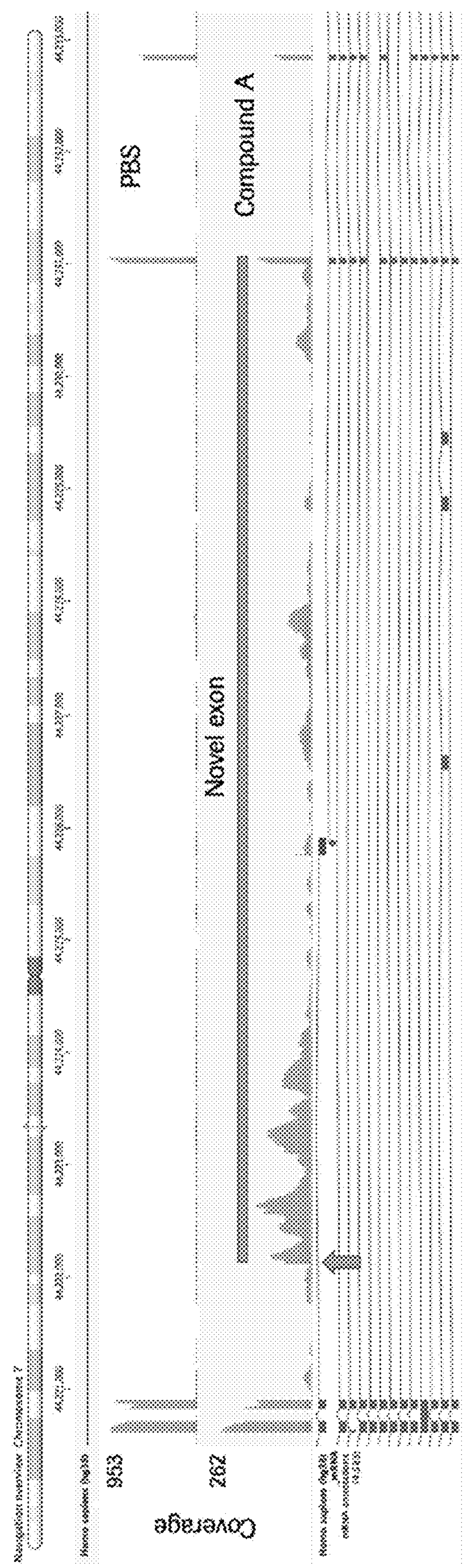

Loss of TDP43 protein decreases the use of the canonical splice donor site at position chr7:44,231,004-44,231,005, and results in an extended exon. Within this sequence, a novel splice acceptor site is also used upon loss of TDP43 protein located at chr7:44,222,113-44,222,114. The novel exon is therefore located on chr7: 44,222,115-44,231,054. This exon is 8938 nucleotides long, and contains a large number of stop codons, resulting in nonsense mediated decay of the CAMK2B mRNA (FIG. 14B).

KALRN

KALRN gene (Ensembl entry ENSG00000160145) is located on chromosome 3 (Chromosome 3: 124,033,369-124,726,325) (hg38). KALRN encodes kalirin RhoGEF kinase, also known as Huntingtin-associated protein-interacting protein, Protein Duo or Serine/threonine-protein kinase with Dbl- and pleckstrin homology domain.

Figure 15A:
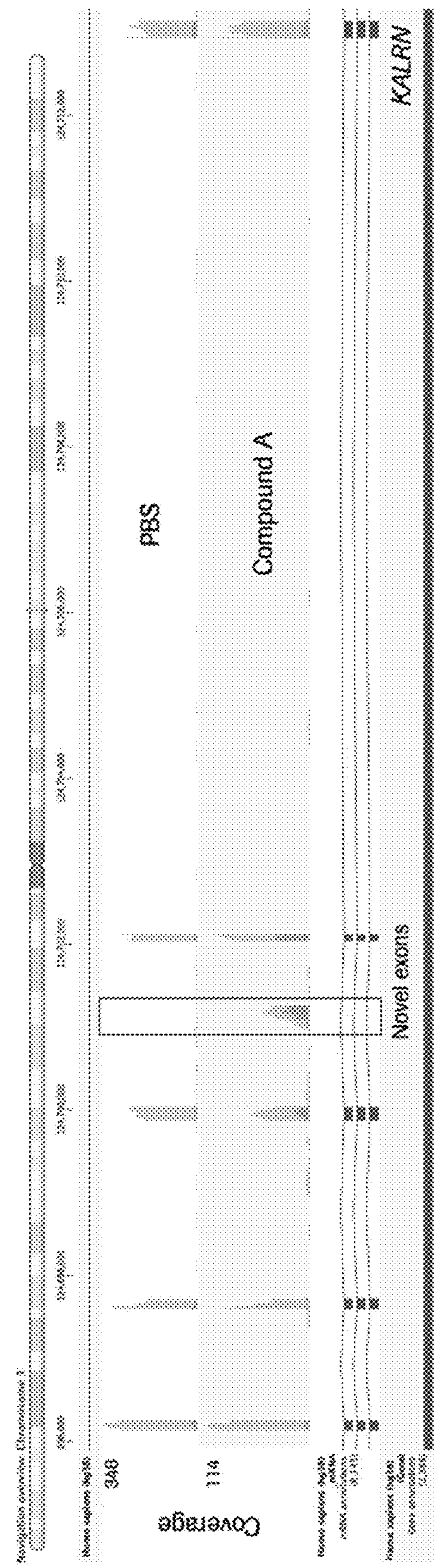
Figure 15B:
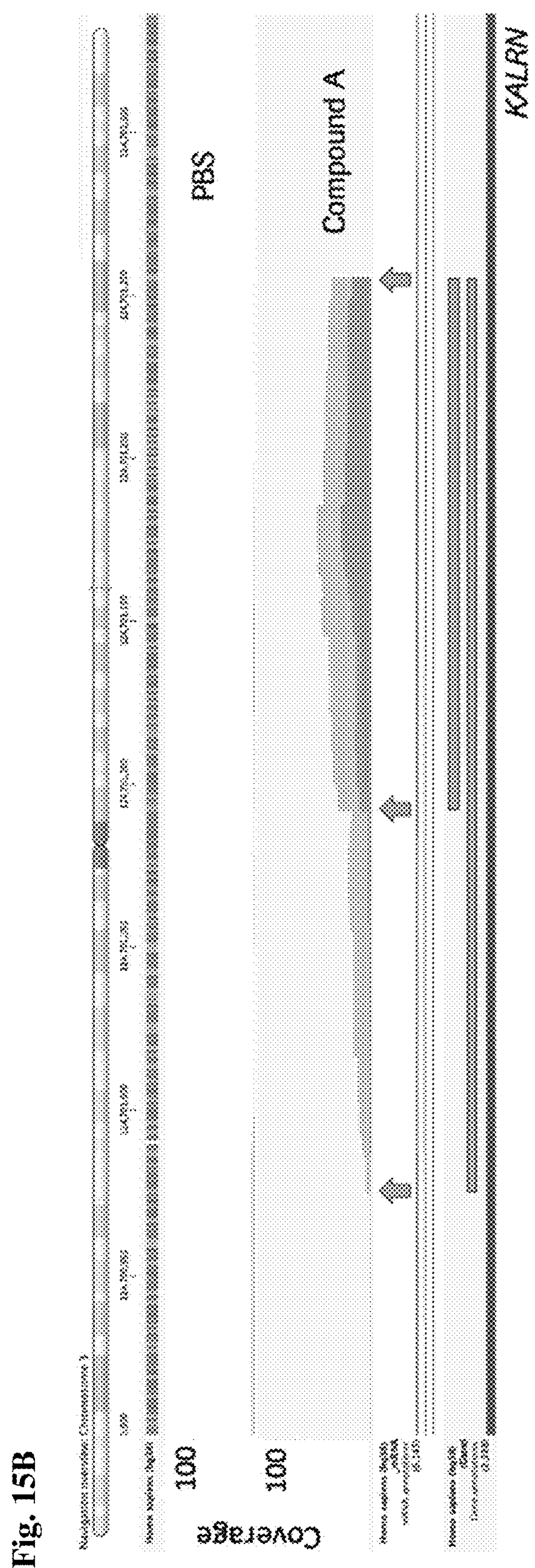

Loss of TDP43 protein increases the use of two novel alternative splice acceptor sites within KALRN pre-mRNA (chr3:124,700,977; AG positioned at chr3:124,700,975-124,700,976) and a splice donor site located (chr3:124,701,255, GT positioned at chr3:124,701,256-124,701,257)(FIGS. 15A and 15B). This results in the inclusion of a novel exon of 279 nucleotides (chr3:124,700,977-124,701,255), which potentially encodes 93 amino acids. However, as seen from FIG. 15C, the ORF quickly enters a nonsense codon shown in italic and underlined TGA.

UNC13A

UNC13A encodes Protein unc-13 homolog A. The UNC13A gene (Ensembl entry, ENSG00000130477) is located on chromosome 19:17601336-17688365:-1 (hg38) (minus strand). Protein unc-13 homolog A is involved in neurotransmitter release by acting in synaptic vesicle priming prior to vesicle fusion and participates in the activity-dependent refilling of readily releasable vesicle pool (RRP). Essential for synaptic vesicle maturation in most excitatory/glutamatergic but not inhibitory/GABA-mediated synapses (UniProt). Variants within the UNC13A gene have long been known to increase risk of amyotrophic lateral sclerosis (ALS) and frontotemporal dementia (FTD), and in two recent papers the inclusion of a cryptic exon upon TDP43 loss was described (Anna-Leigh Brown et al, "Common ALS/FTD risk variants in UNC13A exacerbate its cryptic splicing and loss upon TDP-43 mis-localization" bioRxiv 2021.04.02.438170; doi.org/10.1101/2021 04.02.438170; X. Rosa Ma et al., TDP-43 represses cryptic exon inclusion in FTD/ALS gene UNC13A, bioRxiv 2021.04.02.438213; doi.org/10.1101/2021.04.02.438213). Furthermore, two known polymorphisms strongly associated with ALS/FTD risk which alter TDP-43 binding within UNC13A pre-mRNA and thereby lead to inclusion of the cryptic exon Brown et al, 2021).

Figure 16B:
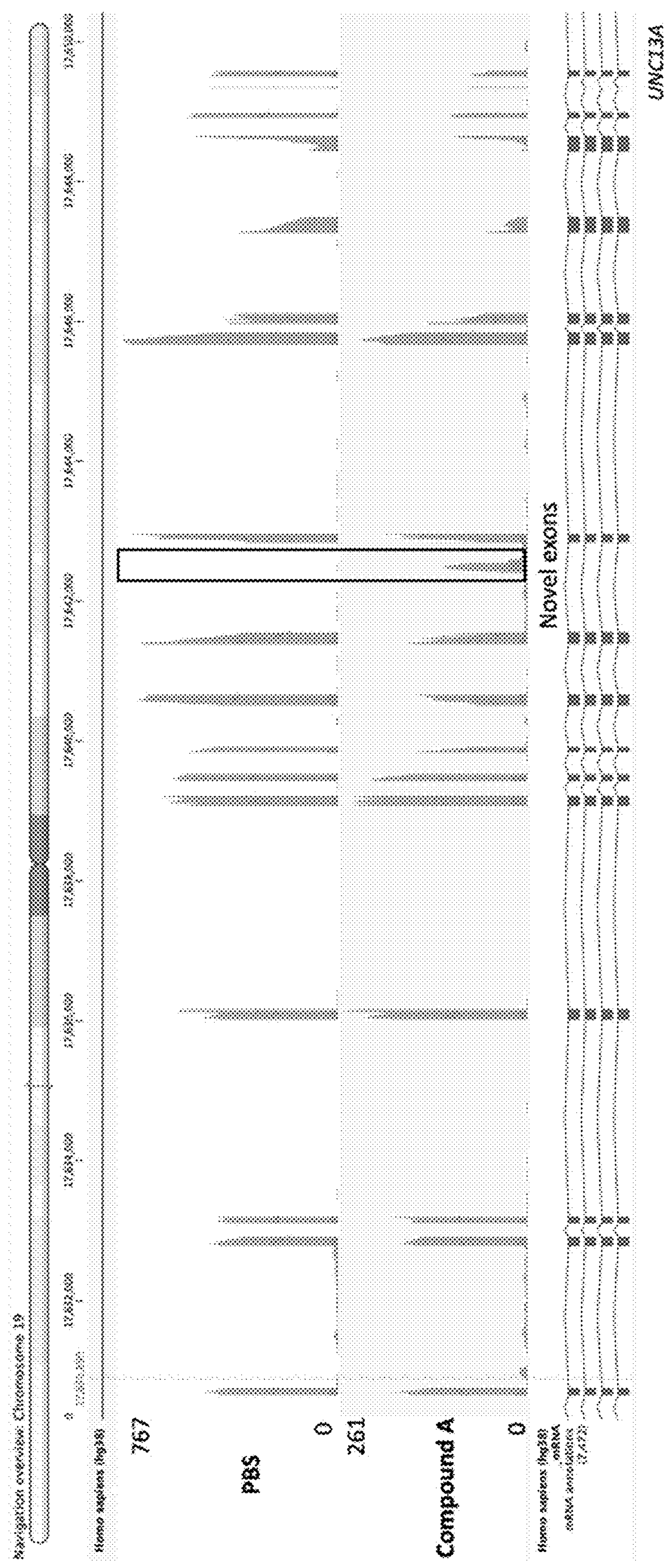
Figure 16C:
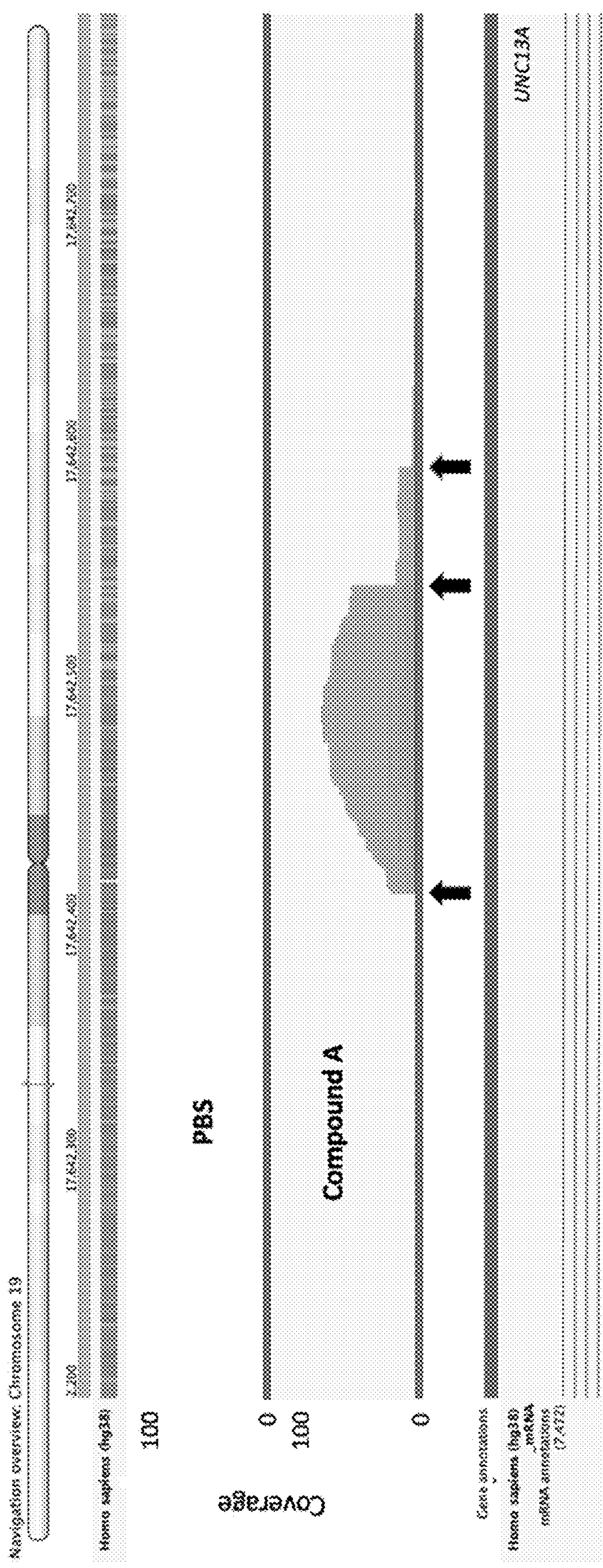

Our data shows in a similar way inclusion of the cryptic exons described by Brown et al, 2021 as described below. Upon TDP43 loss, two exons within UNC13A are observed by usage of alternative splice acceptor and splice donor sites. One exon is 128 nucleotides in length and is located on chromosome 19:17,642,414-17,642,541, and the other is 178 nucleotides in length and is located on chromosome 19:17,642,414-17,642,591 (FIG. 16A). The two exons are overlapping and use the same splice acceptor site chr19:17,642,414, whereas the splice donor sites differ, chr19:17,642,591 and chr19:17,642,541, respectively (FIGS. 16B and 16C). Both exons are disrupting the open reading frame of UNC13A (FIG. 16A).

Human glutamatergic neurons (Fujifilms) were plated at 60000 cells per 96-well plates coated with Laminin and Poly(ethyleneimine) solution (Sigma Aldrich) in 200 ul Culture medium on Day 0. Half the cell culture medium was changed 3 times a week during the whole experiment (day 1,5,8,11,13,15). To knockdown TDP-43, compound A (SEQ ID 19,1) was added to the culture medium at 5 μM on day 1 and day 8 (Except for two control wells). The CA-repeat antisense oligonucleotide was added to the culture medium on day 5 and day 13 at 10 μM. 48 different CA-repeat antisense oligonucleotides were added in total. 12 wells received only the compound A (Compound #19.1) to serve as a baseline reference.

The cells were harvested on day 18 using Magnapure lysis buffer (Roche) and RNA was isolated on MagNA pure 96 system (Roche) according to the manufacturer's instructions including DNase treatment step. The purified RNA was denatured 30 seconds at 90° C. before cDNA synthesis. cDNA was created using the iScript Advanced cDNA Synthesis Kit for RT-qPCR (Biorad) according to the manufacturer's instructions.

Measurements of the expression levels of the target genes was done by droplet digital PCR using the QX1 system (Bio-Rad). The PCR-probe assays used to measure the expressed of normally spliced target mRNA was designed to span the two exons, where in-between the new "mutant" exon would occur.

Data shown in Results Table B was normalized to the expression of the house keeping gene HPRT1, and finally normalized to the average expression value of the two control wells (PBS) that did not receive any TDP43 knockdown or CA-repeat antisense oligonucleotide.

The following PCR probe assay synthesized at (Integrated DNA technologies (IDT)) were used:

```
TARDBP
Primer 1:
                                        (SEQ ID NO: 44)
CAGCTCATCCTCAGTCATGTC

Primer 2:
                                        (SEQ ID NO: 45)
GATGGTGTGACTGCAAACTTC

Probe:
                                        SEQ ID NO: 104)
/5Cy5/CAGCGCCCCACAAACACTTTTCT/3IAbRQSp/

STMN2
Primer 1:
                                       (SEQ ID NO: 105)
CTGCTCAGCGTCTGC

Primer 2:
                                       (SEQ ID NO: 106)
GTTGCGAGGTTCCGG

Probe:
                                       (SEQ ID NO: 107)
/5HEX/CTAAAACAG/ZEN/CAATGGCCTACAAGGAAAAAATGAAG/

3IABkFQ/

CERT1
Primer 1:
                                       (SEQ ID NO: 108)
CTAATGGTTAAACGTGAGGACAGC
```

-continued

Primer 2:

(SEQ ID NO: 109)

ATCTGGTCCTCCAAAGTGGG

Probe:

(SEQ ID NO: 110)

/5HEX/CAGAAGAGA/ZEN/CTGGATAAGGAAACTGAGAAGAAAAGAAGA

ACAG/3IABkFQ/

KALRN
Primer 1:

(SEQ ID NO: 111)

CGAGCCCTCGGAGTTTG

Primer 2:

(SEQ ID NO: 112)

TCCTTCCAAGAAATGGTGGC

Probe:

(SEQ ID NO: 113)

/5HEX/CGACTTCCA/ZEN/GAATATGATGCTGCTGCTGATG/

3IABkFQ/

CAMK2B
Primer 1:

(SEQ ID NO: 114)

CTGACAGTGCCAATACCACC

-continued

Primer 2:

(SEQ ID NO: 115)

GCTGCTCCGTGGTCTTAAT

Probe:

(SEQ ID NO: 116)

/5Cy5/ATGAAGACGCTAAAGCCCGGAAGCAG/3IAbRQSp/

UNC13A
Primer 1:

(SEQ ID NO: 117)

GATCAAAGGCGAGGAGAAGG

Primer 2:

(SEQ ID NO: 118)

TGGCATCTGGGATCTTCAC

Probe:

(SEQ ID NO: 119)

/56-FAM/ACCTGTCTG/ZEN/CATGAGAACCTGTTCCACTTC/

3IABkFQ/

The following CY5.5 labelled HPRT1 probe was purchased from BioRad: dHsaCPE13136107.

RESULTS TABLE B: Displays the expression value of the genes TARDBP, STMN2, CERT1, CAMK2B, KALRN and UNC13A, Expression is displayed as percentage expression compared to the average of untreated glutaneurons (PBS). As can be seen, several of the CA repeat antisense oligonucleotides are capable of elevating the expression of the target genes, compared to cells only treated with the TDP43 knockdown antisense oligonucleotide TDP43 KD (Seq ID 19,1).

Results Table B

| Compound | SEQ ID NO | Base sequence | Rescue Compound class | TARDBP | STMN2 | CERT1 | CAMK2B | UNC13A | KALRN |
|---|---|---|---|---|---|---|---|---|---|
| TDP43 KD | 19.1 | | | 2.5 | 44.0 | 75.9 | 21.7 | 50.4 | 1.2 |
| TDP43 KD | 19.1 | | | 2.0 | 35.8 | 60.6 | 21.9 | 35.4 | 2.2 |
| TDP43 KD | 19.1 | | | 2.2 | 45.9 | 63.6 | 20.7 | 42.4 | 0.0 |
| TDP43 KD | 19.1 | | | 2.2 | 46.4 | 68.2 | 16.4 | 40.9 | 1.4 |
| TDP43 KD | 19.1 | | | 1.6 | 44.9 | 60.5 | 22.1 | 48.3 | 1.9 |
| TDP43 KD | 19.1 | | | 2.1 | 42.2 | 60.9 | 21.5 | 38.6 | 2.1 |
| TDP43 KD | 19.1 | | | 2.2 | 39.6 | 56.7 | 16.8 | 37.0 | 1.3 |
| TDP43 KD | 19.1 | | | 1.7 | 46.7 | 51.4 | 18.7 | 26.7 | 1.1 |
| TDP43 KD | 19.1 | | | 2.1 | 39.4 | 59.7 | 16.9 | 43.3 | 1.8 |
| TDP43 KD | 19.1 | | | 1.4 | 39.5 | 64.8 | 19.3 | 34.4 | 2.2 |
| TDP43 KD | 19.1 | | | 3.3 | 45.3 | 69.3 | 20.3 | 41.1 | 1.6 |
| TDP43 KD | 19.1 | | | 3.8 | 46.0 | 79.9 | 25.4 | 47.2 | 0.9 |
| PBS | | | | 91.0 | 92.7 | 92.9 | 91.2 | 95.2 | 112.5 |
| PBS | | | | 109.0 | 107.3 | 107.1 | 108.8 | 104.8 | 87.5 |
| SEQ ID 20 | 20 | CACACACACACACACACACAC | LNA mixmer | 1.7 | 152.4 | 128.6 | 89.6 | 78.6 | 53.6 |
| SEQ ID 21 | 21 | ACACACACACACACACACACAC | LNA mixmer | 2.8 | 48.1 | 96.7 | 28.8 | 41.5 | 8.0 |
| SEQ ID 22 | 22.1 | CACACACACACAACACACACACAC | LNA mixmer | 2.7 | 74.9 | 132.0 | 37.6 | 29.2 | 19.3 |
| SEQ ID 22 | 22.2 | CACACACACACAACACACACACAC | LNA mixmer | 1.6 | 37.0 | 78.2 | 25.8 | 23.6 | 4.7 |

-continued

| Results Table B | | | | | | | | | |
|---|---|---|---|---|---|---|---|---|---|
| Compound | SEQ ID NO | Base sequence | Rescue Compound class | TARDBP | STMN2 | CERT1 | CAMK2B | UNC13A | KALRN |
| SEQ ID 23 | 23.6 | CACACACACACACACACACACAC | LNA mixmer | 2.0 | 83.2 | 113.7 | 37.3 | 60.8 | 5.8 |
| SEQ ID 23 | 23.7 | CACACACACACACACACACACAC | LNA mixmer | 2.0 | 95.7 | 96.1 | 25.9 | 25.7 | 6.0 |
| SEQ ID 23 | 23.8 | CACACACACACACACACACACAC | LNA mixmer | 3.4 | 71.1 | 121.0 | 42.6 | 48.0 | 21.7 |
| SEQ ID 23 | 23.9 | CACACACACACACACACACACAC | LNA mixmer | 1.9 | 81.3 | 115.5 | 35.4 | 51.5 | 15.1 |
| SEQ ID 24 | 24 | ACACACACACACACACACACACAC | LNA mixmer | 3.3 | 50.3 | 101.3 | 25.2 | 34.1 | 7.1 |
| SEQ ID 25 | 25.1 | CACACACACACACACACACACACAC | LNA mixmer | 2.2 | 87.1 | 113.9 | 37.7 | 47.6 | 14.6 |
| SEQ ID 25 | 25.2 | CACACACACACACACACACACACAC | LNA mixmer | 1.7 | 90.1 | 110.1 | 27.5 | 35.2 | 6.8 |
| SEQ ID 25 | 25.3 | CACACACACACACACACACACACAC | LNA mixmer | 2.7 | 56.4 | 100.3 | 34.2 | 42.7 | 16.4 |
| SEQ ID 25 | 25.4 | CACACACACACACACACACACACAC | LNA mixmer | 2.9 | 86.9 | 97.0 | 34.0 | 49.7 | 16.4 |
| SEQ ID 26 | 26 | ACACACACACACACACACACACACAC | LNA mixmer | 2.6 | 51.6 | 98.8 | 28.7 | 46.0 | 7.7 |
| SEQ ID 27 | 27.1 | CACACACACACACACACACACACACA | LNA mixmer | 2.3 | 88.2 | 118.9 | 36.8 | 65.3 | 14.4 |
| SEQ ID 27 | 27.2 | CACACACACACACACACACACACACA | LNA mixmer | 1.9 | 70.7 | 115.3 | 33.1 | 52.7 | 11.9 |
| SEQ ID 27 | 27.3 | CACACACACACACACACACACACACAC | LNA mixmer | 2.7 | 58.9 | 97.5 | 31.1 | 53.3 | 8.3 |
| SEQ ID 27 | 27.4 | CACACACACACACACACACACACACAC | LNA mixmer | 2.4 | 90.8 | 119.9 | 30.7 | 32.7 | 3.7 |
| SEQ ID 28 | 28 | ACACACACACACACACACACACACACAC | LNA mixmer | 1.8 | 41.6 | 94.0 | 29.1 | 43.2 | 8.5 |
| SEQ ID 29 | 29.1 | CACACACACACACACACACACACACACAC | LNA mixmer | 3.3 | 63.6 | 87.4 | 26.7 | 35.7 | 12.8 |
| SEQ ID 29 | 29.2 | CACACACACACACACACACACACACACAC | LNA mixmer | 3.4 | 70.9 | 123.3 | 34.3 | 46.1 | 7.9 |
| SEQ ID 29 | 29.3 | CACACACACACACACACACACACACACAC | LNA mixmer | 2.1 | 48.3 | 90.0 | 23.8 | 45.7 | 13.7 |
| SEQ ID 29 | 29.4 | CACACACACACACACACACACACACACA C-3' | LNA mixmer | 3.0 | 48.4 | 116.6 | 22.4 | 20.6 | 7.6 |
| SEQ ID 30 | 30 | 5'-ACACACACACACACACCACACACACA CACACA | LNA mixmer | 2.2 | 57.5 | 108.9 | 27.3 | 32.3 | 2.1 |
| SEQ ID 31 | 31.1 | CACACACACACACACACACACACACACAC ACA-3' | LNA mixmer | 2.6 | 61.7 | 105.6 | 29.7 | 45.1 | 10.2 |
| SEQ ID 31 | 31.2 | CACACACACACACACACACACACACACAC ACA | LNA mixmer | 3.2 | 58.7 | 110.4 | 25.3 | 31.7 | 9.6 |
| SEQ ID 32 | 32 | CACACACACACACACAACACACACACACA CACAC | LNA mixmer | 2.5 | 59.0 | 98.4 | 26.8 | 26.6 | 8.3 |
| SEQ ID 33 | 33 | ACACACACACACACACCACACACACACAC ACACA | LNA mixmer | 1.7 | 57.7 | 79.6 | 23.7 | 38.8 | 3.0 |
| SEQ ID 22 | 22.3 | CACACACACACAACACACACACAC | MOE | 2.2 | 60.6 | 100.3 | 31.6 | 55.3 | 12.3 |
| SEQ ID 23 | 23.1 | CACACACACACACACACACACAC | MOE | 2.7 | 89.0 | 90.4 | 29.0 | 35.7 | 24.9 |
| SEQ ID 25 | 25.5 | CACACACACACACACACACACACAC | MOE | 1.9 | 79.5 | 103.1 | 28.8 | 45.6 | 16.4 |
| SEQ ID 27 | 27.5 | CACACACACACACACACACACACACAC | MOE | 3.0 | 91.3 | 95.3 | 24.9 | 37.8 | 22.5 |
| SEQ ID 29 | 29.5 | CACACACACACACACACACACACACACAC | MOE | 2.5 | 87.3 | 109.4 | 30.8 | 37.4 | 18.1 |
| SEQ ID 23 | 23.2 | CACACACACACACACACACACAC | MOE mixmer | 4.3 | 36.1 | 75.8 | 25.9 | 37.8 | 1.5 |
| SEQ ID 25 | 25.6 | CACACACACACACACACACACACAC | MOE mixmer | 3.4 | 37.9 | 69.1 | 20.3 | 37.2 | 1.0 |
| SEQ ID 23 | 23.3 | CACACACACACACACACACACAC | MOE mixmer | 2.5 | 56.4 | 100.5 | 25.4 | 53.9 | 5.5 |

-continued

Results Table B

| Compound | SEQ ID NO | Base sequence | Rescue Compound class | TARDBP | STMN2 | CERT1 | CAMK2B | UNC13A | KALRN |
|---|---|---|---|---|---|---|---|---|---|
| SEQ ID 25 | 25.7 | CACACACACACACACACACACACAC | MOE mixmer | 2.0 | 52.7 | 101.9 | 24.2 | 42.1 | 5.2 |
| SEQ ID 27 | 27.6 | CACACACACACACACACACACACACAC | MOE mixmer | 3.2 | 42.2 | 93.1 | 27.2 | 51.9 | 1.2 |
| SEQ ID 27 | 27.7 | CACACACACACACACACACACACACAC | MOE mixmer | 2.2 | 58.0 | 97.3 | 24.9 | 44.0 | 1.8 |
| SEQ ID 29 | 29.6 | CACACACACACACACACACACACACACAC | MOE mixmer | 3.4 | 31.3 | 62.2 | 14.0 | 19.1 | 1.3 |
| SEQ ID 29 | 29.7 | CACACACACACACACACACACACACACAC | MOE mixmer | 2.4 | 60.2 | 97.6 | 26.0 | 41.7 | 5.3 |
| SEQ ID 23 | 23.4 | CACACACACACACACACACACAC | 2'O-Methyl | 2.9 | 42.5 | 96.4 | 26.2 | 43.0 | 3.2 |
| SEQ ID 25 | 25.8 | CACACACACACACACACACACACAC | 2'O-Methyl | 3.3 | 49.3 | 106.6 | 28.2 | 45.9 | 3.2 |
| SEQ ID 27 | 27.8 | CACACACACACACACACACACACACAC | 2'O-Methyl | 2.9 | 46.8 | 104.1 | 29.1 | 52.4 | 1.1 |
| SEQ ID 29 | 29.8 | CACACACACACACACACACACACACACAC | 2'O-Methyl | 2.4 | 46.2 | 96.5 | 27.1 | 33.9 | 1.0 |
| SEQ ID 23 | 23.5 | CACACACACACACACACACACAC | 2'O-Methyl Mixmer | 2.6 | 31.7 | 72.1 | 17.6 | 25.7 | 2.0 |
| SEQ ID 25 | 25.9 | CACACACACACACACACACACACAC | 2'O-Methyl Mixmer | 3.0 | 40.7 | 85.7 | 17.3 | 27.5 | 0.3 |
| SEQ ID 27 | 27.9 | CACACACACACACACACACACACACAC | 2'O-Methyl Mixmer | 3.5 | 44.5 | 102.3 | 22.2 | 40.2 | 1.9 |
| SEQ ID 29 | 29.9 | CACACACACACACACACACACACACACAC | 2'O-Methyl Mixmer | 2.4 | 42.3 | 85.0 | 15.7 | 37.7 | 1.4 |
| SEQ ID 34 | 34 | ACACACACACACACACACACACACACACA C | 2'O-Methyl Mixmer | 2.4 | 52.0 | 110.4 | 30.1 | 40.4 | 9.2 |

Example 4—Rescue of Erroneous mRNA Splicing Caused by the Lack of TDP43 Using CA-Repeat Rich ASOs In order to illustrate that CA-repeat ASO containing some sequence variations are still capable of correcting erroneous mRNA splicing caused by the lack of TDP43, we produced CA-repeat ASO with up to 5 nucleotide changes and show that they are still capable of correcting mRNA splicing. These CA-repeat rich ASOs are tested for their ability to induce proper splicing on 3 known TDP43 targets (STMN2, KALRN, CAMK2B) in absence of TDP43.

Human glutamatergic neurons (Fujifilms) were plated at 60000 cells per 96-well plates coated with Laminin and Poly(ethyleneimine) solution (Sigma Aldrich) in 200 ul Culture medium on Day 0. Half the cell culture medium was changed 3 times a week during the whole experiment (day 1,3,6,8,10,13,15). To knockdown TDP-43, compound A (SEQ ID 19,1) was added to the culture medium at 5 µM on day 1 and day 8 (Except for four control wells). The CA-repeat rich ASOs were added to the culture medium on day 10 and day 13 at 10 µM. 60 different CA-repeat rich ASO were added, as indicated in Table C below. 10 wells received only the compound A (SEQ ID 19,1) to serve as a baseline reference.

The cells were harvested on day 16 using Magnapure lysis buffer (Roche) and RNA was isolation on MagNA pure 96 system (Roche) according to the manufacturer's instructions including DNase treatment step. The purified RNA was denatured 30 seconds at 90° C. before cDNA synthesis. cDNA was created using the iScript Advanced cDNA Synthesis Kit for RT-qPCR (Biorad) according to the manufacturer's instructions.

Measurements of the expression levels of the target genes were done by droplet digital PCR using the QX1 system (Bio-Rad). The PCR-probe assays used to measure the expression of normally spliced target mRNA was designed to span the two exons, where in-between the new "mutant" exon would occur.

Data shown in table C was normalized to the expression of the housekeeping gene HPRT1, and finally normalized to the average expression value of the two control wells (PBS) that did not receive any TDP43 knock-down or CA-repeat ASO.

The following PCR probe assay synthesized at (Integrated DNA technologies (IDT)) were used TARDBP:

```
Primer 1:
                                     (SEQ ID NO: 44)
CAGCTCATCCTCAGTCATGTC

Primer 2:
                                     (SEQ ID NO: 45)
GATGGTGTGACTGCAAACTTC
```

-continued

```
Probe:
                                   (SEQ ID NO: 104)
/5Cy5/CAGCGCCCCACAAACACTTTTCT/3IAbRQSp/)

STMN2:
Primer 1:
                                   (SEQ ID NO: 105)
CTGCTCAGCGTCTGC

Primer 2:
                                   (SEQ ID NO: 106)
GTTGCGAGGTTCCGG

Probe:
                                   (SEQ ID NO: 107)
/5HEX/CTAAAACAG/ZEN/CAATGGCCTACAAGGAAAAAATGAAG/

3IABkFQ/)

KALRN:
Primer 1:
                                   (SEQ ID NO: 111)
CGAGCCCTCGGAGTTTG

Primer 2:
                                   (SEQ ID NO: 112)
TCCTTCCAAGAAATGGTGGC

Probe:
                                   (SEQ ID NO: 113)
/5HEX/CGACTTCCA/ZEN/GAATATGATGCTGCTGCTGATG/
3IABkFQ/)

CAMK2B:
Primer 1:
                                   (SEQ ID NO: 114)
CTGACAGTGCCAATACCACC

Primer 2:
                                   (SEQ ID NO: 115)
GCTGCTCCGTGGTCTTAAT

Probe:
                                   (SEQ ID NO: 116)
/5Cy5/ATGAAGACGCTAAAGCCCGGAAGCAG/3IAbRQSp/)
```

The following CY5.5 labelled HPRT1 probe was purchased from BioRad: dHsaCPE13136107.

Results Table C—Displays the expression value of the genes: TDP43, CAMK2B, STMN2 and KALRN. Expression is displayed as percentage expression compared to the average of untreated glutaneurons (PBS).

RESULTS TABLE C

| Compound | SEQ ID NO | TDP43 | CAMK2B | STMN2 | KALRN |
|---|---|---|---|---|---|
| PBS | | 99.2 | 99.4 | 101.7 | 103.9 |
| PBS | | 94.9 | 99.8 | 91.5 | 80.6 |
| PBS | | 97.6 | 86.7 | 99.7 | 97.5 |
| PBS | | 108.2 | 114.2 | 107.1 | 118.0 |
| TDP43 KD | Seq ID 19.1 | 2.3 | 26.7 | 34.1 | 3.1 |
| TDP43 KD | Seq ID 19.1 | 0.9 | 28.5 | 30.2 | 2.3 |
| TDP43 KD | Seq ID 19.1 | 1.2 | 24.9 | 35.4 | 1.9 |
| TDP43 KD | Seq ID 19.1 | 1.0 | 22.5 | 35.6 | 1.8 |
| TDP43 KD | Seq ID 19.1 | 1.5 | 25.4 | 40.0 | 3.2 |
| TDP43 KD | Seq ID 19.1 | 1.5 | 25.3 | 36.1 | 1.1 |
| TDP43 KD | Seq ID 19.1 | 2.1 | 25.1 | 34.0 | 1.6 |
| TDP43 KD | Seq ID 19.1 | 2.1 | 26.9 | 35.4 | 1.6 |
| TDP43 KD | Seq ID 19.1 | 2.1 | 19.8 | 30.5 | 1.7 |
| TDP43 KD | Seq ID 19.1 | 2.2 | 19.3 | 32.6 | 2.2 |
| Seq ID 20 | Seq ID 20 | 2.2 | 32.6 | 42.5 | 6.7 |
| Seq ID 20 | Seq ID 20.2 | 2.1 | 31.6 | 53.8 | 21.8 |
| Seq ID 50 | Seq ID 50 | 1.9 | 27.4 | 36.5 | 8.6 |
| Seq ID 51 | Seq ID 51 | 2.1 | 36.4 | 46.8 | 9.3 |
| Seq ID 52 | Seq ID 52 | 2.4 | 35.8 | 46.4 | 18.7 |
| Seq ID 53 | Seq ID 53 | 2.9 | 28.1 | 45.6 | 7.8 |
| Seq ID 54 | Seq ID 54 | 1.6 | 33.3 | 37.2 | 5.8 |
| Seq ID 55 | Seq ID 55 | 2.7 | 28.3 | 48.5 | 17.2 |
| Seq ID 56 | Seq ID 56 | 2.4 | 41.1 | 62.5 | 14.3 |
| Seq ID 57 | Seq ID 57 | 2.0 | 31.9 | 53.6 | 6.0 |
| Seq ID 58 | Seq ID 58 | 2.6 | 35.3 | 54.9 | 5.7 |
| Seq ID 59 | Seq ID 59 | 2.3 | 27.3 | 38.1 | 11.7 |
| Seq ID 60 | Seq ID 60 | 2.9 | 37.7 | 49.5 | 11.8 |
| Seq ID 61 | Seq ID 61 | 2.0 | 29.4 | 33.5 | 3.0 |
| Seq ID 62 | Seq ID 62 | 2.6 | 28.0 | 53.1 | 4.4 |
| Seq ID 63 | Seq ID 63 | 2.6 | 27.8 | 42.0 | 4.7 |
| Seq ID 64 | Seq ID 64 | 2.0 | 34.6 | 37.8 | 6.7 |
| Seq ID 65 | Seq ID 65 | 2.3 | 30.6 | 47.2 | 12.4 |
| Seq ID 66 | Seq ID 66 | 2.7 | 31.4 | 38.6 | 3.9 |
| Seq ID 67 | Seq ID 67 | 3.0 | 33.6 | 42.5 | 4.7 |
| Seq ID 68 | Seq ID 68 | 3.0 | 33.9 | 44.9 | 8.9 |
| Seq ID 69 | Seq ID 69 | 2.5 | 29.9 | 44.3 | 4.7 |
| Seq ID 27 | Seq ID 27.1 | 2.7 | 33.5 | 49.8 | 19.0 |
| Seq ID 70 | Seq ID 70 | 2.6 | 35.9 | 52.2 | 12.1 |
| Seq ID 71 | Seq ID 71.1 | 2.8 | 34.1 | 49.2 | 8.9 |
| Seq ID 71 | Seq ID 71.2 | 2.5 | 30.0 | 49.5 | 4.5 |
| Seq ID 72 | Seq ID 72 | 1.3 | 22.7 | 32.7 | 3.1 |
| Seq ID 73 | Seq ID 73 | 1.8 | 26.2 | 45.7 | 6.0 |
| Seq ID 74 | Seq ID 74 | 3.1 | 23.9 | 41.4 | 5.2 |
| Seq ID 75 | Seq ID 75 | 2.4 | 26.6 | 43.0 | 4.1 |
| Seq ID 76 | Seq ID 76 | 2.0 | 30.5 | 47.3 | 4.7 |
| Seq ID 77 | Seq ID 77 | 2.0 | 31.2 | 48.2 | 5.6 |
| Seq ID 78 | Seq ID 78 | 3.0 | 39.3 | 67.3 | 8.0 |
| Seq ID 79 | Seq ID 79 | 2.2 | 40.9 | 45.5 | 4.9 |
| Seq ID 80 | Seq ID 80 | 2.4 | 27.6 | 43.8 | 6.9 |
| Seq ID 81 | Seq ID 81 | 2.8 | 40.4 | 49.4 | 13.5 |
| Seq ID 82 | Seq ID 82 | 3.4 | 29.8 | 55.1 | 9.5 |
| Seq ID 83 | Seq ID 83 | 2.0 | 35.1 | 62.6 | 8.8 |
| Seq ID 84 | Seq ID 84 | 2.4 | 31.1 | 52.6 | 8.6 |
| Seq ID 85 | Seq ID 85 | 1.8 | 30.2 | 44.4 | 3.9 |
| Seq ID 86 | Seq ID 86 | 2.0 | 35.5 | 32.8 | 2.9 |
| Seq ID 23 | Seq ID 23.1 | 1.7 | 33.4 | 61.5 | 27.5 |
| Seq ID 87 | Seq ID 87 | 1.8 | 34.0 | 72.1 | 7.4 |
| Seq ID 88 | Seq ID 88 | 2.1 | 29.9 | 58.5 | 6.5 |
| Seq ID 23 | Seq ID 23.10 | 2.3 | 31.6 | 36.1 | 13.3 |
| Seq ID 89 | Seq ID 89 | 2.6 | 27.4 | 63.3 | 10.1 |
| Seq ID 90 | Seq ID 90 | 1.3 | 26.0 | 41.3 | 10.8 |
| Seq ID 91 | Seq ID 91 | 1.6 | 19.6 | 44.2 | 6.8 |
| Seq ID 92 | Seq ID 92 | 2.0 | 30.9 | 90.7 | 7.3 |
| Seq ID 93 | Seq ID 93 | 1.2 | 26.6 | 57.1 | 7.1 |
| Seq ID 94 | Seq ID 94 | 1.5 | 34.7 | 51.0 | 14.3 |
| Seq ID 95 | Seq ID 95 | 1.8 | 22.6 | 44.5 | 8.3 |
| Seq ID 96 | Seq ID 96 | 2.1 | 24.4 | 72.8 | 14.3 |
| Seq ID 97 | Seq ID 97 | 1.5 | 31.7 | 82.0 | 16.9 |
| Seq ID 98 | Seq ID 98 | 1.9 | 34.5 | 43.8 | 19.4 |
| Seq ID 99 | Seq ID 99 | 2.1 | 25.1 | 45.0 | 10.6 |
| Seq ID 100 | Seq ID 100 | 1.9 | 32.4 | 59.6 | 7.1 |
| Seq ID 101 | Seq ID 101 | 1.6 | 36.9 | 73.7 | 25.9 |
| Seq ID 102 | Seq ID 102 | 1.8 | 29.5 | 74.0 | 30.5 |
| Seq ID 103 | Seq ID 103 | 1.4 | 33.6 | 68.1 | 18.5 |

CERTAIN REFERENCES

Salter C G, Beijer D, Hardy H, et al. Truncating SLC5A7 mutations underlie a spectrum of dominant hereditary motor neuropathies. Neural Genet. 2018; 4(2):e222.

Yukiko Nasu-Nishimura 1, Tomoatsu Hayashi, Tomohiro Ohishi, Toshio Okabe, Susumu Ohwada, Yoshimi Hasegawa, Takao Senda, Chikashi Toyoshima, Tsutomu Nakamura, Tetsu Akiyama. Role of the Rho GTPase-activating Protein RICS in Neurite Outgrowth. Genes Cells. 2006 June; 11(6):607-14.

Arundhati Jana, Edward L. Hogan, and Kalipada Pahan. Ceramide and neurodegeneration: Susceptibility of neurons and oligodendrocytes to cell damage and death. J Neural Sci. 2009 Mar. 15; 278(1-2): 5-15.

Conti et al. TDP-43 affects splicing profiles and isoform production of genes involved in the apoptotic and mitotic cellular pathways. Nucleic Acids Res. 2015 Oct. 15; 43(18): 8990-9005.

Humphrey et al. Quantitative analysis of cryptic splicing associated with TDP-43 depletion. BMC Medical Genomics 2017; volume 10, Article number: 38 (2017).

Melamed et al. Premature polyadenylation-mediated loss of stathmin-2 is a hallmark of TDP-43-dependent neurodegeneration. Nat Neurosci. 2019 February; 22(2): 180-190.

Klim et al., ALS-implicated protein TDP-43 sustains levels of STMN2, a mediator of motor neuron growth and repair. Nature Neuroscience 22, pages 167-179 (2019)

Compounds Used in Examples 1, 3 & 4

| SEQ ID NO | Base sequence 5'-3' | Comp ID No | HELM |
|---|---|---|---|
| 1 | ACACACAC | 1.1 | [LR](A)[sP].[LR)([5meC])[sP].[LR](A)[sP].[dR](C)[sP].[dR](A)[sP].[LR]([5meC])[sP].[LR](A)[sP].[LR]([5meC]) |
| 2 | ACACACACA | 2.1 | [LR](A)[sP].[LR]([5meC])[sP].[dR](A)[sP].[LR]([5meC])[sP].[LR](A)[sP].[LR]([5meC])[sP].[dR](A)[sP].[LR]([5meC])[sP].[LR](A) |
| 3 | ACACACACAC | 3.1 | [LR](A)[sP].[LR]([5meC])[sP].[dR](A)[sP].[LR]([5meC])[sP].[LR](A)[sP].[LR]([5meC])[sP][dR](A)[sP].[LR]([5meC])[sP].[LR](A)[sP].[LR]([5meC]) |
| 4 | ACACACACACA | 4.1 | [LR](A)[sP].[LR]([5meC])[sP].[LR](A)[sP].[dR](C)[sP].[dR](A)[sP].[LR]((5meC])[sP].[LR](A)[sP].[dR](C)[sP].[LR](A)[sP].[LR]([5meC])[sP].[LR](A) |
| 5 | ACACACACACAC | 5.1 | [LR](A)[sP].[dR](C)[sP].[LR](A)[sP].[dR](C)[sP].[dR](A)[sP].[LR]([5meC])[sP].[LR](A)[sP][LR]([5meC])[sP].[dR](A)[sP].[LR]([5meC])[sP].[LR)(A)[sP].[LR]([5meC]) |
| 6 | ACACACACACACA | 6.1 | [LR](A)[sP].[dR](C)[sP].[LR](A)[sP].[dR](C)[sP].[LR](A)[sP].[LR]([5meC])[sP].[dR](A)[sP][LR]([5meC])[sP].[dR](A)[sP].[LR]([5meC])[sP].[dR](A)[sP].[LR]([5meC])[sP].[LR](A) |
| 6 | ACACACACACACA | 6.2 | [LR](A)[sP].[dR](C)[sP].[dR](A)[sP].[dR](C)[sP].[LR](A)[sP].[LR]([5meC])[sP].[dR](A)[sP][dR](C)[sP].[dR](A)[sP].[LR]([5meC])[sP].[dR](A)[sP].[LR]([5meC])[sP].[LR](A) |
| 6 | ACACACACACACA | 6.3 | [LR](A)[sP].[dR](C)[sP].[LR](A)[sP].[dR](C)[sP].[LR](A)[sP].[dR](C)[sP].[dR](A)[sP].[LR]([5meC])[sP].[dR](A)[sP].[dR](C)[sP].[dR](A)[sP].[LR]([5meC])[sP].[LR](A) |
| 6 | ACACACACACACA | 6.4 | [LR](A)[sP].[dR](C)[sP].[dR](A)[sP].[dR](C)[sP].[LR](A)[sP].[LR]([5meC])[sP].[dR](A)[sP].[LR]([5meC])[sP].[dR](A)[sP].[dR](C)[sP].[dR](A)[sP].[LR]([5meC])[sP].[LR](A) |
| 7 | ACACACACACACACAC | 7.1 | [LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 7 | ACACACACACACACAC | 7.2 | [LR](A)[sP].[dR](C)[sP].[LR](A)[sP].[dR](C)[sP].[dR](A)[sP].[dR](C)[sP].[LR](A)[sP].[dR](C)[sP].[dR](A)[sP].[dR](C)[sP].[LR](A)[sP].[dR](C)[sP].[LR](A)[sP].[dR](C)[sP].[LR](A)[sP].[LR]([5meC]) |
| 7 | ACACACACACACACAC | 7.3 | [LR](A)[sP].[LR]([5meC])[sP].[dR](A)[sP].[dR](C)[sP].[LR](A)[sP].[dR](C)[sP].[dR](A)[sP][dR](C)[sP].[LR](A)[sP].[dR](C)[sP].[dR](A)[sP].(dR](C)[sP].[LR](A)[sP].[dR](C)[sP].[LR](A)[sP].[LR]([5meC]) |
| 8 | ACACACACACACACAC | 8.1 | [LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 8 | ACACACACACACACACAC | 8.2 | [LR](A)[sP].[dR](C)[sP].[LR](A)[sP].[dR](C)[sP].[dR](A)[sP].[dR](C)[sP].[LR](A)[sP].[dR](C)[sP].[dR](A)[sP].[dR](C)[sP].[LR](A)[sP].[dR](C)[sP].[dR](A)[sP].[dR](C)[sP].[LR](A)[sP].[dR](C)[sP].[LR](A)[sP].[LR]([5meC]) |
| 8 | ACACACACACACACACAC | 8.3 | [LR](A)[sP].[LR]([5meC])[sP].[LR](A)[sP].[dR](C)[sP].[dR](A)[sP].[dR](C)[sP].[LR](A)[sP][dR](C)[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[LR]([5meC]) |
| 9 | CACACAC | 9.1 | [LR]([5meC])[sP].[LR](A)[sP].[LR]([5meC])[sP].[LR](A)[sP].[LR]([5meC])[sP].[LR](A)[sP][LR]([5meC]) |

-continued

| SEQ ID NO | Base sequence 5'-3' | Comp ID No | HELM |
|---|---|---|---|
| 10 | CACACACA | 10.1 | [LR]([5meC])[sP].[LR](A)[sP].[LR]([5meC])[sP].[LR](A)[sP].[LR]([5meC])[sP].[LR](A)[sP].[LR]([5meC])[sP].[LR](A) |
| 10 | CACACACA | 10.2 | [LR]([5meC])[sP].[LR](A)[sP].[LR]([5meC])[sP].[dR](A)[sP].[LR]([5meC])[sP].[dR](A)[sP].[LR)([5meC])[sP].[LR)(A) |
| 11 | CACACACAC | 11.1 | [LR]([5meC])[sP].[LR](A)[sP].[LR]([5meC])[sP].[dR](A)[sP].[LR]([5meC])[sP].[dR](A)[sP].[LR]([5meC])[sP].[LR](A)[sP].[LR]([5meC]) |
| 12 | CACACACACA | 12.1 | [LR]([5meC])[sP].[LR](A)[sP].[LR]([5meC])[sP].[dR](A)[sP].[LR]([5meC])[sP].[LR](A)[sP][LR]([5meC])[sP].[dR](A)[sP].[LR]([5meC])[sP].[LR)(A) |
| 13 | CACACACACAC | 13.1 | [LR]([5meC])[sP].[LR](A)[sP].[dR](C)[sP].[LR](A)[sP].[LR]([5meC])[sP].[LR](A)[sP].[dR](C)[sP].[dR](A)[sP].[LR]([5meC])[sP].[LR](A)[sP].[LR]([5meC]) |
| 14 | CACACACACACA | 14.1 | [LR]([5meC])[sP].[LR](A)[sP].[dR](C)[sP].[LR](A)[sP].[dR](C)[sP].[LR](A)[sP].[LR]([5meC])[sP].[dR](A)[sP].[LR]([5meC])[sP].[dR](A)[sP].[LR]([5meC])[sP].[LR](A) |
| 14 | CACACACACACA | 14.2 | [LR]([5meC])[sP].[LR](A)[sP].[dR](C)[sP].[LR](A)[sP].[dR](C)[sP].[dR](A)[sP].[LR]([5meC])[sP].[dR](A)[sP].[dR](C)[sP].[dR](A)[sP].[LR]([5meC])[sP].[LR](A) |
| 14 | CACACACACACA | 14.3 | [LR]([5meC])[sP].[LR](A)[sP].[dR](C)[sP].[dR](A)[sP].[dR](C)[sP].[LR](A)[sP].[LR]([5meC])[sP].[dR](A)[sP].[LR]([5meC])[sP].[dR](A)[sP].[dR](C)[sP].[LR](A) |
| 14 | CACACACACACA | 14.4 | [LR]([5meC])[sP].[dR](A)[sP].[dR](C)[sP].[LR](A)[sP].[dR](C)[sP].[LR](A)[sP].[LR]([5meC])[sP].[dR](A)[sP].[dR](C)[sP].[dR](A)[sP].[LR]([5meC])[sP].[LR](A) |
| 15 | CACACACACACAC | 15.1 | [LR]([5meC])[sP].[dR](A)[sP].[LR]([5meC])[sP].[dR](A)[sP].[LR]([5meC])[sP].[dR](A)[sP].[LR]([5meC])[sP].[LR](A)[sP].[dR](C)[sP].[LR](A)[sP].(dR](C)[sP].[LR)(A)[sP].[LR]([5meC]) |
| 15 | CACACACACACAC | 15.2 | [LR]([5meC])[sP].[dR](A)[sP].[dR](C)[sP].[dR](A)[sP].[LR]([5meC])[sP].[dR](A)[sP].[dR](C)[sP].[LR](A)[sP].[dR](C)[sP].[LR](A)[sP].[dR](C)[sP].[LR](A)[sP].[LR]([5meC]) |
| 15 | CACACACACACAC | 15.3 | [LR]([5meC])[sP].[dR](A)[sP].[LR]([5meC])[sP].[dR](A)[sP].[dR](C)[sP].[dR](A)[sP].[LR]([5meC])[sP].[LR](A)[sP].[dR](C)[sP].[dR](A)[sP].[dR](C)[sP].[LR](A)[sP].[LR]([5meC]) |
| 15 | CACACACACACAC | 15.4 | [LR]([5meC])[sP].[dR](A)[sP].[dR](C)[sP].[dR](A)[sP].[LR]([5meC])[sP].[dR](A)[sP].[dR](C)[sP].[LR](A)[sP].[dR](C)[sP].[LR](A)[sP].[dR](C)[sP].[dR](A)[sP].[LR]([5meC]) |
| 15 | CACACACACACAC | 15.5 | [LR]([5meC])[sP].[dR](A)[sP].[dR](C)[sP].[dR](A)[sP].[LR]([5meC])[sP].[dR](A)[sP].[dR](C)[sP].[LR](A)[sP].[dR](C)[sP].[dR](A)[sP].[dR](C)[sP].[LR](A)[sP].[LR]([5meC]) |
| 16 | CACACACACACACA CA | 16.1 | [LR]([5meC])[sP].[dR](A)[sP].[dR](C)[sP].[LR](A)[sP].[dR](C)[sP].[LR](A)[sP].[dR](C)[sP][LR](A)[sP].[dR](C)[sP].[LR](A)[sP].[dR](C)[sP].[LR](A)[sP].[dR](C)[sP].[dR](A)[sP].(LR]([5meC])[sP].[LR](A) |
| 16 | CACACACACACACA CA | 16.2 | [LR]([5meC])[sP].[dR](A)[sP].[dR](C)[sP].[LR](A)[sP].[dR](C)[sP].[dR](A)[sP].[dR](C)[sP][LR](A)[sP].[dR](C)[sP].[LR](A)[sP].[dR](C)[sP].[LR](A)[sP].[dR](C)[sP].[dR](A)[sP].[LR]([5meC])[sP].[LR](A) |
| 16 | CACACACACACACA CA | 16.3 | [LR]([5meC])[sP].[dR](A)[sP].[dR](C)[sP].[LR](A)[sP].[dR](C)[sP].[dR](A)[sP].[dR](C)[sP][LR](A)[sP].[dR](C)[sP].[dR](A)[sP].[dR](C)[sP].[LR](A)[sP].[dR](C)[sP].[dR](A)[sP].[LR]([5meC])[sP].[LR](A) |
| 18 | CACACACACACACA CACA | 18.1 | [LR]([5meC])[sP].[dR](A)[sP].[dR](C)[sP].[LR](A)[sP].[dR](C)[sP].[LR](A)[sP].[dR](C)[sP][LR](A)[sP].[dR](C)[sP].[LR)(A)[sP].[dR](C)[sP].[LR](A)[sP].[dR](C)[sP].[LR](A)[sP].[dR](C)[sP].[dR](A)[sP].[LR]([5meC])[sP].[LR](A) |

-continued

| SEQ ID NO | Base sequence 5'-3' | Comp ID No | HELM |
|---|---|---|---|
| 18 | CACACACACACACA CACA | 18.2 | [LR]([5meC])[sP].[dR](A)[sP].[dR](C)[sP].[LR](A)[sP].[dR](C)[sP].[dR](A)[sP].[dR](C)[sP][LR](A)[sP].[dR](C)[sP].[dR](A)[sP].[dR](C)[sP].(LR](A)[sP].[LR]([5meC])[sP].[dR](A)[sP].[dR](C)[sP].[dR](A)[sP].(LR]([5meC])[sP].[LR](A) |
| 18 | CACACACACACACA CACA | 18.3 | [LR]([5meC])[sP].[dR](A)[sP].[LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[dR](A)[sP].[dR](C)[sP].[LR](A)[sP].[dR](C)[sP].[dR](A)[sP].[LR]([5meC])[sP].[LR](A) |
| 18 | CACACACACACACA CACA | 18.4 | [LR]([5meC])[sP].[dR](A)[sP].[dR](C)[sP].[LR](A)[sP].[dR](C)[sP].[LR](A)[sP].[dR](C)[sP][dR](A)[sP].[dR](C)[sP].[LR](A)[sP].[LR]([5meC])[sP].[dR](A)[sP].[dR](C)[sP].[LR](A)[sP].[dR](C)[sP].[dR](A)[sP].[LR]([5meC])[sP].[LR](A) |
| 19 | TCCACACTGAACAA ACC | 19.1 | [LR](T)[sP].[LR]([5meC])[sP].[dR](C)[sP].[dR](A)[sP].[dR](C)[sP].[dR](A)[sP].[dR](C)[sP][dR](T)[sP].[dR](G)[sP].[dR](A)[sP].[dR](A)[sP].[dR](C)[sP].[dR](A)[sP].[LR](A)[sP].[LR](A)[sP].[LR]([5meC])[sP].[LR]([5meC]) |
| 20 | CACACACACACACA CACACACAC | 20.1 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 21 | ACACACACACACAC ACACACACAC | 21 | [LR](A)[sP].[LR]([5meC])[sP].[dR](A)[sP].[LR]((5meC])[sP].[dR](A)[sP].(LR]([5meC])[sP][dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC]) |
| 22 | CACACACACACAAC ACACACACAC | 22.1 | [LR]([5meC])[sP].[LR](A)[sP].[dR](C)[sP].[LR](A)[sP].[dR](C)[sP].[LR](A)[sP].[dR](C)[sP][LR](A)[sP].[dR](C)[sP].[dR](A)[sP].[LR]([5meC])[sP].[LR](A)[sP].[LR](A)[sP].[LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 22 | CACACACACACAAC ACACACACAC | 22.2 | [LR]([5meC])[sP].[LR](A)[sP].[LR]([5meC])[sP].[LR](A)[sP].[LR]([5meC])[sP].[LR](A)[sP][LR]([5meC])[sP].[LR](A)[sP].[LR]([5meC])[sP].[LR](A)[sP].[LR]([5meC])[sP].[LR](A)[sP][LR](A)[sP].[LR]([5meC])[sP].[LR](A)[sP].[LR]([5meC])[sP].[LR](A)[sP].[LR]([5meC])[sP].[LR](A)[sP].[LR]([5meC])[sP].[LR](A)[sP].[LR]([5meC])[sP].[LR](A)[sP].[LR]([5meC]) |
| 23 | CACACACACACACA CACACACACAC | 23.6 | [LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR) (A)[sP].[dR](C)[sP].[dR](A)[sP].[LR]([5meC])[sP][LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC]) |
| 23 | CACACACACACACA CACACACACAC | 23.7 | [LR]([5meC])[sP].[LR](A)[sP].[dR](C)[sP].[dR](A)[sP].[dR](C)[sP].[LR](A)[sP].[LR]([5meC])[sP].[dR](A)[sP].[dR](C)[sP].[LR](A)[sP].[LR]([5meC])[sP].[dR](A)[sP].[dR](C)[sP].[dR](A)[sP].[LR]([5meC])[sP].[LR) (A)[sP].[dR](C)[sP].[dR](A)[sP].[dR](C)[sP].[LR](A)[sP][dR](C)[sP].[dR](A)[sP].[dR](C)[sP].[LR](A)[sP].[LR]([5meC]) |
| 23 | CACACACACACACA CACACACACAC | 23.8 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[SP].[dR](A)[sP].[dR](C)[sP].[LR](A)[sP][LR]([5meC]) |
| 23 | CACACACACACACA CACACACACAC | 23.9 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |

-continued

| SEQ ID NO | Base sequence 5'-3' | Comp ID No | HELM |
|---|---|---|---|
| 24 | ACACACACACACAC ACACACACACAC | 24 | [LR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC]) |
| 25 | CACACACACACACA CACACACACACAC | 25.1 | [LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[LR]([5meC]) |
| 25 | CACACACACACACA CACACACACACAC | 25.2 | [LR]([5meC])[sP].[LR](A)[sP].[dR](C)[sP].[dR](A)[sP].[dR](C)[sP].[LR](A)[sP].[LR]([5meC])[sP].[dR](A)[sP].[dR](C)[sP].[LR](A)[sP].[LR]([5meC])[sP].[dR](A)[sP].[dR](C)[sP].[dR](A)[sP].[LR]([5meC])[sP].[LR](A)[sP].[dR](C)[sP].[dR](A)[sP].[LR]([5meC])[sP].[dR](A)[sP].[dR](C)[sP].[LR](A)[sP].[dR](C)[sP].[dR](A)[sP].[dR](C)[sP].[LR](A)[sP].[LR]([5meC]) |
| 25 | CACACACACACACA CACACACACACAC | 25.3 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A][sP].[dR](C)[sP].[LR](A)[sP].[LR]([5meC]) |
| 25 | CACACACACACACA CACACACACACAC | 25.4 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 26 | ACACACACACACAC ACACACACACACAC | 26 | [LR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC]) |
| 27 | CACACACACACACA CACACACACACACA C | 27.1 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 27 | CACACACACACACA CACACACACACACA C | 27.2 | [LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC]) |
| 27 | CACACACACACACA CACACACACACACA C | 27.3 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A][sP].[LR]([5meC])[sP].[dR](A)[sP].[dR](C)[sP].[LR](A)[sP].[LR]([5meC]) |
| 27 | CACACACACACACA CACACACACACACA C | 27.4 | [LR]([5meC])[sP].[LR](A)[sP].[dR](C)[sP].[dR](A)[sP].[dR](C)[sP].[LR](A)[sP].[LR]([5meC])[sP].[dR](A)[sP].[dR](C)[sP].[LR](A)[sP].[LR]([5meC])[sP].[dR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[dR](C)[sP].[LR](A)[sP].[dR](C)[sP].[dR](A)[sP].[dR](C)[sP].[LR](A)[sP].[LR]([5meC]) |

-continued

| SEQ ID NO | Base sequence 5'-3' | Comp ID No | HELM |
|---|---|---|---|
| 28 | ACACACACACACACACACACACACACACAC | 28 | [LR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC]) |
| 29 | CACACACACACACACACACACACACACAC | 29.1 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 29 | CACACACACACACACACACACACACACAC | 29.2 | [LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[LR]([5meC]) |
| 29 | CACACACACACACACACACACACACACAC | 29.3 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A][sP].[LR]([5meC])[sP].[dR](A)[sP].[LR]([5meC])[sP].[dR](A)[sP].[dR](C)[sP].[LR](A)[sP].[LR]([5meC]) |
| 29 | CACACACACACACACACACACACACACAC | 29.4 | [LR]([5meC])[sP].[LR](A)[sP].[dR](C)[sP].[dR](A)[sP].[dR](C)[sP].[LR](A)[sP].[LR]([5meC])[sP].[dR](A)[sP].[dR](C)[sP].[LR](A)[sP].[LR]([5meC])[sP].[dR](A)[sP].[dR](C)[sP].[dR](A)[sP].[LR]([5meC])[sP].[LR](A)[sP].[dR](C)[sP].[dR](A)[sP].[LR]([5meC])[sP].[LR](A)[sP].[dR](C)[sP].[dR](A)[sP].[dR](C)[sP].[LR](A)[sP].[LR]([5meC])[sP].[LR](A)[sP].[dR](C)[sP].[dR](A)[sP].[dR](C)[sP].[LR](A)[sP].[LR]([5meC]) |
| 29 | ACACACACACACACACACCACACACACACACACA | 30 | [LR](A)[sP].[LR]([5meC])[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[LR]([5meC])[sP].[LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A) |
| 31 | CACACACACACACACACACACACACACACACA | 31.1 | [LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A)[sP].[LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A) |
| 31 | CACACACACACACACACACACACACACACACA | 31.2 | [LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A)[sP].[LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A) |
| 31 | CACACACACACACACACAACACACACACACACAC | 32 | [LR]([5meC])[sP].[dR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A)[sP].[LR](A)[sP].[LR]([5meC])[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[LR]([5meC]) |
| 33 | ACACACACACACACACACCACACACACACACACACA | 33 | [LR](A)[sP].[LR]([5meC])[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[dR](C)[sP].[LR](A)[sP].[dR](C)[sP].[LR](A)[sP].[dR](C)[sP].[dR](A)[sP].[LR]([5meC])[sP].[LR]([5meC])[sP].[dR](A)[sP]. |

-continued

| SEQ ID NO | Base sequence 5'-3' | Comp ID No | HELM |
|---|---|---|---|
| | | | [dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[dR](A)[sP].[LR]([5meC])[sP].[LR](A) |
| 22 | CACACACACACAACACACACACAC | 22.3 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 23 | CACACACACACACACACACACAC | 23.1 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 25 | CACACACACACACACACACACACAC | 25.5 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 27 | CACACACACACACACACACACACACAC | 27.5 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 29 | CACACACACACACACACACACACACACAC | 29.5 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 23 | CACACACACACACACACACACAC | 23.2 | [MOE]([5meC])[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[MOE]([5meC]) |
| 25 | CACACACACACACACACACACACAC | 25.6 | [MOE]([5meC])[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[MOE]([5meC]) |
| 23 | CACACACACACACACACACACAC | 23.3 | [MOE]([5meC])[sP].[MOE](A)[sP].[dR](C)[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[dR](C)[sP].[MOE](A)[sP].[MOE]([5meC]) |
| 25 | CACACACACACACACACACACACAC | 25.7 | [MOE]([5meC])[sP].[MOE](A)[sP].[dR](C)[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[dR](C)[sP].[MOE](A)[sP].[MOE]([5meC]) |

-continued

| SEQ ID NO | Base sequence 5'-3' | Comp ID No | HELM |
|---|---|---|---|
| 27 | CACACACACACACACACACACACACAC | 27.6 | [MOE]([5meC])[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[MOE]([5meC]) |
| 27 | CACACACACACACACACACACACACAC | 27.7 | [MOE]([5meC])[sP].[MOE](A)[sP].[dR](C)[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[dR](C)[sP].[MOE](A)[sP].[MOE]([5meC]) |
| 29 | CACACACACACACACACACACACACACAC | 29.6 | [MOE]([5meC])[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[dR](C)[sP].[MOE](A)[sP].[MOE]([5meC]) |
| 29 | CACACACACACACACACACACACACACAC | 29.7 | [MOE]([5meC])[sP].[MOE](A)[sP].[dR](C)[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[MOE]([5meC])[sP].[dR](A)[sP].[dR](C)[sP].[MOE](A)[sP].[MOE]([5meC]) |
| 23 | CACACACACACACACACACACAC | 23.4 | [mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C) |
| 25 | CACACACACACACACACACACACAC | 25.8 | [mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C) |
| 27 | CACACACACACACACACACACACACAC | 27.8 | [mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C) |
| 29 | CACACACACACACACACACACACACACAC | 29.8 | [mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C)[sP].[mR](A)[sP].[mR](C) |
| 23 | CACACACACACACACACACACAC | 23.5 | [mR](C)[sP].[mR](A)[sP].[dR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[dR](C)[sP].[mR](A)[sP].[mR](C) |
| 25 | CACACACACACACACACACACACAC | 25.9 | [mR](C)[sP].[mR](A)[sP].[dR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[dR](C)[sP].[mR](A)[sP].[mR](C) |

-continued

| SEQ ID NO | Base sequence 5'-3' | Comp ID No | HELM |
|---|---|---|---|
| 27 | CACACACACACACA CACACACACACACA C | 27.9 | [mR](C)[sP].[mR](A)[sP].[dR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[dR](C)[sP].[mR](A)[sP].[mR](C) |
| 29 | CACACACACACACA CACACACACACACA CAC | 29.9 | [mR](C)[sP].[mR](A)[sP].[dR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[mR](C)[sP].[dR](A)[sP].[dR](C)[sP].[mR](A)[sP].[mR](C) |
| 34 | ACACACACACACAC ACACACACACACAC ACAC | 34 | [LR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC]) |
| 20 | CACACACACACACA CACACACAC | 20.2 | [LR]([5meC])[sP].[LR](A)[sP].[dR](C)[sP].[MOE](A)[sP].[LR]([5meC])[sP].[MOE](A)[sP].[LR]([5meC])[sP].[dR](A)[sP].[LR]([5meC])[sP].[MOE](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 50 | CACACACCCACICA CACACGCAC | 50 | [LR]([5meC])[sP].[LR](A)[sP].[dR](C)[sP].[dR](A)[sP].[LR]([5meC])[sP].[dR](A)[sP].[LR]([5meC])[sP].[dR](C)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](G)[sP].[dR](C)[sP].[LR](A)[sP].[LR]([5meC]) |
| 51 | CACACICACACACA CACACACAC | 51 | [LR]([5meC])[sP].[LR](A)[sP].[dR](C)[sP].[dR](A)[sP].[LR]([5meC])[sP].[dR]([In])[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 52 | CACACACACACICA CACACACAC | 52 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR]([In])[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 53 | CACACICACACACA CACACACTC | 53 | [LR]([5meC])[sP].[LR](A)[sP].[dR](C)[sP].[dR](A)[sP].[LR]([5meC])[sP].[dR](In)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](T)[sP].[LR]([5meC]) |
| 54 | CACATACACACCCA CACACACAC | 54 | [LR]([5meC])[sP].[LR](A)[sP].[dR](C)[sP].[dR](A)[sP].[LR](T)[sP].[LR](A)[sP].[LR]([5meC])[sP].[dR](A)[sP].[LR]([5meC])[sP].[dR](A)[sP].[LR]([5meC])[sP].[dR](C)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 55 | CACACACACACACA CACGCACAC | 55 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](G)[sP].[LR]([5meC])[sP].[dR](A)[sP].[dR](C)[sP].[LR](A)[sP].[LR]([5meC]) |
| 56 | CACICACICACACA CICACICAC | 56 | [LR]([5meC])[sP].[LR](A)[sP].[dR](C)[sP].[dR]([In])[sP].[LR]([5meC])[sP].[dR](A)[sP].[LR]([5meC])[sP].[dR]([In])[sP].[LR]([5meC])[sP].[dR](A)[sP].[LR]([5meC])[sP].[dR](A)[sP].[LR]([5meC])[sP].[dR](A)[sP].[LR]([5meC])[sP].[dR]([In])[sP].[LR]([5meC])[sP].[dR](A)[sP].[LR]([5meC])[sP].[dR]([In])[sP].[dR](C)[sP].[LR](A)[sP].[LR]([5meC]) |
| 57 | CACACACACACACA CTCTCACAC | 57 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A) |

-continued

| SEQ ID NO | Base sequence 5'-3' | Comp ID No | HELM |
|---|---|---|---|
| | | | [sP].[LR]([5meC])[sP].[dR](T)[sP].[LR]([5meC])[sP].[dR](T)[sP].[LR]([5meC])[sP].[dR](A)[sP].[dR](C)[sP].[LR](A)[sP].[LR]([5meC]) |
| 58 | CTCACACACACACACACACAC | 58 | [LR]([5meC])[sP].[LR](T)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 59 | CACACACACACAAACACACAC | 59 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR](A)[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 60 | CACACGCACGCACACACACAC | 60 | [LR]([5meC])[sP].[LR](A)[sP].[dR](C)[sP].[dR](A)[sP].[LR]([5meC])[sP].[dR](G)[sP].[LR]([5meC])[sP].[dR](A)[sP].[LR]([5meC])[sP].[dR](G)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 61 | CACGCACACACCCACACACTCAC | 61 | [LR]([5meC])[sP].[LR](A)[sP].[dR](C)[sP].[dR](G)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](C)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](T)[sP].[dR](C)[sP].[LR](A)[sP].[LR]([5meC]) |
| 62 | CACACACACACACTCTCTCACAC | 62 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](T)[sP].[LR]([5meC])[sP].[dR](T)[sP].[LR]([5meC])[sP].[dR](T)[sP].[LR]([5meC])[sP].[dR](A)[sP].[dR](C)[sP].[LR](A)[sP].[LR]([5meC]) |
| 63 | CACACACACACACICICICICAC | 63 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR]([In])[sP].[LR]([5meC])[sP].[dR]([In])[sP].[LR]([5meC])[sP].[dR]([In])[sP].[LR]([5meC])[sP].[dR]([In])[sP].[dR](C)[sP].[LR](A)[sP].[LR]([5meC]) |
| 64 | CACTCACACACTCACACACAC | 64 | [LR]([5meC])[sP].[LR](A)[sP].[dR](C)[sP].[dR](T)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](T)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 65 | CACGCACACACGCACACACAC | 65 | [LR]([5meC])[sP].[LR](A)[sP].[dR](C)[sP].[dR](G)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](G)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 66 | CACCCACACACCCACACACAC | 66 | [LR]([5meC])[sP].[LR](A)[sP].[dR](C)[sP].[dR](C)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](C)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 67 | CACACGCACATACACACCCAC | 67 | [LR]([5meC])[sP].[LR](A)[sP].[dR](C)[sP].[dR](A)[sP].[LR]([5meC])[sP].[dR]([In])[sP].[LR]([5meC])[sP].[dR](A)[sP].[LR]([5meC])[sP].[dR](A)[sP].[LR](T)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](C)[sP].[dR](C)[sP].[LR](A)[sP].[LR]([5meC]) |
| 68 | TTCACACACACACACACACAC | 68 | [LR](T)[sP].[LR](T)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR]([5meC]) |
| 69 | CACACACACACACACACACAA | 69 | [LR]([5meC])[sP].[LR](A)[sP].[dR](C)[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[LR]([5meC])[sP].[dR](A)[sP].[dR](C)[sP].[LR](A)[sP].[LR](A) |

-continued

| SEQ ID NO | Base sequence 5'-3' | Comp ID No | HELM |
|---|---|---|---|
| 70 | CACACACACACACA CACACAIACACACA C | 70 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR]([In])[sP].[LR](A)[sP].[dR](C)[sP].[LR](A)[sP].[dR](C)[sP].[LR](A)[sP].[dR](C)[sP].[LR](A)[sP].[LR]([5meC]) |
| 71 | CACAIACACACACA CACACACACACACA C | 71.1 | [LR]([5meC])[sP].[LR](A)[sP].[dR](C)[sP].[LR](A)[sP].[dR]([In])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 72 | CATACACACACACA CACACATACACACA C | 72 | [LR]([5meC])[sP].[LR](A)[sP].[dR](T)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](T)[sP].[LR](A)[sP].[dR](C)[sP].[LR](A)[sP].[dR](C)[sP].[LR](A)[sP].[dR](C)[sP].[LR](A)[sP].[LR]([5meC]) |
| 73 | CAAACACACACACA CACACACACACACA C | 73 | [LR]([5meC])[sP].[LR](A)[sP].[dR](A)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 74 | CACACACATCACAC ACACACACACACAC | 74 | [LR]([5meC])[sP].[LR](A)[sP].[dR](C)[sP].[LR](A)[sP].[dR](C)[sP].[LR](A)[sP].[dR](C)[sP].[LR](A)[sP].[LR]([5meC])[sP].[LR](T)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 75 | CACAGACACACACA CACACACACACACA C | 75 | [LR]([5meC])[sP].[LR](A)[sP].[dR](C)[sP].[LR](A)[sP].[dR](G)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 71 | CACAIACACACACA CACACACACACACA C | 71.2 | [LR]([5meC])[sP].[LR](A)[sP].[dR](C)[sP].[LR](A)[sP].[dR]([In])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 76 | CACAAACACACACA CACACACACACACA C | 76 | [LR]([5meC])[sP].[LR](A)[sP].[dR](C)[sP].[LR](A)[sP].[dR](A)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 77 | CACATACACACACA CACACACACACACA C | 77 | [LR]([5meC])[sP].[LR](A)[sP].[dR](C)[sP].[LR](A)[sP].[dR](T)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 78 | CATACGCACATACA CGCACACACAAACA C | 78 | [LR]([5meC])[sP].[LR](A)[sP].[dR](T)[sP].[LR](A)[sP].[dR](C)[sP].[LR](G)[sP].[dR](C)[sP].[LR](A)[sP].[dR](C)[sP].[LR](A)[sP].[dR](T)[sP].[LR](A)[sP].[dR](C)[sP].[LR](A)[sP].[dR](C)[sP].[LR](G)[sP].[dR](C)[sP].[LR](A)[sP].[dR](C)[sP].[LR](A)[sP].[dR](C)[sP].[LR](A)[sP].[dR](C)[sP].[LR](A)[sP].[dR](A)[sP].[LR](A)[sP].[dR](C)[sP].[LR](A)[sP].[LR]([5meC]) |
| 79 | CACATATACACATA CACACACACACACA C | 79 | [LR]([5meC])[sP].[LR](A)[sP].[dR](C)[sP].[LR](A)[sP].[dR](T)[sP].[LR](A)[sP].[dR](T)[sP].[LR](A)[sP].[dR](C)[sP].[LR](A)[sP].[dR](C)[sP].[LR](A)[sP].[dR](T)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |

-continued

| SEQ ID NO | Base sequence 5'-3' | Comp ID No | HELM |
|---|---|---|---|
| 80 | CACACACACACACA CACACTCTCTCTCT C | 80 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](T)[sP].[dR](C)[sP].[LR](T)[sP].[dR](C)[sP].[LR](T)[sP].[dR](C)[sP].[LR](T)[sP].[dR](C)[sP].[LR](T)[sP].[LR]([5meC]) |
| 81 | CACGCACACACACA CACACACACACACA C | 81 | [LR]([5meC])[sP].[LR](A)[sP].[dR](C)[sP].[LR](G)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 82 | CACACACACACACA CAITITITCACACA C | 82 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR]([In])[sP].[LR](T)[sP].[dR]([In])[sP].[LR](T)[sP].[dR] P].[LR](T)[sP].[dR](C)[sP].[LR](A)[sP].[dR](C)[sP].[LR](A)[sP].[dR](C)[sP].[LR](A)[sP].[LR]([5meC]) |
| 83 | CGCACACACACACA CACACACACACACA C | 83 | [LR]([5meC])[sP].[LR](G)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 84 | CACACACACACACA CAGACAGACAGACA C | 84 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](G)[sP].[LR](A)[sP].[dR](C)[sP].[LR](A)[sP].[dR](G)[sP].[LR](A)[sP].[dR](C)[sP].[LR](A)[sP].[dR](G)[sP].[LR](A)[sP].[dR](C)[sP].[LR](A)[sP].[LR]([5meC]) |
| 85 | CACACACACAAAAA AACACACACACACA C | 85 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](A)[sP].[LR](A)[sP].[dR](A)[sP].[LR](A)[sP].[dR](A)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 86 | CACACACACACCCC CCCACACACACACA C | 86 | [LR]([5meC])[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR]([5meC])[sP].[dR](C)[sP].[LR]([5meC])[sP].[dR](C)[sP].[sP].[LR]([5meC])[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[dR](C)[sP].[LR](A)[sP].[LR]([5meC]) |
| 87 | CACACACACTCTCT CACACACACAC | 87 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](T)[sP].[MOE]([5meC])[sP].[MOE](T)[sSP].[MOE]([5meC])[sP].[MOE](T)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 88 | CACAAACACACACA CACACACACAC | 88 | [MOE]([5meC])[sP].[MOE](A)[sP].[MOE]([5meC])[sP].[MOE](A)[sP].[MOE](A)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 23 | CACACACACACACA CACACACACAC | 23.10 | [MOE]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP].[LR]([5meC])[sP].[MOE](A)[sP][LR]([5meC])[sP].[MOE](A)[sP].[MOE]([5meC]) |

-continued

| SEQ ID NO | Base sequence 5'-3' | Comp ID No | HELM |
|---|---|---|---|
| 89 | CACTCACACACACA CACACACACAC | 89 | [MOE]([5meC])[sP].[MOE](A)[sP].[MOE]([5meC])[sP].[MOE](T)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 90 | CACACACACAAACA CACACACACAC | 90 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE](A)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 91 | CACCCACACACACA CACACACACAC | 91 | [MOE]([5meC])[sP].[MOE](A)[sP].[MOE]([5meC])[sP].[MOE]([5meC])[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 92 | CTCTCTCACACACA CACACACACAC | 92 | [MOE]([5meC])[sP].[MOE](T)[sP].[MOE]([5meC])[sP].[MOE](T)[sP].[MOE]([5meC])[sP].[MOE](T)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 93 | CAAACACACACACA CACACACACAC | 93 | [MOE]([5meC])[sP].[MOE](A)[sP].[MOE](A)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 94 | CACACACACCCACA CACACACACAC | 94 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE]([5meC])[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 95 | CACACACACACACA CCCACACACAC | 95 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE]([5meC])[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 96 | CACACACACACACA CGCACACACAC | 96 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 97 | CACACACACACACA CTCACACACAC | 97 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](T)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 98 | CACACACACATACA CACACACACAC | 98 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE](TilsP].[MOE](A)[sP].[MOE] |

-continued

| SEQ ID NO | Base sequence 5'-3' | Comp ID No | HELM |
|---|---|---|---|
| | | | ([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 99 | CACACACACAGACACACACACACAC | 99 | [MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE](G)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 100 | TTTACACACACACACACACACACAC | 100 | [MOE](T)[sP].[MOE](T)[sP].[MOE](T)[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 101 | CACGCACACGCACACACACACACAC | 101 | [MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |
| 102 | CACGCACACACGCACACACACGCAC | 102 | [MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](GilsP].[MOE]([5meC])[sP].[MOE](A)[sP].[MOE]([5meC]) |
| 103 | CACACGCACACACACACACACACAC | 103 | [MOE]([5meC])[sP].[MOE](A)[sP].[MOE]([5meC])[sP].[MOE](A)[sP].[MOE]([5meC])[sP].[MOE](G)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC])[sP].[MOE](A)[sP].[MOE]([5meC]) |

Helm Annotation Key:
[LR](G) is a beta-D-oxy-LNA guanine nucleoside,
[LR](T) is a beta-D-oxy-LNA thymine nucleoside,
[LR](A) is a beta-D-oxy-LNA adenine nucleoside,
[LR]([5meC] is a beta-D-oxy-LNA 5 methyl cytosine nucleoside,
[dR](G) is a DNA guanine nucleoside,
[dR](T) is a DNA thymine nucleoside,
[dR](A) is a DNA adenine nucleoside,
[dR]([C] is a DNA cytosine nucleoside,
[sP] is a phosphorothioate internucleoside linkage.
[mR]([C] is a 2'O-Methyl cytidine nucleoside
[mR]([A] is a 2'O-Methyl adenine nucleoside
[MOE]([5meC]) is a 2'O-MOE [2'O-(2-methoxyethyl)] 5-methyl cytidine nucleoside
[MOE](A) is a 2'O-MOE [2'O-(2-methoxyethyl)] adenine nucleoside
[dR]([In] is a DNA inosine nucleoside

The invention claimed is:

1. An antisense oligonucleotide consisting of the contiguous nucleotide sequence CACACACACACACACACACACACACACAC (SEQ ID NO: 27), wherein the antisense oligonucleotide is capable of restoring a functional phenotype of one or more TDP-43 target RNAs in a TDP-43-depleted cell or a cell expressing aberrant TDP-43 protein and wherein the contiguous nucleotide sequence comprises one or more modified nucleosides.

2. The antisense oligonucleotide of claim 1, wherein the contiguous nucleotide sequence is at least 75% complementary to the target sequence.

3. The antisense oligonucleotide of claim 1, wherein the contiguous nucleotide sequence comprises 1, 2, 3, 4, 5, 6, 7, or 8 or more mismatches to the target sequence.

4. The antisense oligonucleotide of claim 1, wherein the Gibbs free energy of the antisense oligonucleotide to a complementary target RNA is lower than $-10\Delta G$.

5. The antisense oligonucleotide of claim 1, wherein the antisense oligonucleotide is capable of modulating splicing of one or more TDP-43 target pre-mRNAs.

6. The antisense oligonucleotide of claim 1, wherein the one or more TDP-43 target RNAs are independently selected from the group consisting of STMN2 pre-mRNA, ARHGAP32 pre-mRNA, SLC5A7 pre-mRNA, CAMK2B pre-mRNA, KALRN pre-mRNA, CERT1 pre-mRNA, and UNC13A pre-mRNA.

7. The antisense oligonucleotide claim 1, wherein the antisense oligonucleotide is capable of:

(a) enhancing fidelity of pre-mRNA splicing of two or more mRNAs selected from the group consisting of STMN2 mRNA, ARHGAP32 mRNA, SLC5A7 mRNA, CERT1 mRNA, CAMK2B mRNA, KALRN mRNA, and UNC13A mRNA when administered to a TDP-43-depleted cell;

(b) increasing expression of STMN2 when administered to a TDP-43-depleted cell expressing STMN2 pre-mRNA;

(c) decreasing the proportion of STMN2 mature mRNAs comprising a cryptic exon (ce1) between exon 1 and exon 2 as compared to the wildtype STMN2 mature mRNA with an contiguous exon1/exon2 junction when administered to a TDP-43-depleted cell expressing STMN2 pre-mRNA;

(d) decreasing the level of an aberrantly-spliced ARHGAP32 mature mRNA when administered to a TDP-43-depleted cell expressing ARHGAP32 pre-mRNA;

(e) decreasing the level of aberrant exon inclusion in a SLC5A7 mRNA transcript when administered to a TDP-43-depleted cell expressing SLC5A7 pre-mRNA;

(f) decreasing the level of aberrant exon inclusion in a CERT1 mRNA transcript when administered to a TDP-43-depleted cell expressing CERT1 pre-mRNA;

(g) decreasing the level of aberrant exon inclusion in a CAMK2B mRNA transcript when administered to a TDP-43-depleted cell expressing CAMK2B pre-mRNA;

(h) decreasing the level of aberrant exon inclusion in a KALRN mRNA transcript, when administered to a TDP-43-depleted cell expressing KALRN pre-mRNA;

(i) decreasing the level of aberrant exon inclusion in a UNC13A mRNA transcript, when administered to a TDP-43-depleted cell expressing UNC13A pre-mRNA; or (j) correcting aberrant splicing of two or more transcripts selected from the group consisting of STMN2, CERT1, SLC5A7, ARHGAP32, CAMK2B, KALRN, and UNC13A pre-mRNA in a TDP-43-depleted cell.

8. The antisense oligonucleotide of claim 1, wherein the antisense oligonucleotide does not comprise a region of more than 3 or 4 contiguous DNA nucleosides.

9. The antisense oligonucleotide of claim 1, wherein the antisense oligonucleotide is not capable of mediating RNAse H cleavage.

10. The antisense oligonucleotide of claim 1, wherein the antisense oligonucleotide is a morpholino antisense oligonucleotide.

11. The antisense oligonucleotide of claim 1, wherein the one or more modified nucleosides is a 2' sugar-modified nucleoside independently selected from the group consisting of 2'-O-alkyl-RNA; 2'-alkoxy-RNA; 2'-O-methoxyethyl-RNA (2'-MOE); 2'-amino-DNA; 2'-fluro-RNA; 2'-fluoro-DNA; arabino nucleic acid (ANA); 2'-fluoro-ANA; and locked nucleic acid (LNA), or a combination thereof.

12. The antisense oligonucleotide of claim 1, wherein the 2' sugar-modified nucleoside is an affinity-enhancing 2' sugar-modified nucleoside.

13. The antisense oligonucleotide of claim 1, wherein the contiguous nucleotide sequence of the antisense oligonucleotide comprises 2'-MOE nucleosides.

14. The antisense oligonucleotide of claim 13, wherein all of the nucleosides of the contiguous nucleotide sequence are 2'-MOE nucleosides.

15. The antisense oligonucleotide of claim 1, wherein one or more of the modified nucleosides is a LNA nucleoside selected from the group consisting of constrained ethyl nucleoside (cEt) and β-D-oxy-LNA.

16. The antisense oligonucleotide of claim 15, wherein the contiguous nucleotide sequence of the antisense oligonucleotide comprises or consists of LNA nucleosides and DNA nucleosides.

17. The antisense oligonucleotide of claim 1 wherein the antisense oligonucleotide or contiguous nucleotide sequence thereof is a mixmer or a totalmer.

18. The antisense oligonucleotide of claim 1, wherein cytosine bases present in the antisense oligonucleotide or contiguous nucleotide sequence thereof are independently selected from the group consisting of cytosine and 5-methyl cytosine.

19. The antisense oligonucleotide of claim 18, wherein the cytosine bases present in the antisense oligonucleotide or contiguous nucleotide sequence thereof are 5-methyl cytosine.

20. The antisense oligonucleotide of claim 1, wherein:

(a) one or more of internucleoside linkages positioned between the nucleosides of the contiguous nucleotide sequence are modified; or (b) at least 75%, at least about 80%, at least 85%, at least 90%, at least 95%, or 100% of internucleoside linkages positioned between the nucleosides of the contiguous nucleotide sequence are modified.

21. The antisense oligonucleotide of claim 20, wherein one or more of the modified internucleoside linkages comprise a phosphorothioate linkage.

22. The antisense oligonucleotide of claim 21, wherein all of the internucleoside linkages present in the antisense oligonucleotide are phosphorothioate internucleoside linkages.

23. A conjugate comprising the antisense oligonucleotide of claim 1, and at least one conjugate moiety covalently attached thereto.

24. A pharmaceutically acceptable salt of the antisense oligonucleotide of claim 1.

25. The salt according to claim 24, wherein the salt is a sodium salt or a potassium salt.

26. A pharmaceutical composition comprising the antisense oligonucleotide of claim 1 and a pharmaceutically acceptable diluent, solvent, carrier, salt, and/or adjuvant.

27. The antisense oligonucleotide of claim 11, wherein the 2'-O-alkyl RNA is 2'-O-methyl RNA (2'-OMe).

28. A pharmaceutically acceptable salt of the conjugate of claim 23.

29. A pharmaceutical composition comprising the conjugate of claim 23 and a pharmaceutically acceptable diluent, solvent, carrier, salt, and/or adjuvant.

30. A pharmaceutical composition comprising the pharmaceutically acceptable salt of claim 24 and a pharmaceutically acceptable diluent, solvent, carrier, and/or adjuvant.

31. A pharmaceutical composition comprising the pharmaceutically acceptable salt of claim 28 and a pharmaceutically acceptable diluent, solvent, carrier, and/or adjuvant.

* * * * *

SEQUENCE LISTING

<160> NUMBER OF SEQ ID NOS: 129

<210> SEQ ID NO 1
<211> LENGTH: 8
<212> TYPE: DNA
<213> ORGANISM: Artificial Sequence
<220> FEATURE:
<223> OTHER INFORMATION: antisense oligonucleotide

<400> SEQUENCE: 1

```
acacacac                                                                  8


<210> SEQ ID NO 2
<211> LENGTH: 9
<212> TYPE: DNA
<213> ORGANISM: Artificial Sequence
<220> FEATURE:
<223> OTHER INFORMATION: antisense oligonucleotide

<400> SEQUENCE: 2

acacacaca                                                                 9


<210> SEQ ID NO 3
<211> LENGTH: 10
<212> TYPE: DNA
<213> ORGANISM: Artificial Sequence
<220> FEATURE:
<223> OTHER INFORMATION: antisense oligonucleotide

<400> SEQUENCE: 3

acacacacac                                                               10


<210> SEQ ID NO 4
<211> LENGTH: 11
<212> TYPE: DNA
<213> ORGANISM: Artificial Sequence
<220> FEATURE:
<223> OTHER INFORMATION: antisense oligonucleotide

<400> SEQUENCE: 4

acacacacac a                                                             11


<210> SEQ ID NO 5
<211> LENGTH: 12
<212> TYPE: DNA
<213> ORGANISM: Artificial Sequence
<220> FEATURE:
<223> OTHER INFORMATION: antisense oligonucleotide

<400> SEQUENCE: 5

acacacacac ac                                                            12


<210> SEQ ID NO 6
<211> LENGTH: 13
<212> TYPE: DNA
<213> ORGANISM: Artificial Sequence
<220> FEATURE:
<223> OTHER INFORMATION: antisense oligonucleotide

<400> SEQUENCE: 6

acacacacac aca                                                           13


<210> SEQ ID NO 7
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 7

acacacacac acacac                                                        16


<210> SEQ ID NO 8
<211> LENGTH: 18
<212> TYPE: DNA
<213> ORGANISM: Artificial Sequence
```

<220> FEATURE:
<223> OTHER INFORMATION: antisense oligonucleotide

<400> SEQUENCE: 8
acacacacac acacacac 18

<210> SEQ ID NO 9
<211> LENGTH: 7
<212> TYPE: DNA
<213> ORGANISM: Artificial Sequence
<220> FEATURE:
<223> OTHER INFORMATION: antisense oligonucleotide

<400> SEQUENCE: 9 cacacac 7

<210> SEQ ID NO 10
<211> LENGTH: 8
<212> TYPE: DNA
<213> ORGANISM: Artificial Sequence
<220> FEATURE:
<223> OTHER INFORMATION: antisense oligonucleotide

<400> SEQUENCE: 10 cacacaca 8

<210> SEQ ID NO 11
<211> LENGTH: 9
<212> TYPE: DNA
<213> ORGANISM: Artificial Sequence
<220> FEATURE:
<223> OTHER INFORMATION: antisense oligonucleotide

<400> SEQUENCE: 11 cacacacac 9

<210> SEQ ID NO 12
<211> LENGTH: 10
<212> TYPE: DNA
<213> ORGANISM: Artificial Sequence
<220> FEATURE:
<223> OTHER INFORMATION: antisense oligonucleotide

<400> SEQUENCE: 12
cacacacaca 10

<210> SEQ ID NO 13
<211> LENGTH: 11
<212> TYPE: DNA
<213> ORGANISM: Artificial Sequence
<220> FEATURE:
<223> OTHER INFORMATION: antisense oligonucleotide

<400> SEQUENCE: 13
cacacacaca c 11

<210> SEQ ID NO 14
<211> LENGTH: 12
<212> TYPE: DNA
<213> ORGANISM: Artificial Sequence
<220> FEATURE:
<223> OTHER INFORMATION: antisense oligonucleotide

<400> SEQUENCE: 14
cacacacaca ca 12

<210> SEQ ID NO 15
<211> LENGTH: 13
<212> TYPE: DNA
<213> ORGANISM: Artificial Sequence
<220> FEATURE:
<223> OTHER INFORMATION: antisense oligonucleotide

<400> SEQUENCE: 15
cacacacaca cac 13

<210> SEQ ID NO 16
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 16
cacacacaca cacaca 16

<210> SEQ ID NO 17

<400> SEQUENCE: 17

000

<210> SEQ ID NO 18
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 18
cacacacaca cacacaca 18

<210> SEQ ID NO 19
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 19
tccacactga acaaacc 17

<210> SEQ ID NO 20
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 20
cacacacaca cacacacaca cac 23

<210> SEQ ID NO 21
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 21
acacacacac acacacacac acac 24

<210> SEQ ID NO 22
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 22
cacacacaca caacacacac acac 24

<210> SEQ ID NO 23
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 23
cacacacaca cacacacaca cacac 25

<210> SEQ ID NO 24
<211> LENGTH: 26
<212> TYPE: DNA
<213> ORGANISM: Artificial Sequence
<220> FEATURE:
<223> OTHER INFORMATION: antisense oligonucleotide

<400> SEQUENCE: 24
acacacacac acacacacac acacac 26

<210> SEQ ID NO 25
<211> LENGTH: 27
<212> TYPE: DNA
<213> ORGANISM: Artificial Sequence
<220> FEATURE:
<223> OTHER INFORMATION: antisense oligonucleotide

<400> SEQUENCE: 25
cacacacaca cacacacaca cacacac 27

<210> SEQ ID NO 26
<211> LENGTH: 28
<212> TYPE: DNA
<213> ORGANISM: Artificial Sequence
<220> FEATURE:
<223> OTHER INFORMATION: antisense oligonucleotide

<400> SEQUENCE: 26
acacacacac acacacacac acacacac 28

<210> SEQ ID NO 27
<211> LENGTH: 28
<212> TYPE: DNA
<213> ORGANISM: Artificial Sequence
<220> FEATURE:
<223> OTHER INFORMATION: antisense oligonucleotide

<400> SEQUENCE: 27
cacacacaca cacacacaca cacacaca 28

<210> SEQ ID NO 28
<211> LENGTH: 30
<212> TYPE: DNA
<213> ORGANISM: Artificial Sequence
<220> FEATURE:
<223> OTHER INFORMATION: antisense oligonucleotide

<400> SEQUENCE: 28
acacacacac acacacacac acacacacac 30

<210> SEQ ID NO 29
<211> LENGTH: 31
<212> TYPE: DNA
<213> ORGANISM: Artificial Sequence
<220> FEATURE:
<223> OTHER INFORMATION: antisense oligonucleotide

<400> SEQUENCE: 29
cacacacaca cacacacaca cacacacaca c 31

<210> SEQ ID NO 30
<211> LENGTH: 34
<212> TYPE: DNA
<213> ORGANISM: Artificial Sequence
<220> FEATURE:
<223> OTHER INFORMATION: antisense oligonucleotide

<400> SEQUENCE: 30
acacacacac acacacacca cacacacaca caca 34

<210> SEQ ID NO 31
<211> LENGTH: 34
<212> TYPE: DNA
<213> ORGANISM: Artificial Sequence
<220> FEATURE:
<223> OTHER INFORMATION: antisense oligonucleotide

<400> SEQUENCE: 31
cacacacaca cacacacaca cacacacaca caca 34

<210> SEQ ID NO 32
<211> LENGTH: 36
<212> TYPE: DNA
<213> ORGANISM: Artificial Sequence
<220> FEATURE:
<223> OTHER INFORMATION: antisense oligonucleotide

<400> SEQUENCE: 32
cacacacaca cacacacaac acacacacac acacac 36

<210> SEQ ID NO 33
<211> LENGTH: 36
<212> TYPE: DNA
<213> ORGANISM: Artificial Sequence
<220> FEATURE:
<223> OTHER INFORMATION: antisense oligonucleotide

<400> SEQUENCE: 33
acacacacac acacacacca cacacacaca cacaca 36

<210> SEQ ID NO 34
<211> LENGTH: 32
<212> TYPE: DNA
<213> ORGANISM: Artificial Sequence
<220> FEATURE:
<223> OTHER INFORMATION: antisense oligonucleotide

<400> SEQUENCE: 34
acacacacac acacacacac acacacacac ac 32

<210> SEQ ID NO 35

<211> LENGTH: 12
<212> TYPE: RNA
<213> ORGANISM: Artificial Sequence
<220> FEATURE:
<223> OTHER INFORMATION: human RNA TDP-43 binding site

<400> SEQUENCE: 35
ugugugugug ug 12

<210> SEQ ID NO 36
<211> LENGTH: 16
<212> TYPE: DNA
<213> ORGANISM: Artificial Sequence
<220> FEATURE:
<223> OTHER INFORMATION: LNA/DNA mixmer which targets and upregulates the expression of STMN2

<400> SEQUENCE: 36
cacacacgca cacatg 16

<210> SEQ ID NO 37
<211> LENGTH: 10
<212> TYPE: RNA
<213> ORGANISM: Artificial Sequence
<220> FEATURE:
<223> OTHER INFORMATION: sequence complementary to antisense oligonucleotide

<400> SEQUENCE: 37
ugugugugug 10

<210> SEQ ID NO 38
<211> LENGTH: 11
<212> TYPE: RNA
<213> ORGANISM: Artificial Sequence
<220> FEATURE:
<223> OTHER INFORMATION: sequence complementary to antisense oligonucleotide

<400> SEQUENCE: 38
ugugugugug u 11

<210> SEQ ID NO 39
<211> LENGTH: 13
<212> TYPE: RNA
<213> ORGANISM: Artificial Sequence
<220> FEATURE:
<223> OTHER INFORMATION: sequence complementary to antisense oligonucleotide

<400> SEQUENCE: 39
ugugugugug ugu 13

<210> SEQ ID NO 40
<211> LENGTH: 10
<212> TYPE: RNA
<213> ORGANISM: Artificial Sequence
<220> FEATURE:
<223> OTHER INFORMATION: sequence complementary to antisense oligonucleotide

<400> SEQUENCE: 40
gugugugugu 10

<210> SEQ ID NO 41
<211> LENGTH: 11
<212> TYPE: RNA

<213> ORGANISM: Artificial Sequence
<220> FEATURE:
<223> OTHER INFORMATION: sequence complementary to antisense
oligonucleotide

<400> SEQUENCE: 41
gugugugugu g 11

<210> SEQ ID NO 42
<211> LENGTH: 12
<212> TYPE: RNA
<213> ORGANISM: Artificial Sequence
<220> FEATURE:
<223> OTHER INFORMATION: sequence complementary to antisense
oligonucleotide

<400> SEQUENCE: 42
gugugugugu gu 12

<210> SEQ ID NO 43
<211> LENGTH: 13
<212> TYPE: RNA
<213> ORGANISM: Artificial Sequence
<220> FEATURE:
<223> OTHER INFORMATION: sequence complementary to antisense
oligonucleotide

<400> SEQUENCE: 43
gugugugugu gug 13

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
cagctcatcc tcagtcatgt c 21

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
gatggtgtga ctgcaaactt c 21

<210> SEQ ID NO 46
<211> LENGTH: 14
<212> TYPE: RNA
<213> ORGANISM: Artificial Sequence
<220> FEATURE:
<223> OTHER INFORMATION: sequence complementary to antisense
oligonucleotide

<400> SEQUENCE: 46
ugugugugug ugug 14

<210> SEQ ID NO 47
<211> LENGTH: 14
<212> TYPE: RNA
<213> ORGANISM: Artificial Sequence
<220> FEATURE:
<223> OTHER INFORMATION: sequence complementary to antisense oligonucleotide

<400> SEQUENCE: 47
gugugugugu gugu 14

<210> SEQ ID NO 48
<211> LENGTH: 18
<212> TYPE: RNA
<213> ORGANISM: Artificial Sequence
<220> FEATURE:
<223> OTHER INFORMATION: sequence complementary to antisense oligonucleotide

<400> SEQUENCE: 48
ugugugugug ugugugug 18

<210> SEQ ID NO 49
<211> LENGTH: 18
<212> TYPE: RNA
<213> ORGANISM: Artificial Sequence
<220> FEATURE:
<223> OTHER INFORMATION: sequence complementary to antisense oligonucleotide

<400> SEQUENCE: 49
gugugugugu gugugugu 18

<210> SEQ ID NO 50
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (12)..(12)
<223> OTHER INFORMATION: n is inosine

<400> SEQUENCE: 50
cacacaccca cncacacacg cac 23

<210> SEQ ID NO 51
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (6)..(6)
<223> OTHER INFORMATION: n is inosine

<400> SEQUENCE: 51
cacacncaca cacacacaca cac 23

<210> SEQ ID NO 52
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (12)..(12)
<223> OTHER INFORMATION: n is inosine

<400> SEQUENCE: 52
cacacacaca cncacacaca cac 23

<210> SEQ ID NO 53
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (6)..(6)
<223> OTHER INFORMATION: n is inosine

<400> SEQUENCE: 53
cacacncaca cacacacaca ctc 23

<210> SEQ ID NO 54
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 54
cacatacaca cccacacaca cac 23

<210> SEQ ID NO 55
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 55
cacacacaca cacacacgca cac 23

<210> SEQ ID NO 56
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (20)..(20)
<223> OTHER INFORMATION: n is inosine

<400> SEQUENCE: 56
cacncacnca cacacncacn cac 23

<210> SEQ ID NO 57
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 57
cacacacaca cacactctca cac 23

<210> SEQ ID NO 58
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 58
ctcacacaca cacacacaca cac 23

<210> SEQ ID NO 59
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 59
cacacacaca caaacacaca cac 23

<210> SEQ ID NO 60
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 60
cacacgcacg cacacacaca cac 23

<210> SEQ ID NO 61
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 61
cacgcacaca cccacacact cac 23

<210> SEQ ID NO 62
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 62
cacacacaca cactctctca cac 23

<210> SEQ ID NO 63
<211> LENGTH: 23
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (20)..(20)
<223> OTHER INFORMATION: n is inosine

<400> SEQUENCE: 63
cacacacaca cacncncncn cac 23

<210> SEQ ID NO 64
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 64
cactcacaca ctcacacaca cac 23

<210> SEQ ID NO 65
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 65
cacgcacaca cgcacacaca cac 23

<210> SEQ ID NO 66
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 66
cacccacaca cccacacaca cac 23

<210> SEQ ID NO 67
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 67
cacacgcaca tacacacacc cac 23

<210> SEQ ID NO 68
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 68
ttcacacaca cacacacaca cac 23

<210> SEQ ID NO 69
<211> LENGTH: 23
<212> TYPE: DNA
<213> ORGANISM: Artificial Sequence
<220> FEATURE:
<223> OTHER INFORMATION: antisense oligonucleotide

<400> SEQUENCE: 69
cacacacaca cacacacaca caa 23

<210> SEQ ID NO 70
<211> LENGTH: 29
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (21)..(21)
<223> OTHER INFORMATION: n is inosine

<400> SEQUENCE: 70
cacacacaca cacacacaca nacacacac 29

<210> SEQ ID NO 71
<211> LENGTH: 29
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (5)..(5)
<223> OTHER INFORMATION: n is inosine

<400> SEQUENCE: 71
cacanacaca cacacacaca cacacacac 29

<210> SEQ ID NO 72
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 72
catacacaca cacacacaca tacacacac 29

<210> SEQ ID NO 73
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 73
caaacacaca cacacacaca cacacacac 29

<210> SEQ ID NO 74
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 74
cacacacact cacacacaca cacacacac 29

<210> SEQ ID NO 75
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 75
cacagacaca cacacacaca cacacacac 29

<210> SEQ ID NO 76
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 76
cacaaacaca cacacacaca cacacacac 29

<210> SEQ ID NO 77
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 77
cacatacaca cacacacaca cacacacac 29

<210> SEQ ID NO 78
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 78
catacgcaca tacacgcaca cacaaacac 29

<210> SEQ ID NO 79
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 79
cacatataca catacacaca cacacacac 29

<210> SEQ ID NO 80
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 80
cacacacaca cacacacact ctctctctc 29

<210> SEQ ID NO 81
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 81
cacgcacaca cacacacaca cacacacac 29

<210> SEQ ID NO 82

<211> LENGTH: 29
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (17)..(17)
<223> OTHER INFORMATION: n is inosine
<220> FEATURE:
<221> NAME/KEY: misc_feature
<222> LOCATION: (19)..(19)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 82
cacacacaca cacacantnt ntcacacac 29

<210> SEQ ID NO 83
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 83
cgcacacaca cacacacaca cacacacac 29

<210> SEQ ID NO 84
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 84
cacacacaca cacacagaca gacagacac 29

<210> SEQ ID NO 85
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 85
cacacacaca aaaaaacaca cacacacac 29

<210> SEQ ID NO 86
<211> LENGTH: 29
<212> TYPE: DNA
<213> ORGANISM: Artificial Sequence
<220> FEATURE:
<223> OTHER INFORMATION: antisense oligonucleotide

<400> SEQUENCE: 86
cacacacaca cccccccaca cacacacac 29

<210> SEQ ID NO 87
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 87
cacacacact ctctcacaca cacac 25

<210> SEQ ID NO 88
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 88
cacaaacaca cacacacaca cacac 25

<210> SEQ ID NO 89
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 89
cactcacaca cacacacaca cacac 25

<210> SEQ ID NO 90
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 90
cacacacaca aacacacaca cacac 25

<210> SEQ ID NO 91
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 91
cacccacaca cacacacaca cacac 25

<210> SEQ ID NO 92
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 92
ctctctcaca cacacacaca cacac 25

<210> SEQ ID NO 93
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 93
caaacacaca cacacacaca cacac 25

<210> SEQ ID NO 94
<211> LENGTH: 25
<212> TYPE: DNA

<213> ORGANISM: Artificial Sequence
<220> FEATURE:
<223> OTHER INFORMATION: antisense oligonucleotide

<400> SEQUENCE: 94
cacacacacc cacacacaca cacac 25

<210> SEQ ID NO 95
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 95
cacacacaca cacacccaca cacac 25

<210> SEQ ID NO 96
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 96
cacacacaca cacacgcaca cacac 25

<210> SEQ ID NO 97
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 97
cacacacaca cacactcaca cacac 25

<210> SEQ ID NO 98
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 98
cacacacaca tacacacaca cacac 25

<210> SEQ ID NO 99
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 99
cacacacaca gacacacaca cacac 25

<210> SEQ ID NO 100
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 100
tttacacaca cacacacaca cacac 25

<210> SEQ ID NO 101
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 101
cacgcacacg cacacacaca cacac 25

<210> SEQ ID NO 102
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 102
cacgcacaca cgcacacaca cgcac 25

<210> SEQ ID NO 103
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 103
cacacgcaca cacacacaca cacac 25

<210> SEQ ID NO 104
<211> LENGTH: 23
<212> TYPE: DNA
<213> ORGANISM: Artificial Sequence
<220> FEATURE:
<223> OTHER INFORMATION: Probe

<400> SEQUENCE: 104
cagcgcccca caaacacttt tct 23

<210> SEQ ID NO 105
<211> LENGTH: 15
<212> TYPE: DNA
<213> ORGANISM: Artificial Sequence
<220> FEATURE:
<223> OTHER INFORMATION: primer

<400> SEQUENCE: 105
ctgctcagcg tctgc 15

<210> SEQ ID NO 106
<211> LENGTH: 15
<212> TYPE: DNA
<213> ORGANISM: Artificial Sequence
<220> FEATURE:
<223> OTHER INFORMATION: primer

<400> SEQUENCE: 106
gttgcgaggt tccgg 15

<210> SEQ ID NO 107
<211> LENGTH: 26
<212> TYPE: DNA
<213> ORGANISM: Artificial Sequence
<220> FEATURE:

<223> OTHER INFORMATION: probe

<400> SEQUENCE: 107
caatggccta caaggaaaaa atgaag 26

<210> SEQ ID NO 108
<211> LENGTH: 24
<212> TYPE: DNA
<213> ORGANISM: Artificial Sequence
<220> FEATURE:
<223> OTHER INFORMATION: primer

<400> SEQUENCE: 108
ctaatggtta aacgtgagga cagc 24

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
atctggtcct ccaaagtggg 20

<210> SEQ ID NO 110
<211> LENGTH: 34
<212> TYPE: DNA
<213> ORGANISM: Artificial Sequence
<220> FEATURE:
<223> OTHER INFORMATION: probe

<400> SEQUENCE: 110
ctggataagg aaactgagaa gaaaagaaga acag 34

<210> SEQ ID NO 111
<211> LENGTH: 17
<212> TYPE: DNA
<213> ORGANISM: Artificial Sequence
<220> FEATURE:
<223> OTHER INFORMATION: primer

<400> SEQUENCE: 111
cgagccctcg gagtttg 17

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
tccttccaag aaatggtggc 20

<210> SEQ ID NO 113
<211> LENGTH: 22
<212> TYPE: DNA
<213> ORGANISM: Artificial Sequence
<220> FEATURE:
<223> OTHER INFORMATION: probe

<400> SEQUENCE: 113
gaatatgatg ctgctgctga tg 22

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
ctgacagtgc caataccacc 20

<210> SEQ ID NO 115
<211> LENGTH: 19
<212> TYPE: DNA
<213> ORGANISM: Artificial Sequence
<220> FEATURE:
<223> OTHER INFORMATION: primer

<400> SEQUENCE: 115
gctgctccgt ggtcttaat 19

<210> SEQ ID NO 116
<211> LENGTH: 26
<212> TYPE: DNA
<213> ORGANISM: Artificial Sequence
<220> FEATURE:
<223> OTHER INFORMATION: probe

<400> SEQUENCE: 116
atgaagacgc taaagcccgg aagcag 26

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
gatcaaaggc gaggagaagg 20

<210> SEQ ID NO 118
<211> LENGTH: 19
<212> TYPE: DNA
<213> ORGANISM: Artificial Sequence
<220> FEATURE:
<223> OTHER INFORMATION: primer

<400> SEQUENCE: 118
tggcatctgg gatcttcac 19

<210> SEQ ID NO 119
<211> LENGTH: 21
<212> TYPE: DNA
<213> ORGANISM: Artificial Sequence
<220> FEATURE:
<223> OTHER INFORMATION: probe

<400> SEQUENCE: 119
catgagaacc tgttccactt c 21

<210> SEQ ID NO 120
<211> LENGTH: 333
<212> TYPE: DNA
<213> ORGANISM: Homo sapiens

<400> SEQUENCE: 120

```
agtcttctct ctcgctctct ccgctgctgt agccggaccc tttgccttcg ccactgctca     60

gcgtctgcac atccctacaa tggctaaaac agcaatggga ctcggcagaa gaccttcgag    120

agaaaggtag aaaataagaa tttggctctc tgtgtgagca tgtgtgcgtg tgtgcgagag    180

agagagacag acagcctgcc taagaagaaa tgaatgtgaa tgcggcttgt ggcacagttg    240

acaaggatga taaatcaata atgcaagctt actatcattt atgaatagca atactgaaga    300

aattaaaaca aaagattgct gtctcaatat atc                                 333
```

<210> SEQ ID NO 121
<211> LENGTH: 2755
<212> TYPE: DNA
<213> ORGANISM: Homo sapiens

<400> SEQUENCE: 121

```
gaaattaatc cttttggtag tcatattagg tagaatcatg atgcacattc taataagtca     60

cactgtactc atgtcccttt agcctggaaa ccatctccct gaaactggaa ctcagctttt    120

tcgtctgtat ctgtaatgct ttcatgatgc ctggaaaata gaagagactt aataaataca    180

tgattgatga gtgagtgagc gagtgaatga atgaagagaa aagagcagaa acgaaaccaa    240

aactgtcaag aaaaaaaaat caaagatcaa ttcttgtcat acttacttcc tacttctttt    300

agccatattc taatctaaag gatcatcgat tttaatttaa atatgtactt cttattctgt    360

tgtcgtatga tgatatttta aaaactaaga atgtaaaatc aaagtaaatc agaagtgtat    420

tatgtggaga atgtgggaat gattctgaaa gtcataccgt cttttggagg aagcattttg    480

gaggtttcta atgttatatt ttgactgggt cattattcgc tgtgcatttg gctggtttgt    540

tagatggttt gggggtagct agtaaatagc cttttttaa aactaggatt ttttttacaa     600

aatatattgg atttcttata ttgctttcct actctttcgt gaaaaaataa aacagatctt    660

ttcttctttt ttcttctgac attgtttttc agtttttgct ccttttcttc aagattcaag    720

tttatgcttt tctttcattt tgccacctat ttgtattaaa tgactcattt gtttccctta    780

aacttataag taatagttat gtaattttat ttattaagct cattatgtga tttttgtgta    840

gacattcagt ccttctactc agggaacaca aaatataaga aaacgattca gatgcttgcc    900

atgaagtatt acgtgtgtag agacttggac atattatcag gaaaagacct ctaattctcc    960

atattttcaa tgttttccta cttatttgga agaataaaca gatatgaatc taataacaca   1020

cagatataca catccaatga aaattaccga tacttttttt tataaatggt agcttatttt   1080

tatgaaaaat ttatgtgtgc tcggagagcc tgataatatg gaaataaaat actgtgctct   1140

gaagggtttt tcttgaagac aaaccttttg tgtacctggg tgaatcagca tgctcatttg   1200

gagcatatat aatgagaagc atcttctcag tgctttacag gaaagaattt taactatttt   1260

cctaagtaat gatgttaatt atcccagtaa tctctaaata cattcccttt gaagcagaag   1320

actgaaattt tgtagcccca aattttatta ttccacttcc agtttttaga attgaaacct   1380

aagacaccaa gtttatcatt ggtgggacaa tgtgagaaat agaacccaag cttttataaa   1440

gatgctatgt attttgcata tcatttcgac acagaggttg cttctaatat caattaaatc   1500

cacaagaagt acccagcaat tctacctgcc cttcatcttt actacataac cataaccttt   1560

tcttgttact gaaagtcttg aatattttta gaggtagaaa gcatgtagtt gaaaatgtat   1620

tcatatgaaa actaaggttc cttccctgct aacttgacca gataatgacc atttcaggct   1680

ctcagggcac tggtaaatta attcacttgc taattttata cattgtgtca ggacggtgtt   1740

cctgagtttt aaatatacaa agatggacga tgcatggttt tgctcttgaa gagcccacag   1800
```

```
tcagaaaagg gtaatagttg tatgaacaaa taaatgataa ttttgaaata tttttctatg   1860

agcacataga acacagtgct cagccacctc tacttgtggg tattcaatga aggctcgcta   1920

aagagtgata gtttacctgg attttgaaca atagccaaga attttttcta tacgaagagc   1980

gttatgggag agagtccagc tagaggaaat tgttttgtga agaagtcata gcatggttgg   2040

tttgtatggc aaaaggtaac acttcacttg gcctagggtt gtggaatatg gaaatacaat   2100

aataattaaa tgtaaattat gaaaggcctt ctctgccagg cagtatattg cagtagtcaa   2160

aagcattggc tctgactgga taaagaaaaa tgtggcacat atataccatg gaatactatg   2220

cagccataaa aaaggatgag ttcatgtcct ttgcagggac atggatgaag ttggaagcca   2280

tcattctcag caaactatca caagaacaga aaaccaaaca ccacatgttc tcactcataa   2340

gtgggagttg aacaatgaga acacatggaa tagggagggg aacatcacac accagggcct   2400

ctcggggggt tggggggcta ggggagggat aacattagga gaaatactca atgtagatga   2460

tgggttgatg ggtgcagcaa accaccatgg catgtgtata cttacgtaac aaaactgcac   2520

attctgcaca tgtaccccag aacttaaagt ataataaaaa aagatatatg tatgtgtgtg   2580

tgtgtgtgtg tgtgtgtgtg tgtgtgtgtg tgaaataaaa aacaaaacaa aagcattggc   2640

tctgtacttg gactgcctga gttggaatct ctcacttctg ccagtgtttc ctgcctgccc   2700

ttgggtaaaa cttactctct ctaagataca atttcttctc tgtaaaaatt gggaa        2755
```

<210> SEQ ID NO 122
<211> LENGTH: 352
<212> TYPE: DNA
<213> ORGANISM: Homo sapiens

<400> SEQUENCE: 122

```
cttttgtcct gtggtattct gtaaaggtga tccagggtga tgttcctaca gcaactttga     60

ctttcgatta gtagagtctt ttattggatt gtttaacttt taggagagca gtcctggttc    120

atagtgtaca ctctccattc cagttgttca tccaggagac agacacttca aaaatgtaaa    180

gatgactgac gaaggtggta tgtagtgttt gtctctgaaa aaaaaaaaga tagtatttct    240

ctcacaagca gaaaacatat atggacgtgt gtgtgtctgt gtgtgtgtgt gtgtgtgtgt    300

ctgtgtgtgt gtgtttattg taggaacaca ggctaacaga aacagcatta ag            352
```

<210> SEQ ID NO 123
<211> LENGTH: 404
<212> TYPE: DNA
<213> ORGANISM: Homo sapiens

<400> SEQUENCE: 123

```
acactctcca ccaaagaaca gccagaaaag atggcaggca gtattggtta aaatctggac     60

actactgtgt tttatagtct tcttacagat ctatctgatg tcaaatttta ttaacctttt    120

ccactgtaat tttttctcaa ggttgaaata actggatccc agttacattt tacatggaat    180

gtaagtgtgt gtgtatttgc acatgtgtgt acacacagta tgtgtgtgtt catatatata    240

tacataatat atgcagggta tgtgtgtatt tattggtaag caactctatt caagaacttt    300

ctaatctttt gtatgtagag tgtgtgtgtg tgtgtgtgtg tatatataca cactaaagac    360

tagaaagttc ttaaatagag aaagttgttt atcaacaaat acgt                     404
```

<210> SEQ ID NO 124
<211> LENGTH: 16
<212> TYPE: PRT

<213> ORGANISM: Homo sapiens

<400> SEQUENCE: 124

Met Ala Lys Thr Ala Met Gly Leu Gly Arg Arg Pro Ser Arg Glu Arg
1 5 10 15

<210> SEQ ID NO 125
<211> LENGTH: 10231
<212> TYPE: DNA
<213> ORGANISM: Homo sapiens

<400> SEQUENCE: 125
gagtcttctg acagtgccaa taccaccata gaggatgaag acgctaaagg tacctgcact 60
tgagtccttg cccccccagc ggccttggca ttgctgggtt gctctttgag gtgggtggga 120
cttgggcagg gtcaactctc ctgcgacgcc tagtttatgc atgtgttgag gggctcaggg 180
accctgtagc tgtaatcctg ctccaagcct gggtgtcagg cctgcccaga gcggagaagc 240
atggcagaga tgaccgacag ctgggcagtc tcggtcaccg catccaagtg aggaagccac 300
ggctttgcat ggaggcaggt tctccacacc aggaccctca cggggaaaca ggcccatggg 360
tagaatttgt tccaagatgc tgtccttgtc ttaaagctcc ttaagcttgc gtttctgtcc 420
agcatgcact tgccaagtgg ccgggcagct gggtgagtgt ttccgtgttt gcctttgctt 480
agccaggagt gtcctgctgc ggtgggtttc tgcaccacag attccagggc cccctccctt 540
gctcacccag gccaatgtct tgtgtgttcc ccaagaggcc cccagggcac caggcactgg 600
ggcatgctcc atggattctg ccgcctccag accacccaca tggggcctcc tgaccctcat 660
cgctcacacg gtcacctaat aagccttatg ctgttctcag ggctaccctg gtgcccaaaa 720
agggtcagcc actctgccag tttaggggag aaaacttctc acctgtccaa agcatagcct 780
tgctcctgcc cggcctaccc agctatgaca ctgtccctga gcagagatga gcacaggact 840
ttgggccctg gatgccggag agtgggtgtt tgtgtgattc ccctgcagtc tggaacaggc 900
cccaaaggca acagcatgaa ggctgtccag aggttctcca tcaccctcag ccgagtgggg 960
tgctgagcag tgagggaggg gacctgggag gggggcccag cctggatcct gcaggggaga 1020
agagaagaca gccagaagcc agcagctgtg gctcagatct gagcccgagc agcctctcga 1080
ggtggaggca gacacccccc accccacccc gtgcagaaag aagccttgcc agcctgccct 1140
gaggctggta cagagtccag gcaggctcag tggccatcat gcccctacga tgactgtcac 1200
tccctctccg tgcgcctggc ctctgctggc tctggccagg ggtggtcaca gcactagggt 1260
ggcagggtgg cctctgactc tgcgccagcc tgcactggcc tgtgctgccc tggcctctgc 1320
tggctctggc tctggcaccg gtcccgtgtt ggctccttca gccttcacat acctgctgcg 1380
gccaccacag gcccaggacc cccacaggtg gccaccccac ctccacccca ggagccccag 1440
gtatccagct gtcacccccct ccctccctcc tggcctcccc ctgtccttct ccagttgcct 1500
tcttttcctg cgggcgcacc acccacctgc ctgcctcacc tgttccgcct cagcccccag 1560
ggtccccgac atcctgagct cagtgaggag gggctcggga gccccagaag ccgaggggcc 1620
cctgccctgc ccatctccgg ctccctttag ccccctgcca gccccatgta agtagcctgg 1680
gtcctgctgc tgtgggggtc atgttggagg gctggcaacc ccctagaggg gccactccag 1740
agccgagggc aggctgagcg tggaccctgg ctccagcctc atcaccccac aatccctcac 1800
tggggctttc cagggtggcc ccagcccatc gagccccacc tctttgtgag gagggccctg 1860
gaccactttc ctgctcaagg ccactgggca ggatgggagg ccctggaggc tcgggcctca 1920

```
attccagtct tcagggtcgg tgcaggcctc actccacctc agcttgcggg cggggggct   1980
ccctgctatt gaggcaggct ctgattcagg gcctgatccc agggcccaag ggtctagaa   2040
cacgggaccc ctcccactgg cctcctccgc cttgccgccg cctcgtgtgt ctgtctgcct   2100
catgttcacg tctcatctgt tccaccccag cccccaggat ctctgacatc ctgaactctg   2160
tgagaagggg ttcaggaacc ccagaagccg agggcccct ctcagcgggg cccccgccct   2220
gcctgtctcc ggctctccta ggcccctgt cctccccgtg taagtagtgg cccccaggcc   2280
tgccgcctct gctgccggac agctccctgc gaatggccgg cgctcagcag cttcccacct   2340
gcatgcacgg cccagctacc ctgccccggc gccgcagcct ggagtcctgc cctggcgggg   2400
cttcctgtgg gctcccatgc taaccagcag ggcagctcct ggcttctccc taaggggccc   2460
agacccctcc acggctcctg ctcccactgc cactccccgc tcgctgtcca gccccaggcc   2520
cctctccaaa atgtctgtcc cagccctggg cagccctggc ccctccgagg cccccatgc   2580
ccctaggccc tctctgctga tcactgtccc agccccacag acttcacacc cacccagggg   2640
ccctgcccat ggtgcccagg agctgcactc agggccaccc tggttcctga tgtggcccca   2700
accccctgagc accctccctc agtctaggag gctgaggaag gtgccaaaac tggaaccccg   2760
accagggtct ctggagctca ccaacaaggg gatagtacgg agaatcataa gcctggcctc   2820
tgctgacctg ggctgtcctc atggggccag gccaggcctc ctctgtaacg cccgtgactc   2880
cctcctctcc ctgtaacccc gtccagcgtt cctcaagggc cacttacctg acagcttctt   2940
gctggccagc agcctctccc tggagggtgc cctctgcccc cagcagcttc agcccacgcc   3000
acccgacagc cagagcatct gcccttcact cctgcagcct cctctccacg caccacgctg   3060
tccgcagcag caccctctgt ccccctgtct ccctccgtcc ccccatatcc ccctcggtca   3120
gcctacaacc tctccacgtc cccctaagtc cacgctctat ccctacatcc ccctctgtcc   3180
cccaaattcc cctctttccc tcatttccat tttcctcccc aaactctgct ctgcccctca   3240
cattctccct ctgtccccca caccctcctc tgtcccccag actctccctc tgtcccccac   3300
accctcctct gtcccccata taccccctctg tcccccacac ccaccttggt cccttcacgc   3360
ccttttctgt cccccacacc ccctctgttc cctacactct ccctctgtcc tccagaccct   3420
cctctgtccc ccacactccc tctgtccccc acaccccctg tcccccacac tctccctctg   3480
ccccccagac cctcctctgt cccctacact ccctctgtcc cccatatccc cctctgtccc   3540
ccacaccctc ctctgtcctc caccccctgc cccccatacc cccttctgtc ccccacactt   3600
cctctgtctt ccacaccccc tcctgtcccc cacacccccct ctgtccccca gactctccct   3660
ctgtccccca cactccgtct gtcccccaca cctcctgtct tccacacccc cttctgtccc   3720
ccacaccccc tctgtccccc atactctcct ctgtccccca cctccccctc tgttccccac   3780
accgccttct gtcccccaca ccccctctgt cttccacttc ccctctgtcc ccccacatccc   3840
cctctgtccc ctgcaccctc ctctgtcccc tgcaccctcc tctgtcccct gcacctctct   3900
ctgtccccca catccccctc tgtcctccac actccctctg tcccccacat ccaccttggt   3960
cccctcacgc acccccatcc cccatgaccc cttctgtccc ccacaccccc tctgtcttcc   4020
acacccccct ctgtccccca cacccacctt ggtcccctca tgccccccat cccctacacc   4080
cccactttgt ccccccacat gcccctctgt cccccacgtt cccttctgtc tcccacgtct   4140
cctccatttc ccgtttccct ctctgtcccc caagctcccc tccatccccc acatcccctt   4200
ctttccccta tatcccctct gtcggcccag gtccaccatc ttccccccac acccccccat   4260
tctcccttcc tcccctctgt ccccttgtgc cccatccccc acatctgcct ctgtgcccct   4320
```

```
caatctctgg cttggctgtc tgcccatggt ttctctcctg cgtgcccccc gtgcctgcct   4380
tgtgttcacg tctcgtctgt tccgccccag cccccaggat ctctgacatc ctgaactctg   4440
tgaggagggg ctcagggacc ccagaagccg agggcccctc gccagtgggg cccccgccct   4500
gcccatctcc gactatccct ggccccctgc ccaccccatg taagtagcac cttgagtggc   4560
cgtggcagcg gctgcccgga ggggctcggg gcgtgcgagc ctggcagtgg tgctctggga   4620
agggccattc ttgcggagga gggcggggca caggatccct ctgctgggtc ccagggaatt   4680
gctttgaagc acatgaaggt gccactgggt ctcagaaaat ggaggttatg gttatgaagt   4740
gtgtatgaca tatgtgtata ggaagagcgt ccgaaagagc aggtttgttg ccgaccccag   4800
cattcgcaac cctgaggtcc acagctttct cctgatggga ggggaatggg tggcaaaggg   4860
tctgcgcgtg tggcaagggc tagcacgcca ggagctgctg gcttgggtca aggtggacct   4920
gctgggccgg gacagaaaag tgtcagtccc ggcctgagac gctctagcat tagagctgtc   4980
caagtccaga cagcagggag caggtgggga tcgggaggcg cggatctggg ggcagctgg   5040
ggccaggctg aaacagagcg ggcgggacag gaagcacagg ctgggcagcc tccccggcca   5100
gggaggagcc aggctgggcc acctcccggt ctgtctgccg actacccgca gtatcactta   5160
cagggatgga tgacatccca gggctgctgc cacccccacc tgtggggaga caccagactg   5220
ggggtggtgt ggagatactc ttagagaaga ggctgctggg ccacgggctc ggcatggcag   5280
ggcagtggct aggtaagtac ttgagggaca ggtggggtct gcttgccacc gtcccctctg   5340
caggctgggc ctgggggctg ctgcaggcgg ccagggcaga agggtgtggg gagagtgaac   5400
ccacaggagc agcggctcga ggaggggggat gcaggctgca ggctcaaagg ggcactggat   5460
ccaccctggg tgcccgagag agcagggggc agcccctgga ggggtactca cccccagagc   5520
ttctgtggtc ggctgaggac ccccagcagg ggttgactga ggggatcaga ggcaagcagc   5580
tgaggggaga ggccaggttc ttgatgctga tagggtcggg gtgcctgggc gaccagaact   5640
caaggaggga ggcatgggga ggggccgccg tgcagctggg gtgggtgcac cgcagagcct   5700
ctgggagtgg tcagaacccc cgacacctgc cacttctaca gcagctcatc tgattttaag   5760
gggcttgctg cccttgcaga agtggagggg tgtgcccaaa ggagcctgcc tggaaggtca   5820
ccccatcagg ttggcatgac cccagcccag gactgcagcc tgccctcaag gtctgtgcag   5880
tatctggggt gagtcctctg aggacagggc ccagggtggg tgtggagtgg ccagctcggg   5940
gctcggtgtc caggctcacc ttcaggggcc acagcacaga cctgcccttc cagagtcttc   6000
cctgagcttg gctggggagg agggggctgc aggaaggagc tgtgagcagg gcaggatgga   6060
gattcgtgtg gccctcctgg gaggggctgg gcagggctgg gaaaggggtg ggtgagatgt   6120
tccggaactc agggaaagga agagtctggg tactgccctg gggcacctg ggcccaggtg   6180
gcaggtggcc agctttctgc ctcctttcca cctcctttct ccagaaggca cccaccagct   6240
gtgtaaatag ggcaggtgcc cacggcccgc ctcaggcccc gtctcctccc cacccacgct   6300
ctctaatcgc ggattataca caatccagcc tgatccctgg gcagctgccc tccctcccgc   6360
agccacctct ggctctgaga gatgggcttg gggccagcct ggggtcccag gagtccaggc   6420
caggatgaga acctgctctg accccacctg gacgcattag gcctgcctgg acctgttgcc   6480
tcaccccaag agagccacag gcaatgcaaa ggctcctgtt catgtcaggg cacctggaag   6540
gcctgacttg cagaggctct tggctcgtgc agacccctcc aagcccaggc cctgcccacc   6600
acctcccctt tgtctctgga actgccagga cagcttgtcc tcagccagca ggtttcccga   6660
```

```
cccgggcacc tcttcatgtt gggccccccct cctttccctc catcagggat catgcccttc 6720
ttcaggggcc tggatatcaa ggacacaaaa gctcccatgt gctatgtggg gaggcagagt 6780
gggggctggg ttgagctggg gtctgggcag cgccattccg cagggcaggg gcagcctagg 6840
cttcccatct gtggaatggg tgggtgggtc tcacaacgga cctgcttccc gtacttcagc 6900
acggttacca ctcttgattg gaactctgac catgcatctc ctcttctgtt tacttcacgc 6960
tttctcttcc catcaactcc cattttaatt acaatttgtt taaaagcact gcatattact 7020
tcattaaaca gaagattagt ttcacttacc attagtgtaa ggtgactata gaaccaaagc 7080
agactggaaa ccaaatgaca taatgtcatt ctcttctcca ttccagctgc ctgctgctgt 7140
gcgcctgaga acccctgtgg agtgggaggg gcagctgtct ctgtacatta gaaagggagg 7200
ttaactaagt gacaggaggt gtttgggaca tgtggacacc agacttctct cttgatgcaa 7260
ggagggcaga gccaggcagc ctagtggggg ctggcttggg ggctgctgga aggactggct 7320
acaggtggaa gagaggtcag acctgaagct tggggccacc tccaggaaag gacaggtgaa 7380
agtggaggca tgaggcaggg gagaggcagg tgccaggcag agggtggaga ggaggcagga 7440
acatagcagc tggggcgggg gcgggcctca agtgtcatat gctactttcc tggggcccag 7500
gggcaaggac aggaacagcc acagcatgtg ttgggacaga gccctgtgcc ttcctagagc 7560
tgggcaggtg gaatggggca ggaatgggac tcgtggtggc tgcagcagga actggagggg 7620
aaggggcttc tggatcctgc agcctacctt cctagaggcc agctttccgg ggtccaccag 7680
gtgggtggga actgggcttg tgtagcaaga ctgccctgag gaccatccat gacatggtct 7740
agatgaaagt taggaaagaa agggagacaa gctggcagca gaagtacagc tgggtcagga 7800
gcaagggcct ttccagatag ggacaaccca agagtgcaca tgtgcccacg ccacacaaca 7860
caggcacaca cgacacgtgc acgctcatag gcactgcaca cacacatgca caggtgctca 7920
tgcatatgta tgagcttcat ctacacacat tcacatgccg tcctgcttat gtgcatgttt 7980
ccatacatgc acatgaatgc acaatcacgt gtacacacat gcatgtgatc acatacatga 8040
acatgtgtgc accccactcc tcaggtgcca tcgggctcct cctgctgtca ctgtgcagca 8100
ggggacatga ggccccagag cagacaggtg cagcacaggc gttcccaggc agtgccccac 8160
acacatgcat gagcacaccc gggcatgtgg cgcctccttt gtggactcag tcacctgcca 8220
ggtgggctcc ctggtggtgt gagctcccag aggtctggcg agagagataa aggcaacccc 8280
accaccaggc gtgctgagaa ttccctcttc tggctgggca cagtggctca tacctgtaat 8340
cccagcactt tgggaggccg aggtgggcag atcacttgag gttaggagtt tgagaccagc 8400
ctggccaata tggtgaaacc tcatctccac taaaaatata cacacacaaa aattagctgg 8460
gtgtggtggt gtgcacctgt agttccagct actcgggagg ctgaggcagg agaatcgctt 8520
gaacctggga gtcagagact gcagtgagcc gagatcatgt cactgcactc cagcccgggt 8580
gacagagtga gactccatct aaaaaaaaaa aagaattccc tcctctggga atttagacca 8640
cagacaggtt gcatgtatgt ggccgttgga ggcagcactc acagcaaaga gtggaaacgt 8700
caccacaggg cctgccttct ggtgaaaatg gtgtcctgca gggcgggcag ctgtttgagg 8760
gcaggtgtcc caggtgcggc ctgcagcagc ctgagggtca cagagcgcag tgctgggagt 8820
gcagagactt cccccacagg gagagttccc aggaacctgc ttccggtgca cttctggggg 8880
tttgagtttt ttccacggac gaattacttt gagaaaccac tgttactcgt gtgtataggt 8940
gagcgtgcgt gtgcatgtgt gttctgtgtg tgagtgtgca tgtatgtgcg tgcctgcgta 9000
tatatcctcg cagatacggc tagggacctc actcaggaca gtagttctgc ctgaggagag 9060
```

```
tgaatgcggc aagattgagg agaacacagg catcttcaaa ctacatgtgc ggtgctttat   9120

ttctttaaaa atgcgtctaa agcaaatagg aaaatgttaa gatttgaatc cgtagagtgt   9180

gggttctatt attctctcca catcttccat acgtttaaaa tcttttgcaa tgaaaataag   9240

ctgtagttaa agcagcaatg caggctgcca gtgagcgccc cggaggccag tgaggaccag   9300

catggctggg tggcctgttg gaatccaagg ggggcgggca ggagctgcag gcaggcgccc   9360

gggagtagcc cgggcatggg ggtgcggggc aacagggatg tctgcagggg tagcatgtgg   9420

gccccggact gcaagcaggt ggagccagcc ggatgcggct cctatgagaa aagcggggaa   9480

caagagacca cgctcgttct tcctgctgcg gggacagccc tggtcatcgc tccggggaac   9540

cctgcagcct gcgccgcacg tggccgcccc ctgctgcttc ctcctccccg gcctccgggt   9600

ggccttgctg acggctcctt ctctgaggca ggtctctgcc ttctcgcctg gtgcctgcac   9660

tcagtagccc cctcaccaga gctgctgggt gaaggaagca ctaagaaccc aaggctcggg   9720

aggagagtgg ggccgggaag ctgcagggaa gcgcagggcc aggcctggtg ggcccagggg   9780

ctggctcacg ggagggcagg agggagactg tggcggacag cacgtggggc caggaggtga   9840

cctccaagtg gattgtgggt gggttttttg tcctctttct gcattttcca ggcattttgt   9900

aatgtggata gaatatttct gttcttcaaa aatactttag ttaagaaaaa taagatggaa   9960

gctgttgcac ttgaaaatga ggaagccact ggtgatgcag ggggggcggc ggagaggacc  10020

tcttctgcaa atagcggcag gaacacggca tggatgcagc tcgcgctccc ccaggccctc  10080

ccctgggctg tgtggagggg tccgggggga atgggccagc gcccagtggt cacctggcca  10140

tgtctcccca cagcccggaa gcaggagatc attaagacca cggagcagct catcgaggcc  10200

gtcaacaacg gtgactttga ggcctacgcg t                                 10231
```

<210> SEQ ID NO 126
<211> LENGTH: 291
<212> TYPE: DNA
<213> ORGANISM: Homo sapiens

<400> SEQUENCE: 126

```
ctcagaattc aagatggata agccgccttc agtctcagcc aggctgtgct ctgggaaacc     60

tgagggaact ggctccaggg tcagctgagc caagctgctc atgtgacccc tctcctccca    120

ggctgctcac ttgctccagc cccggatgat gctgtgtgtt ttgctatttg tgaaccttgg    180

tccccaacag atgacacaaa tgcgtattgc tgtgcttgct ctgtgtgcgt gtgtgtgtgc    240

acgcgtgcgt gaatcattgc caaggaattg acacatcaca caaggtaata c             291
```

<210> SEQ ID NO 127
<211> LENGTH: 175
<212> TYPE: DNA
<213> ORGANISM: Homo sapiens

<400> SEQUENCE: 127

```
cccaggctgc tcacttgctc cagccccgga tgatgctgtg tgttttgcta tttgtgaacc     60

ttggtcccca acagatgaca caaatgcgta ttgctgtgct tgctctgtgt gcgtgtgtgt    120

gtgcacgcgt gcgtgaatca ttgccaagga attgacacat cacacaaggt aatac         175
```

<210> SEQ ID NO 128
<211> LENGTH: 144
<212> TYPE: DNA
<213> ORGANISM: Homo sapiens

```
<400> SEQUENCE: 128

cttccagctg cctgggtttc ctggaaagaa ctcttatccc caggaactag tttgttgaat     60

aaatgctggt gaatgaatga atgattgaac agatgaatga gtgatgagta gataaaagga    120

tggatggaga gatgggtgag taca                                           144


<210> SEQ ID NO 129
<211> LENGTH: 192
<212> TYPE: DNA
<213> ORGANISM: Homo sapiens

<400> SEQUENCE: 129

tccagcccta accactcagg attgggccgt ttgtgtctgg gtatgtctct tccagctgcc     60

tgggtttcct ggaaagaact cttatcccca ggaactagtt tgttgaataa atgctggtga    120

atgaatgaat gattgaacag atgaatgagt gatgagtaga taaaaggatg gatggagaga    180

tgggtgagta ca                                                        192
```